(12) United States Patent
Botts et al.

(10) Patent No.: US 7,452,546 B2
(45) Date of Patent: Nov. 18, 2008

(54) PARTICLES CONTAINING AGRICULTURAL ACTIVE INGREDIENTS

(75) Inventors: M. Francis Botts, St. Peters, MO (US); Frank C. Kohn, St. Louis, MO (US); Maria L. Miller, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/396,019

(22) Filed: Mar. 31, 2006

(65) Prior Publication Data
US 2006/0193882 A1 Aug. 31, 2006

Related U.S. Application Data

(60) Division of application No. 09/326,014, filed on Jun. 4, 1999, now Pat. No. 7,070,795, which is a continuation-in-part of application No. 09/104,565, filed on Jun. 25, 1998, now abandoned.

(60) Provisional application No. 60/051,285, filed on Jun. 30, 1997.

(51) Int. Cl.
*A01N 25/00* (2006.01)
*A01N 25/08* (2006.01)
*A01N 25/14* (2006.01)
*A01N 25/04* (2006.01)
*A01N 43/647* (2006.01)

(52) U.S. Cl. .................. 424/409; 424/405; 424/484; 424/485; 424/487; 424/489; 424/500; 424/501; 504/272; 523/122

(58) Field of Classification Search .................. 424/409, 424/405, 417, 418, 419, 420, 421, 484, 486, 424/487; 47/57.6; 504/272; 514/383; 523/122
See application file for complete search history.

(56) References Cited

U.S. PATENT DOCUMENTS

| | | | |
|---|---|---|---|
| 3,523,906 A | 8/1970 | Vrancken et al. | 252/316 |
| 3,523,907 A | 8/1970 | Vrancken et al. | 252/316 |
| 3,577,515 A | 5/1971 | Vandegaer | 24/32 |
| 3,645,911 A | 2/1972 | Van Besauw et al. | 252/316 |
| 3,929,453 A | 12/1975 | Dimitri et al. | 71/101 |
| 4,000,290 A | 12/1976 | Itzerott | 424/270 |
| 4,142,526 A | 3/1979 | Zaffaroni et al. | 128/260 |
| 4,155,741 A | 5/1979 | Scher et al. | 71/65 |
| 4,172,119 A * | 10/1979 | Kuchner et al. | 424/419 |
| 4,186,185 A | 1/1980 | Capozza | 424/19 |
| 4,230,809 A | 10/1980 | Heinrich et al. | 521/65 |
| 4,235,872 A | 11/1980 | Tocker | 424/19 |
| 4,272,398 A | 6/1981 | Jaffe | 252/316 |
| 4,303,642 A | 12/1981 | Kangas | 424/78 |
| 4,363,815 A | 12/1982 | Yu et al. | 424/274 |
| 4,479,911 A | 10/1984 | Fong | 264/4.6 |
| 4,479,961 A | 10/1984 | Martin | 424/270 |
| 4,512,969 A | 4/1985 | Chen | 424/81 |
| 4,534,783 A | 8/1985 | Beestman | 71/27 |
| 4,563,212 A | 1/1986 | Becher et al. | 71/118 |
| 4,585,482 A | 4/1986 | Tice et al. | 106/15.05 |
| 4,622,244 A | 11/1986 | Lapka et al. | 427/213.32 |
| 4,637,905 A | 1/1987 | Gardner | 264/4.3 |
| 4,640,709 A | 2/1987 | Beestman | 71/100 |
| 4,652,441 A | 3/1987 | Okada et al. | 424/19 |
| 4,664,696 A | 5/1987 | Schaub | 71/92 |
| 4,723,984 A | 2/1988 | Holmwood et al. | 71/76 |
| 4,906,652 A | 3/1990 | Karbach et al. | 514/383 |
| 4,915,947 A | 4/1990 | Thenard et al. | 424/408 |
| 4,937,254 A | 6/1990 | Sheffield et al. | 514/420 |
| 4,965,128 A | 10/1990 | Greidanus et al. | 428/398 |
| 5,139,687 A * | 8/1992 | Borgher et al. | 510/515 |
| 5,156,843 A | 10/1992 | Leong et al. | 424/411 |
| 5,225,278 A | 7/1993 | Kielbania, Jr. et al. | 428/402.22 |
| 5,271,961 A | 12/1993 | Mathiowitz et al. | 427/213.31 |
| 5,277,979 A | 1/1994 | Kielbania, Jr. et al. | 428/402.21 |
| 5,302,654 A | 4/1994 | Ishii et al. | 524/458 |
| 5,360,892 A | 11/1994 | Bonsignore et al. | 528/354 |
| 5,484,779 A * | 1/1996 | Sauter et al. | 514/63 |
| 5,484,881 A | 1/1996 | Gruber et al. | 528/354 |
| 5,512,600 A | 4/1996 | Mikos et al. | 521/61 |

(Continued)

FOREIGN PATENT DOCUMENTS

AU A 2895189 8/1989

(Continued)

OTHER PUBLICATIONS

International Search Report for International Application No. PCT/US98/13378 dated Dec. 30, 1998.

(Continued)

*Primary Examiner*—Johann Richter
*Assistant Examiner*—James H Alstrum-Acevedo
(74) *Attorney, Agent, or Firm*—Nelson Mullins Riley & Scarborough, LLP

(57) ABSTRACT

One or more agricultural active ingredients (such as fungicides or insecticides) are entrapped in polymeric matrixes to form particles having a diameter in the range from about 0.2 to about 200 microns. The particles are applied to soil, to seeds, or to plants and release the active ingredient(s) at a rate sufficiently low to avoid phytotoxicity but at a rate sufficiently high to provide effective amounts of the active ingredient(s), preferably throughout the growing period of the plant.

28 Claims, 17 Drawing Sheets

U.S. PATENT DOCUMENTS

| | | | | |
|---|---|---|---|---|
| 5,536,807 | A | 7/1996 | Gruber et al. | 528/354 |
| 5,589,194 | A | 12/1996 | Tsuei et al. | 424/497 |
| 5,719,103 | A | 2/1998 | Dao et al. | 504/116 |
| 5,725,869 | A * | 3/1998 | Lo | 424/408 |
| 5,866,153 | A * | 2/1999 | Hasslin et al. | 424/408 |
| 5,914,295 | A | 6/1999 | Hoffmann et al. | 504/116 |
| 6,103,253 | A | 8/2000 | Hoffmann et al. | 424/407 |

FOREIGN PATENT DOCUMENTS

| | | |
|---|---|---|
| DE | 1 960 430 | 7/1971 |
| DE | 31 50631 A1 | 7/1983 |
| DE | 3 737 888 | 5/1989 |
| EP | 0 004 758 | 10/1979 |
| EP | 0 018 119 | 10/1980 |
| EP | 0 201 214 | 11/1983 |
| EP | 0196 038 | 10/1986 |
| EP | 0 255 752 | 2/1988 |
| EP | 0 287 346 | 10/1988 |
| EP | 0 300 777 | 1/1989 |
| EP | 0 356 240 | 2/1990 |
| EP | 0 364 406 | 4/1990 |
| EP | 0 415 569 | 3/1991 |
| EP | 0 504 761 A1 | 9/1992 |
| EP | 0 330 180 | 9/1993 |
| EP | 0 661 250 | 7/1995 |
| EP | 0 729 700 | 9/1996 |
| EP | 0 763 510 | 3/1997 |
| FR | 2 635 640 | 2/1990 |
| FR | 2 702 929 A1 | 9/1994 |
| JP | 61236820 | 10/1986 |
| JP | 60-48923 | 9/1993 |
| JP | 05286966 | 1/1994 |
| JP | 07053685 | 5/1995 |
| WO | WO 88/08300 | 11/1988 |
| WO | WO 89/07935 | 9/1989 |
| WO | WO 90/03732 | 4/1990 |
| WO | WO 91/11306 | 8/1991 |
| WO | WO 92/05866 | 4/1992 |
| WO | WO 92/13448 | 8/1992 |
| WO | WO 93/20138 | 12/1993 |
| WO | WO 96/37103 | 11/1996 |

OTHER PUBLICATIONS

Bateman, "Formulation of Soil-Applied Fungicides for Controlling Take-All (Gaemannomyces graminis var. tritici) in Experiments with Pot-Grown Wheat," Zeitschrift fur Pflanzenkranheiten und Pflanzenschutz (1982), vol. 89, No. 8/9, pp. 480-486. (Abstract only).

Carter et al., "Temperature-activated Release of Trifluralin and Diazinon," Pesticide Formulations and Application Systems: 11th volume, (1992), Proceedings of a Conference on Pesticide Formulation sand Application Systems held in San Antonio, USA, Nov. 14-15, 1991, STP series No. 1112.5 ref.

Carter et al., "Temperature-Activated Release of Trifluralin and Diazinon," ASTM Spec. Tech. Publ. (1992), STP 1112 (Pestic. Formulations Appl. Syst: 11th Vol.), pp. 57-69.

Coffman et al., "Persistence of Several Controlled Release Formulations of Trifluralin in Greenhouse and Field," Weed Sci. (1980), 28(l), pp. 21-23.

Greene et al., "Temperature Controlled Pesticide Release Systems," Proceedings of the Brighton Crop Protection Conference, Pests and Diseases (1990), vol. 2, pp. 593-598.

Jaffe et al., "Injectable Formulations for Controlled Release of Pesticides Against Ticks on Cattle," Proc.-Int. Controlled Release Pestic. Symp. (1977), pp. 272-284.

Jaffe, "Implantable Systems for Delivery of Insect Growth Regulators to Livestock," Controlled Release Biact. Mater. [Symp. Int. Meet. Controlled Release Soc.], 6th (1980), Meeting Date 1979, pp. 237-250. (Abstract only).

Krishnan et al., "Controlled Release of Bioactive Compounds with Special Reference to Agriculture," Popular Plastics (1978), 23(4), pp. 28-33.

Langer et al., "Chemical and Physical Structure of Polymers as Carriers for Controlled Release of Bioactive Agents: A Review," JMS-Rev. Macromol. Chem. Phys. (1983), C23(1), pp. 61-126.

Markus et al., "Encapsulation of Triphenyltin Hydroxide," J. Microencapsulation (1986), 3(1), pp. 39-42.

Marrs et al., "Seed Treatment with Tefluthrin-a Novel Pyrethroid Soil Insecticide," Monograph—British Crop Protection Council (1988), No. 39, pp. 17-23.

Marrs et al., "The Formulation of Pesticides for Convenience and Safety," Outlook on Agriculture (1973), vol. 7, No. 5, pp. 231-235.

Maskell et al., "Chemical Control of Wheat Bulb Fly (Delia coarctata) Attacking Winter Wheat in Eastern England, 1969-1981 I. Insecticidal Seed Treatments," Ann. Appl. Biol. (1986), 109, pp. 223-236.

Mason et al., "In Vivo and In Vitro Evaluation of a Microencapsulated Narcotic Antagonist," J. Pharm. Sci. (1976), 65(6), pp. 847-850. (Abstract only).

Mathiowitz et al., "Polyanhydride Microspheres: 3. Morphology and Characterization of Systems Made by Solvent Removal," Polymer (1990), vol. 31, pp. 547-555.

Mathiowitz et al., "Polyanhydride Microspheres As Drug Carriers I. Hot-Melt Microencapsulation," J. of Controlled Release (1987) 5, pp. 13-22.

Matthews et al., "Improving Ryegrass Establishment with Microencapsulated Fonofos Insecticide," Crop Protection (1987), vol. 6, No. 5, pp. 313-319.

Meghir, "Microencapsulated Insecticides," Mededelingen van de Faculteit Landbouwwetenschappen Rijksuniversiteit Gent (1980), vol. 45, pp. 513-527.

Ogawa et al., "A New Technique to Efficiently Entrap Leuprolide Acetate into Microcapsules of Polylactic Acid or Copoly (Lactic/Glycolic) Acid," Chem. Pharm. Bull. (1988), 36(3), pp. 1095-1103).

Ohtsubo et al., "Formulation Factors Affecting the Efficacy, Phytotoxicity and Rainfastness of Fenitrothion Microcapsules for Agricultural Use," J. of Pesticide Science (1991), vol. 16, No. 4, pp. 609-614.

Ohtsubo et al., "Formulation Factors of Pyrethroid Microcapsules Affecting Rainfastness, Phytotoxicity and Mammalian Toxicity," J. of Pesticide Science (1991), vol. 16, No. 3, pp. 413-418.

Pothakamury et al., "Fundamental Aspects of Controlled Release in Foods," Trends in Food Science & Technology (1995), vol. 6, pp. 397-406.

Sinclair, "Slow-Release Pesticide System: Polymers of Lactic and Glycolic Acids as Ecologically Beneficial, Cost-Effective Encapsulating Materials," Environmental Science & Technology (1973), vol. 7, No. 10, pp. 955-956.

Stock, "Achieving Optimal Biological Activity from Crop Protection Formulations: Design or Chance?," Proc. Br. Crop Prot. Conf. Pests Dis (1996), 3, pp. 791-800. (Abstract only).

Thies, C., "Formulation of Degradable Drug-Loaded Microparticles by In-Liquid Drying Processes," *Microparticles and Nanoparticles in Medicine and Pharmacy*, M. Donbrow, ed., CRC Press, Boca Raton, FL (1992), pp. 47-41.

Thompson et al., "Control of Cotton Leak of Cucumber with Different Formulations of Metalaxyl Applied at Various Rates and Times," Phytopathology (1985), 75, No. 11, pp. 1362-1363.

Canadian Intellectual Property Office Examination dated Jul. 10, 2006, Canadian Patent Application No. 2, 294,332.

* cited by examiner

PARTICLES CONTAINING AGRICULTURAL ACTIVE INGREDIENTS

RELATED APPLICATION

This application is a divisional of U.S. patent application Ser. No. 09/326,014, filed Jun. 4, 1999 now U.S. Pat. No. 7,070,795, which is a continuation-in-part of U.S. patent application Ser. No. 09/104,565, filed Jun. 25, 1998 (abandoned), which was a non-provisional of U.S. Provisional Application No. 60/051,285 filed Jun. 30, 1997, each of which is incorporated herein by reference.

BACKGROUND OF THE INVENTION

This invention relates to compositions and methods for controlled release of agricultural chemicals.

An agricultural chemical, such as a biocide, a chemical hybridizing agent, or a plant growth regulator is applied to a plant, to a seed, or to soil at the beginning of a growing season and must maintain their effectiveness throughout the growing season, which can last for several months. However, the agricultural chemical may be degraded by chemical or biological processes and removed by wind or water from the site of application. As a result, it is necessary to apply high rates of the agricultural chemical to maintain the desired effect over time or to apply the chemical repeatedly during the growing season. However, high rates of certain agricultural chemicals can be phytotoxic to a plant which is sought to be protected ("agronomic plant") from the disease or pest which the agricultural chemical is meant to control. For example, many fungicides, such as triazole fungicides, can be phytotoxic to the agronomic plant when applied in amounts that are necessary to provide agronomically adequate disease control.

Numerous triazole fungicides have been developed and commercialized. The triazole fungicides are generally characterized as having a 1H-1,2,4-triazole group. Some individual representative triazole fungicides are listed in the table below.

| Triazole Fungicide | CAS Registry Number |
|---|---|
| bitertanol | 70585-36-3 |
| bromuconazole | 116255-48-2 |
| cyproconazole | 94361-06-5 |
| difenoconazole | 119446-68-3 |
| epoxiconazole | 106325-08-0 |
| fenbuconazole | 114369-43-6 |
| fluquinconazole | 136426-54-5 |
| flusilazole | 85509-19-9 |
| flutriafol | 76674-21-0 |
| hexaconazole | 79983-71-4 |
| imibenconazole | 86598-92-7 |
| metconazole | 125116-23-6 |
| myclobutanil | 88671-89-0 |
| penconazole | 66246-88-6 |
| propiconazole | 60207-90-1 |
| tebuconazole | 107534-96-3 |
| tetraconazole | 112281-77-3 |
| triadimefon | 43121-43-3 |
| triadimenol | 55219-65-3 |
| triticonazole | 131983-72-7 |

Under certain conditions, a triazole fungicide frequently is phytotoxic to the very plant species the fungicide is meant to protect from disease. For example triadimefon can be phytotoxic to ornamental plants (The Pesticide Manual, Eleventh Edition, C. D. S. Tomlin, ed., The British Crop Protection Council, Farnham, Surrey, U.K., 1997, p. 1217); metconazole can cause stunting and yellowing of plants (Id., p. 804); hexaconazole can cause damage to McIntosh apples (Id., p. 675); difenoconazole can cause chlorosis in wheat (Id., p. 390); and bitertanol can cause damage to fruit crops (Id., p. 132).

Controlled release of a pesticide has occasionally been used as a method of controlling phytotoxicity of the pesticide to the beneficial plant species. Patents and published patent applications disclosing various controlled-release formulations include each of the following individual disclosures.

U.S. Pat. No. 4,172,119.
U.S. Pat. No. 4,915,947.
U.S. Pat. No. 5,225,278.
U.S. Pat. No. 5,277,979.
U.S. Pat. No. 5,725,869.
European Patent Publication No. 0 004 758-A2.
European Patent Publication No. 0 018 119-A1.
European Patent Publication No. 0 763 510-A1.
PCT Patent Application No. WO 88/08300.

SUMMARY OF THE INVENTION

Thus, there is a continuing need for controlled-release formulations by which an agricultural chemical can be delivered to a plant over the entire growing season at a concentration or rate which is agronomically effective, while reducing plant phytotoxicity relative to current commercially used practices. There is especially a need for a controlled-release formulation of a fungicide such as a triazole fungicide which can provide effective fungicidal control over a period of time without causing unacceptable phytotoxic damage to an agriculturally beneficial plant to which the formulation is applied.

Preferably, such formulations would include an amount of an active ingredient that is close to the minimum amount needed to obtain the desired effect in order to reduce environmental impacts and to reduce costs.

Among the many embodiments of the present invention may be noted a controlled-release formulation which comprises a particle in which one or more agricultural active ingredients are dispersed or distributed in a polymeric matrix. Such controlled-release formulations are safe when applied to seeds or to plants even though they contain levels of active ingredients that would be phytotoxic if applied to the seeds or plants in standard fast-release formulations. The particle of the present invention can release at least one active ingredient at biocidally beneficial levels over a period during the germination and growth of an agriculturally beneficial plant (e.g., for at least two to twelve weeks or more) and therefore can reduce or eliminate the need for subsequent applications of the agricultural chemical. The rate of release of agricultural chemicals, and the period over which effective amounts of such chemicals can be released, can be tailored as desired. Such controlled-release compositions thus increase the period during which an agricultural chemical is effective, reduce the initial toxicity of the chemical to seeds or crop plants, expand the range of compounds that can be used for agricultural applications, and decrease the environmental impact of chemical treatment.

In one embodiment, the present invention presents a particle comprising a triazole fungicide in a polymer matrix. Preferably, the triazole fungicide comprises a compound selected from the group consisting of bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, and triticonazole. The present invention further embodies a fungicidal composition comprising a particle comprising a triazole fungicide in a polymer matrix, and an agricultural adjuvant.

In another embodiment of the invention, controlled-release compositions for delivering an agricultural chemical to a plant comprise particles having an average diameter of about 0.1 microns to about 200 microns, the particles each comprising a polymer matrix and at least one agricultural chemical distributed throughout the polymer matrix. The particles include about 1 to about 50% by weight of the agricultural chemical and about 50% to about 99% by weight of the polymer matrix.

In a further embodiment, the present invention provides compositions including suspensions of the particles in an aqueous medium, wettable powders, wettable granules, dry granules, and seed coatings, for example. According to at least some embodiments of the invention, the particles adhere to a surface of a seed or plant.

A further embodiment of the present invention comprises compositions which include an amount of the agricultural chemical and which release the agricultural chemical at a rate such that the composition delivers an agriculturally active amount of the agricultural chemical to the plant for a period of at least about two weeks to about twelve weeks, preferably throughout the growth period of the plant.

In yet another embodiment of the invention, such compositions as described in the present disclosure can be used in a method to reduce the phytotoxicity of the agricultural chemical by at least two-fold (i.e., at least a 50% reduction in phytotoxicity as compared to conventional fast-release formulations of the chemical). For example, in the case of seed coating compositions according to the present invention, the composition can include an amount of the agricultural chemical that would be substantially phytotoxic if applied to the surface of the seed as a fast-release formulation of the agricultural chemical. One embodiment of the present invention provides a method for the treatment or prophylaxis of a fungal disease in a target plant wherein the method comprises contacting a plant cell, a plant tissue, or a seed with a particle wherein the particle comprises a triazole fungicide in a polymer matrix and wherein after the contacting, the health of the target plant is substantially similar to the health of a control plant which is substantially free of the fungal disease and which is free of contact with the triazole fungicide.

Another embodiment of the present invention provides a method for the treatment or prophylaxis of a fungal disease in a target plant wherein the method comprises contacting a plant cell, a plant tissue, or a seed with a particle wherein the particle comprises a triazole fungicide in a polymer matrix and wherein after the contacting, the health of the target plant is intermediate between the health of a first control plant which is substantially free of the fungal disease and which is free of contact with the triazole fungicide, and the health of a second control plant which is substantially free of the fungal disease and which is contacted with the triazole fungicide in the absence of the polymer matrix. Commercially acceptable levels of disease control (e.g., fungal control) frequently results from plants in which less than 100% of the disease agent (e.g. a fungus) has been eradicated. For example, in some circumstances and markets, a treatment providing 60-80% fungal disease control is considered commercially acceptable.

In a further embodiment of the invention, the agricultural chemical comprises a biocide (e.g., a triazole fungicide such as bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, or triticonazole), a plant growth regulator, a chemical hybridizing agent, a plant nutrient, or combinations thereof.

In one embodiment, the polymer used in the compositions of the present invention is selected from the group consisting of poly(methylmethacrylate), poly(lactic acid), poly(lactic acid-glycolic acid) copolymers, cellulose acetate butyrate, poly(styrene), hydroxybutyric acid-hydroxyvaleric acid copolymers, styrene maleic anhydride copolymers, poly(methylvinyl ether-maleic acid), poly(caprolactone), poly(n-amylmethacrylate), wood rosin, polyanhydrides, polyorthoesters, poly(cyanoacrylates), poly(dioxanone), ethyl cellulose, ethyl vinyl acetate polymers, poly(ethylene glycol), poly(vinylpyrrolidone), acetylated mono-, di-, and trigylcerides, poly(phosphazene), chlorinated natural rubber, vinyl polymers, polyvinyl chloride, hydroxyalkylcelluloses, polybutadiene, polyurethane, vinylidene chloride polymers, styrene-butadiene copolymers, styrene-acrylic copolymers, alkylvinylether polymers, cellulose acetate phthalates, ethyl vinyl pthalates, cellulose triacetate, polyanhydrides, polyglutamates, polyhydroxy butyrates, polyvinyl acetate, vinyl acetate-ethylene copolymers, vinyl acetate-vinylpyrrolidone copolymers, acrylic polymers, alkyl acrylate polymers, aryl acrylate polymers, aryl methacrylate polymers, poly(caprolactams), epoxy resins, polyamine epoxy resins, polyamides, polyvinyl alcohol polymers, polyalkyd resins, phenolic resins, abietic acid resins, silicones, polyesters, and copolymers and combinations thereof.

The present invention further embodies compositions which include a dispersing agent, such as methyl cellulose, poly(vinyl alcohol), lecithin, and combinations thereof.

In another embodiment of the invention, seeds are provided that comprise such compositions, e.g., as seed coatings.

A further embodiment of the invention provides a method for delivering an agricultural chemical to a plant wherein the method comprises providing to the plant a composition as discussed above, for example, by application of the composition to soil, application of the composition to foliage of the plant, and coating a seed prior to germination of the seed to produce the plant. When applied to soil or foliage the composition can be applied, for example, in an amount such that about 1 g to about 10 kg of the agricultural chemical is applied per hectare. When applied as a seed coating, the composition can be applied in an amount such that about 1 gram to about 500 grams of the agricultural chemical is applied to 100 kg of seed.

In a further embodiment of the invention, methods are provided for producing the compositions described above. Such methods include the steps of: (a) dissolving at least one agricultural chemical (for example, a triazole fungicide) and a polymer in a to form a hydrophobic solution; (b) mixing the hydrophobic solution and an aqueous medium at a shear rate and for a time period sufficient to produce an emulsion having droplets of the hydrophobic solution dispersed in the aqueous medium; and (c) evaporating the organic solvent from the emulsion to produce a plurality of particles having an average diameter of about 0.2 micron to about 200 microns and comprising said at least one agricultural chemical distributed throughout a polymer matrix. According to some embodiments of the invention, such methods include one or more of the further steps of: dissolving a dispersing agent in an aqueous solution to produce the hydrophilic solution; and suspending the particles in an aqueous medium.

A preferred embodiment of the present invention provides a method of producing a particle wherein the particle comprises a triazole fungicide in a polymer matrix, and the method comprises providing a hydrophobic solution comprising a triazole fungicide, a polymer, and a solvent; mixing the hydrophobic solution and an aqueous medium to produce a dispersion of droplets of the hydrophobic solution in the aqueous medium; and evaporating the solvent from the dispersion to produce a particle comprising a triazole fungicide in a polymer matrix.

A further embodiment of the present invention provides a method of producing a particle wherein the particle comprises a triazole fungicide in a polymer matrix, the method comprising the steps of providing a hydrophobic solution comprising a triazole fungicide, a polymer, and a solvent; mixing the hydrophobic solution and an aqueous medium to produce a dispersion of droplets of the hydrophobic solution in the aqueous medium; and evaporating the solvent from the dispersion to produce a particle comprising a triazole fungicide in a polymer matrix.

The present invention also embodies a method for the treatment or prophylaxis of a fungal disease in a target plant wherein the method comprises contacting a plant cell, a plant tissue, or a seed with a particle wherein the particle comprises a triazole fungicide in a polymer matrix.

Other aspects of the present invention will become apparent to those skilled in the art upon studying this disclosure and the accompanying claims.

DETAILED DESCRIPTION OF THE INVENTION

Figure 1:
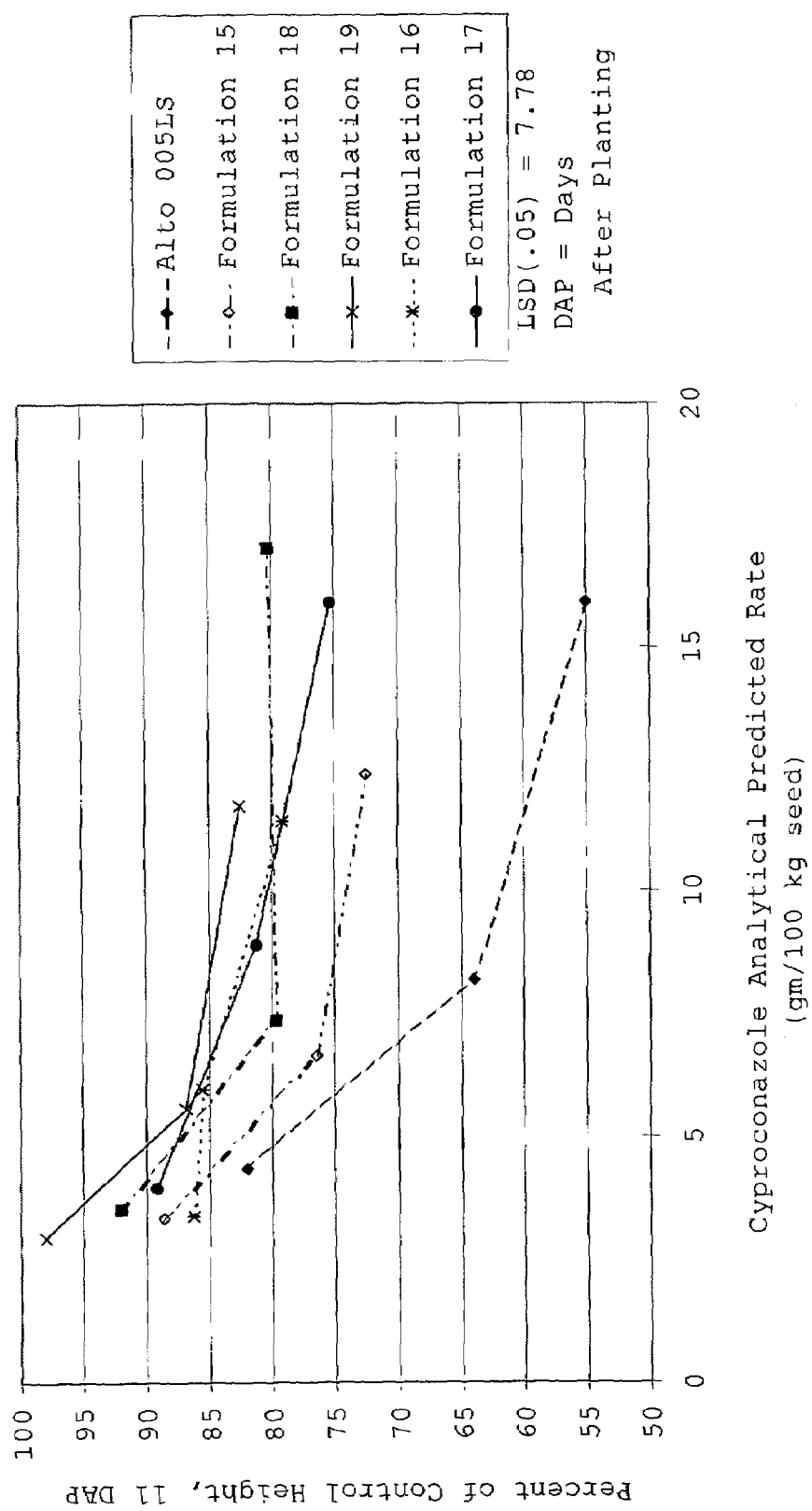
FIG. 1 shows the effect of matrix particle formulations of Example 7 and ALTO® 005LS (cyproconazole formulation) when used as seed treatments on wheat at various rates (g cyproconazole per 100 kg seed), expressed as the height of germinating wheat at 11 days after planting (DAP) as a percent of the height of untreated controls.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Agricultural chemical" or "active ingredient" means a chemical which is useful in the control of a disease or a pest (including without limitation a weed, an insect, a parasite, and a fungus) in agricultural settings.

The abbreviation "a.i." means active ingredient.

"Phytotoxic" means injurious to vegetation.

"Agronomic plant" means a plant useful in agriculture and which is sought to be protected from disease or pests.

"Agriculturally beneficial" means useful or productive in agriculture.

"Agricultural adjuvant" or "inert ingredient" means a material used in an agricultural formulation or composition to aid in the operation or to improve the effectiveness of an agricultural chemical. The term includes such materials as a wetting agent, a spreader, an emulsifier, a dispersing agent, a foaming adjuvant, a foam suppressant, an antifoam, a penetrant, a corrective, a surfactant, a solvent, a solubilizer, a buffering agent, and a sticker.

The term "combination" is intended to embrace application of each agent in a sequential manner in a regimen that will provide beneficial effects of the agricultural chemical combination, and is intended as well to embrace compositions or co-administration of these agents in which the presence or application of these agents occurs in a substantially simultaneous manner, such as in a single spray mixture or treatment having a fixed ratio of these active agents.

b. Compositions and Methods

The matrix-particle formulations of this invention are useful in agriculture for a number of purposes, including, for example, the control of seed-borne and soil-borne pathogens and pests, as well as pests affecting above-ground portions of plants (for example, stems, foliage, flowers, fruits), and underground portions (for example, roots, rhizomes, tubers) for the delivery of nutrients, chemical hybridizing agents and plant growth regulators, and the like. It will also be appreciated that such formulations have a number of non-agricultural uses, such as in the delivery of pharmaceuticals to humans or to animals for therapeutic or prophylactic purposes; for the controlled release of chemicals in water treatment or conditioning, aquaculture, etc.

Controlled-release formulations according to the present invention substantially reduce the phytotoxicity of an agricultural chemical to a seed or a plant compared to a standard fast-release formulation of the chemical (i.e., one having a release rate that is substantially similar to that of the unformulated chemical). That is, such controlled-release formulations reduce the toxicity of, and correspondingly increase the "safety" of (or "safen"), the agricultural chemical. Therefore, for a given level of phytotoxicity, more of the chemical can be applied to a seed or a plant in the form of a controlled-release formulation according to the present invention than in a standard fast-release formulation. Preferably, a controlled-release formulation according to the present invention safens a particular chemical by at least two-fold (i.e., at least a 50% reduction in phytotoxicity as compared to conventional fast-release formulations of the chemical), more preferably by at least five-fold (i.e., at least a 80% reduction in phytotoxicity as compared to conventional fast-release formulations of the chemical), yet more preferably by at least ten-fold (i.e., at least a 90% reduction in phytotoxicity as compared to conventional fast-release formulations of the chemical), and most preferably by at least twenty-fold (i.e., at least a 95% reduction in phytotoxicity as compared to conventional fast-release formulations of the chemical). In fact, we have applied greater than one hundred times the amount of standard formulations of certain phytotoxic chemicals with only minimal injury to plants. As shown in the Examples below, the safening of various agricultural chemicals such as triazole fungicides permits their use as seed treatments at levels that would otherwise prevent germination or stunt the growth of plants that germinate from the seeds, making them more effective against various pathogens and pests.

Matrix particle. The term "matrix" is defined as a surrounding material in which another material is entrapped, embedded, dissolved, dispersed or otherwise distributed. Particles of the present invention comprise a matrix that includes one or more polymers in which one or more active ingredients are entrapped, embedded, dissolved, dispersed, or otherwise distributed. The particles may also include one or more inert ingredients or additives, such as dispersants. The particles of the present invention differ from "microcapsules," in which a polymeric shell surrounds a liquid or solid core that contains an active ingredient. The core of the particle may be divided into a number of separate domains or multiple cores. In at least some embodiments of the particles of the present invention, the final product appears in freeze-fracture electron micrographs as solid, generally spherical particles that appear solid throughout, indicating that the active ingredient(s) is distributed or dispersed within the matrix material. The distribution may be at a molecular level or the distribution may be as finely divided pockets comprising a plurality of molecules of the active ingredient. The distribution may be substantially uniform throughout the matrix material or the distribution may exhibit a concentration gradient through a cross-section of the matrix material. Therefore it is possible in at lease some embodiments that an active ingredient may be macromolecularly distributed in the matrix, i.e., that a plurality of particles of the active ingredient are dispersed in the matrix.

The agriculturally active ingredient can comprise about 1.0% to about 50% by weight, preferably about 15% to about 50% by weight of the particle of the present invention. The particle can comprise from about 50 to about 99% by weight of matrix material. It is preferred that the particle comprise from about 50% to about 90% by weight of the matrix material. It is particularly economical if the particle comprises a high proportion of the active ingredient. If the proportion of matrix material to entrapped active ingredient is too high, the rate of release of the entrapped material may decrease, thereby causing a decrease in the biological efficacy of the treatment, and causing an increase in the cost of a biologically effective amount of the final product. If the proportion of the matrix component to the entrapped material component is too small, the rate of release may be unacceptably high, leading to phytotoxicity and reducing the period of effectiveness of the active ingredient. As the concentration of the active ingredient increases in the particle, the release rate will also generally increase.

The average matrix component concentration, as a percent of the total weight of the matrix particle (combined weight of matrix, active ingredient and any other ingredients associated with the polymer matrix), can be estimated from the amount of ingredients in the composition used for preparing the particle.

The particle of the present invention preferably has an average particle size in the range of about 0.2 microns to about 200 microns in diameter. Release rate of the active ingredient is generally inversely proportional to the average particle size. Frequently plant phytotoxicity of the treatment comprising the particle of the present invention is inversely proportional to the average particle size. Smaller average particle sizes generally have a higher release rate and area coverage of active ingredient, together with a higher activity and phytotoxicity of the active ingredient. Conversely, larger average particle sizes are associated with low area coverage and reduced phytotoxicity, but also lower activity and phytotoxicity. In addition, the small size of the particle of the present invention will permit the particle to be taken up by a plant together with soil water and to be transported throughout the plant, effecting systemic delivery of active ingredient. The average particle size is preferably about 1 micron to about 50 microns in diameter, more preferably about 3 to about 50 microns. The size of the matrix particles is controlled during the process of entrapment by employing a mixing, stirring, or agitating means (for example, a blender, a rotostator, a shaker, a vibrator, a homogenizer, a mill, a microdropping syringe, or a sonicator at a suitable rate of speed to form droplets of the ingredients to be entrapped.

The particle size distribution of a batch of matrix particles of the present invention can be monomodal, bimodal, or polymodal. The different modalities can offer different advantages depending upon the desired application. For example, a monomodal particle size distribution may provide a relatively uniform release rate of the active ingredient. In contrast, a bimodal or a polymodal particle size distribution may provide more than one release rate of the active ingredient, thereby affording an active ingredient release rate profile tailored to the specific agricultural situation.

The particle size of the matrix particle of this invention is measured by using a microscope with a calibrated reticle and visually estimating the average particle size. Alternatively, the size can be determined by electronic means, for example by using a Coulter LS Counter or by laser light scattering. Microscopic determination generally is within 5 microns of the size measured by the Coulter Counter. From the distribution of particle sizes, $d_{16}$, $d_{50}$ and $d_{84}$ values are determined and plotted in a log probability plot. The $d_{16}$ value represents the size (diameter in microns) at which 16 weight percent of the capsules in the sample are equal to or larger than $d_{16}$, $d_{50}$ represents the size at which 50 weight percent of the capsules are equal to or greater in diameter than $d_{50}$, and $d_{84}$ represents the size at which 84 weight percent of the particles are equal to or greater in diameter than $d_{84}$.

The particle of the present invention preferably adheres to the surface of a seed or a plant. Without being limited by theory, it is thought that the particle becomes trapped in microhairs or in crevices on the seed or plant surface. Alternatively, the particle may adhere to a surface moiety of the plant, such as to the cuticle. Adhesion of the particle to the seed or the plant can be enhanced or achieved by the use of conventional "sticking agents" (i.e., "stickers" or "tackifiers") or other compounds that have been used for applying various coatings to seeds.

Particles can affect the mobility of an active ingredient in soil, since the binding or retention of the particle to soil can be substantially different than the binding of the active ingredient itself. As a result, depending on the matrix material selected, the composition according to the present invention can increase the effectiveness of an agricultural chemical that would be rendered less effective due to tight binding of the agricultural chemical to soil.

Also encompassed by the present invention is a particle comprising an agricultural chemical (such as a triazole fungicide) in a polymer matrix wherein the particle further comprises an encapsulation shell or coating on the surface of the particle. Such shell or coating can be applied to the particle by conventional methods and can provide further control of release of active ingredients, add additional active or other ingredients, or confer desirable properties to the resulting product.

Polymer. The term "polymer" or "polymeric material" as used in this invention is taken to mean either a single polymer or a combination of different polymers or a copolymer. The particle comprises from about 50% to about 99% by weight of the polymeric material, preferably from about 50% to about 90% by weight.

A matrix material is selected so that the rate of release of the active ingredient provides an "agriculturally effective amount" of the active ingredient, i.e., an amount of the active ingredient that is effective to achieve a desired level crop protection or other desired agricultural activity characteristically associated with the agricultural chemical. Thus, for a biocide, an agriculturally effective amount is an amount that is sufficient to provide commercially acceptable control of a pathogen or pest; for a plant growth regulator, an amount that is sufficient to substantially alter the growth or development of the plant in a manner characteristic of the plant growth regulator; for a nutrient, an amount that is sufficient to provide at least the minimum amount of the nutrient required for normal plant growth and development. Preferably, the active ingredient is released at a rate that does not cause substantial phytotoxicity, i.e., does not reduce the growth or vigor of the plant to commercially unacceptable levels or produce other types of unacceptable damage to the plant. Preferably, the active ingredient is released at beneficial levels throughout the period of germination, emergence, later developmental stages of the crop or plant, or throughout the entire growth period of the plant. The active ingredient may be released by diffusion from the matrix or by the degradation or dissolution of the matrix in the plant, soil or foliar environment. In addition, the polymer and breakdown products thereof, if any, should not substantially interfere with the effectiveness of the active ingredient (or other components, such as the dispersing agent) or be substantially phytotoxic to the seed, seedling or plant.

Examples of suitable polymers for the practice of this invention include but are not limited to the following non-exhaustive list of polymers (and copolymers and mixtures thereof):

poly(methylmethacrylate)
poly(lactic acid) CHRONOPOL™ 50, 95, and 100 (poly(lactic acid) formulation)) and copolymers such as poly(lactic acid-glycolic acid) copolymers (LACTEL® BP 400 (poly(DL-lactide-co-glycolide) formulation)) and combinations with polystyrene, for example
cellulose acetate butyrate
poly(styrene)

hydroxybutyric acid-hydroxyvaleric acid copolymers (BIOPOL® D400G (poly(3-hydroxybutyrate-co-hydroxyvalerate) formulation)
styrene maleic anhydride copolymers (SMA® 1440 A Resin (ester/styrene maleic anhydride copolymer solution), Sartomer Co.)
poly(methylvinyl ether-maleic acid)
poly(caprolactone)
poly(n-amylmethacrylate)
wood rosin
polyanhydrides, e.g., poly(sebacic anhydride), poly(valeric anhydride), poly(trimethylene carbonate), etc., and copolymers such as poly(carboxyphenoxypropane-sebacic acid), poly(fumaric acid-sebacic acid), etc.
Polyorthoesters
poly(cyanoacrylates)
poly(dioxanone)
ethyl cellulose
ethyl vinyl acetate polymers and copolymers
poly(ethylene glycol)
poly(vinylpyrrolidone)
acetylated mono-, di-, and triglycerides
poly(phosphazene)
chlorinated natural rubber
vinyl polymers and copolymers
polyvinyl chloride
Hydroxyalkylcelluloses
Polybutadiene
Polyurethane
vinylidene chloride polymers and copolymers
styrene-butadiene copolymers
styrene-acrylic copolymers
vinyl acetate polymers and copolymers (e.g., vinyl acetate-ethylene copolymers (VINAMUL® (ethylene-vinyl acetate copolymer) formulation) and vinyl acetate-vinylpyrrolidone copolymers
alkylvinylether polymers and copolymers
cellulose acetate phthalates
ethyl vinyl phthalates
cellulose triacetate
Polyanhydrides
Polyglutamates
polyhydroxy butyrates
acrylic polymers (RHOPLEX® (acrylic polymer emulsions))
alkyl acrylate polymers and copolymers
aryl acrylate polymers and copolymers
aryl methacrylate polymers and copolymers
poly(caprolactams) (i.e., the nitrogen-containing counterparts to caprolactones)
epoxy/polyamine epoxy/polyamides
polyvinyl alcohol polymers and copolymers
silicones
polyesters (for oil-based approaches, including alkyds)
phenolics (polymers and copolymers with drying oils)
Preferred polymers include:
poly(methylmethacrylate)
poly(lactic acid) (CHRONOPOL™ 50, 95, or 100 (poly(lactic acid) formulation)) and combinations with polystyrene
poly(lactic acid-glycolic acid) copolymers (LACTEL® BP 400 (poly(DL-lactide-co-glycolide) formulation))
cellulose acetate butyrate
poly(styrene)

Poly(methylmethacrylate or poly(styrene maleic anhydride copolymer) (or blends comprising one or both of these polymers) are currently preferred for use with triazole fungicides such as tebuconazole, cyproconazole, and epoxiconazole, for example.

It is also contemplated that certain resins such as polyalkyd resins, phenolic resins, abietic acid and epoxy resins will be suitable for the practice of this invention. Also encompassed by the present invention are filled polymer and co-polymer systems, i.e., using calcium carbonate, silica, clay, and the like.

Active Ingredient. The particle of the present invention can include an active ingredient entrapped in a polymeric matrix or a plurality of active ingredients having similar or different activities (e.g., a fungicide and an insecticide). The active ingredient can be, for example, any of various conventional biocides, including a fungicide (e.g., a triazole, an imidazole, a methoxyacrylate, a fungicide in the morpholine series such as fenpropimorph), a herbicide (e.g., glyphosate, phosphinothricin, triallate, alachlor), a insecticide (e.g., an organophosphorus compound, imidacloprid, a pyrethroid), a nematocide, an acaricide, a molluscicide, a nematocide, a rodenticide, a bactericide, and a termiticide; a chemical hybridizing agent (e.g., clofenset potassium); a herbicide safener; a chemical inducer or elicitor (e.g., a protein activator), a plant growth regulator (e.g., an auxin, a cytokinin, or a gibberellin), an elicitor, or a nutrient such as a fertilizer, or a minerals). In addition to an active ingredient, the particle can also include one or more inert ingredients such as a solvent, a dispersant, an adjuvant, or a plasticizer, and can be formulated for example as a liquid, a dispersion, a water soluble granule, a wettable powder, a water dispersible granule, a suspension concentrate, a liquid flowable, an dry flowable, a suspension, a granule, or a seed coating. Triazole fungicides suitable for the practice of this invention are exemplified by bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, and triticonazole. Preferably the triazole fungicide is selected from the group consisting of cyproconazole, epoxiconazole, tebuconazole, triadimefon, and triadimenol. More preferably the triazole fungicide is cyproconazole. A discussion of the properties for some of these fungicides can be found in U.S. Pat. No. 4,664,696, EPA 196038, and U.S. Pat. No. 4,723,984.

Some representative fungicides, herbicides, insecticides, and growth regulators that are useful in the present invention are listed below:

| Fungicides | |
| --- | --- |
| Benomyl | Fludioxonil |
| Benzothiadiazoles | Flutolanil |
| Captan | fosetyl-Al |
| Chlorothalonil | kresoxim-Methyl |
| Cyproconazole | Mancozeb |
| cyprodinil | metalaxyl |
| epoxiconazole | prochloraz |
| fenarimol | triticonazole |
| fenpropimorph | tebuconazole |
| Bitertanol | Vinclozolin |
| Bromuconazole | Difenoconazole |
| Epoxiconazole | Fenbuconazole |
| Fluquinconazole | Flusilazole |
| Flutriafol | Hexaconazole |
| Imibenconazole | Metconazole |
| Myclobutanil | Penconazole |

Fungicides

| | |
|---|---|
| Propiconazole | Tetraconazole |
| Triadimefon | Triadimenol |

Herbicides

Acetochlor
Acifluorfen
Acrolein
Alachlor
Ametryn
Amitrole
Anilofos
Asulam
Atrazine
Benazolin
Benefin
Benfluralin
Bensulfuron
bensulfuron-methyl
Bensulfide
Bentazone
Bifenox
Bromacil
Bromoxynil
Butachlor
Butralin
Butylate
Carfentrazone
carfentrazone-ethyl
Chloramben
Chlordiazon
Chlorflurenol
Chlorimuron
Chlorotoluron
Chloroxuron
Chlorpropham
Chlorsulfuron
Cinmethylin
Clethodim
Clomazone
Clopyralid
Cyanazine
Cycloate
Cinmethylin
2,4-dichlorophenoxyacetic acid
2,4-dichlorophenoxyacetic acid methyl ester
Dalpon
Dazomet
2,4-DB
DCPA
Desmedipham
Diallate
Dicamba
Diclobenil
Dichlormid
Dichlorprop
Diclofop
Diethatyl
Dietholate
Difenzoquat
Dinoseb
Diphenamid
Dipropetryn
Diquat
Diuron
EPTC
Ethalfluralin
Ethofumesate
Fenac
Fenoxaprop

Herbicides fenoxaprop-ethyl
fenuron TCA
Fluazifop
fluazifop-P
Fluchloralin
Flumetsulam
Fluometuron
Fluroglycofen
fluroglycofen-ethyl
Flurazole
flurenol-butyl
Fluridone
Fomesafen
Fosamine
Glufosinate
Glyphosate
Haloxyfop
Halosulfuron
halosulfuron-methyl
Hexazinone
Imazameth
imazamethazenz
imazamethabenz-methyl
Imazapyr
Imazaquin
Imazethapyr
Ioxynil
Isopropalin
Isoproturon
Isoxaben
lactofen
Linuron
MAA
MCPA
MCPB
Mecoprop
Mefenacet
Mefluidide
Metham
Methazole
Metolachlor
Metribuzin
Metsulfuron
MH
Molinate
Monolinuron
MSMA
Naproanilide
Napropamide
Naptalam
Neburon
Nicosulfuron
Norea
Norflurazon
Orbencarb
Oryzalin
Oxadiazon
Oxyfluorfen
Paraquat
Pebulate
pelargonic acid
Pendimethalin
phenmedipham
Picloram
Primisulfuron
Prodiamine
Prometon
Prometryn
Pronamide
Propachlor
Propanil
Propazine
Propham
Pyrazon
pyrazosulfuron
pyrazosulfuron-ethyl
Pyridate -continued

Herbicides

Quizalofop
quizalofop-ethyl
Rimsulfuron
Sethoxydim
Siduron
Simazine
Simetryn
Sulfometuron
Tebuthiuron
Terbacil
Terbuthylazine
Terbumeton
Terbutryn
Thifensulfuron
Thiobencarb
Triallate
Triasulfuron
Triclopyr
Trifluralin
Vernolate

Insecticides and Nematicides

| | |
|---|---|
| Aldicarb | Fenvalerate |
| azinphos-methyl | Imidachloprid |
| Carbaryl | Lindane |
| Carbofuran | Malathion |
| Chlorpyrifos | methyl Parathion |
| Cyfluthrin | Monocrotophos |
| Diazinon | Oftanol |
| Dicofol | Oxamyl |
| Disulfoton | Parathion |
| Endosulfan | Propoxur |
| Fenamiphos | Pyrethrins |

Growth Regulators

| | |
|---|---|
| 6-benzyladenine | Endothall |
| alpha-naphthylactic acid | Ethepon |
| Ancymidol | gibberellic acid |
| Chlorpropham | maleic Hydrazine |
| Daminozide | Paclobutrazol |

Chemical Hybridizing Agents clofenset (K+ salt)

Accordingly, in one embodiment the present invention comprises a particle comprising a triazole fungicide in a polymer matrix. For example, the triazole fungicide can comprise a compound selected from the group consisting of bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, and triticonazole. Preferably the triazole fungicide comprises a compound selected from the group consisting of cyproconazole, epoxiconazole, tebuconazole, triadimefon, and triadimenol. The polymer matrix can comprise a polymer selected from the group consisting of poly(methylmethacrylate), poly(lactic acid), a poly(lactic acid-glycolic acid) copolymer, cellulose acetate butyrate, a poly(styrene), hydroxybutyric acid-hydroxyvaleric acid copolymer, a styrene maleic anhydride copolymer, poly(methylvinyl ether-maleic acid), poly(caprolactone), poly(n-amylmethacrylate), wood rosin, a polyanhydride, a polyorthoester, a poly(cyanoacrylate), poly(dioxanone), ethyl cellulose, a ethyl vinyl acetate polymer, poly (ethylene glycol), poly(vinylpyrrolidone), an acetylated monogylceride, an acetylated digylceride, an acetylated trigylceride, poly(phosphazene), chlorinated natural rubber, a vinyl polymer, polyvinyl chloride, a hydroxyalkylcellulose, polybutadiene, polyurethane, a vinylidene chloride polymer, a styrene-butadiene copolymer, a styrene-acrylic copolymer, an alkylvinylether polymer, a cellulose acetate phthalate, an ethyl vinyl phthalate, cellulose triacetate, a polyanhydride, a polyglutamate, a polyhydroxy butyrate, polyvinyl acetate, a vinyl acetate-ethylene copolymer, a vinyl acetate-vinylpyrrolidone copolymer, an acrylic polymer, an alkyl acrylate polymer, an aryl acrylate polymer, an aryl methacrylate polymer, a poly(caprolactam), an epoxy resin, a polyamine epoxy resin, a polyamide, a polyvinyl alcohol polymer, a polyalkyd resin, a phenolic resin, an abietic acid resin, a silicone, a polyalkylene oxide, and a polyester.

The particle of the present invention can further comprise other ingredients including inert ingredients. For example, the inventive particle can comprise a plasticizer.

The present invention can comprise a particle having a variety of diameters or average diameters. For example, the mean diameter of the particle can be in the range of from about 0.1 microns to about 200 microns, preferably from about 0.2 microns to about 100 microns, and more preferably from about 0.5 microns to about 50 microns.

Release of Active Ingredient from the Particle. The particle according to the present invention can release an agricultural chemical in a controlled fashion by diffusion (e.g., in the case of a particle having a polymer matrix comprising poly(methylmethacrylate or poly(styrene maleic anhydride copolymer) or by disintegration or dissolution of the matrix (e.g., in the case of a particle having a polymer matrix comprising polylactic acid polymers), depending on the matrix polymer employed. Release rates also vary with the size of particles (i.e., release rates vary as a function of the surface area/volume ratio of the particle). The matrix material can be selected to have properties conducive to the appropriate release and action of the agriculturally active ingredient in space and time. A particle can also be prepared such that the active ingredient varies in concentration from the outer surface of the matrix particle to its core, providing "programmed" rates and levels of active release over the duration of the seed germination and subsequent growth periods.

The rate of release of an active ingredient from a particle according to the present invention depends on the polymer, size of the particle, the loading of the active ingredient, and the dispersing agent used, if any. The manner in which an active ingredient can be released from a particle depends on whether the loaded active ingredient is suspended or dissolved in the matrix. The steps involved when the active ingredient is dissolved in the matrix material include: diffusion of the active ingredient to the surface of the matrix; partition of the active ingredient between the matrix and the environment or elution medium (e.g., soil water, seed coat, or foliar surface); and transport away from the particle surface. In addition, if the active ingredient is dispersed (for example, as multimolecular pockets of active ingredient in the particle), the active ingredient may have to dissolve into the matrix material before diffusion to the surface.

Another mode of release of the active ingredient can be by biodegradation or erosion of the matrix material, the rate of which can be influenced by the hydrophobicity or hydrophilicity of the polymer, the morphology of the particle, and the chemical nature of the polymer comprising the matrix for example. In addition, the active ingredient can be released by swelling of the polymer matrix after imbibition of a liquid such as water. In diffusion-controlled systems the matrix may be unaffected by swelling, but in swelling-controlled systems the polymer matrix may undergo a transition from a glassy state to a gel state upon interaction with the penetrating solvent. In such cases, release rate can be a function of the glass-to-gel transition process.

Another factor affecting release rate is osmotic pressure, which can be created inside the particle if the active ingredient or polymer has an affinity for the environment external to the particle. The active ingredient is released when the osmotic pressure exceeds the maximum force that the matrix of the particle can tolerate.

Mathematical models for these release mechanisms are described in the following individual references:

U. Pothakamury and G. Barbosa-Canovas, *Trends in Food Science & Technology* 6:397-406, 1995.

R. Langer and N. Peppas, *JMS-Rev. Macromol. Chem. Phys*. C(23):61-126, 1983.

Formulations Including the Particle. The particle according to the invention can be used according to any conventional formulation, including but not limited to: a suspension or slurry of particles in an aqueous medium (e.g., water) at a concentration of active ingredient of from about 0.5% to 99%, preferably 5-40% based on the weight of the particle, for storage and shipping; wettable powders, wettable granules (dry flowable), and dry granules. If formulated as a suspension or slurry, the concentration of the active ingredient in the formulation is preferably about 0.5% to about 99% by weight (w/w), preferably 5-40%.

Other conventional inactive or inert ingredients can be incorporated into the particle or in aqueous media used for producing suspensions of the particle according to the present invention. Such inert ingredients include but are not limited to: conventional sticking agents, dispersing agents such as methylcellulose (METHOCEL® A15LV (methylcellulose formulation) or METHOCEL® A15C (methylcellulose formulation), for example, serve as combined dispersant/sticking agents for use in seed treatments), polyvinyl alcohol (e.g., ELVANOL® 51-05 (partially hydrolyzed polyvinyl alcohol formulation)), lecithin (e.g., YELKINOL™ P (lecithin formulation)), polymeric dispersants (e.g., polyvinylpyrrolidone/vinyl acetate PVP/VA S-630), thickeners (e.g., clay thickeners such as VAN GEL® B (magnesium aluminum silicate formulation) to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, "Emulsifiers and Detergents," MC Publishing Company, Glen Rock, N.J., U.S.A., 1996. Additional inert ingredients useful in the present invention can be found in McCutcheon's, vol. 2, "Functional Materials," MC Publishing Company, Glen Rock, N.J., U.S.A., 1996.

Formulations according to the present invention can be applied by any conventional method, including but not limited to: (1) direct injection into the soil around seeds or in the root zone of developing plants, for example, at a point 2 cm deep and within a 3 cm radius of the plant crown; (2) application as a soil drench; (3) application as a foliar spray; and (4) application as a seed treatment.

Particles according to the present invention can be applied to seeds by any standard seed treatment methodology, including but not limited to mixing in a container (e.g., a bottle or bag), mechanical application, tumbling, spraying, and immersion. Any conventional active or inert material can be used for coating seeds with particles according to the present invention, such as conventional film-coating materials including but not limited to water-based film coating materials such as SEPIRET® (cellulose binder formulation) (Seppic, Inc., Fairfield, N.J.) and OPACOAT® (color coating composition) (Berwind Pharm. Services, Westpoint, Pa.).

The formulated product, when used as a suspension in an aqueous carrier, preferably comprises a dispersing agent to permit a relatively uniform or homogeneous mixture to form. The dispersing agent preferably also provides a degree of "tackiness" or adhesion to the particle formulation in order for the formulation to adhere to treated seeds or other foliar surfaces. Suitable dispersing agents include but are not limited to aqueous 0.25-1.0% poly(vinyl alcohol), such as ELVANOL® 51-05 (partially hydrolyzed polyvinyl alcohol formulation) (DuPont) and METHOCEL® A15LV (methylcellulose formulation).

One embodiment of the present invention provides a fungicidal composition comprising a particle comprising a triazole fungicide in a polymer matrix, and an agricultural adjuvant. The composition can take a variety of forms, including a liquid suspension, a wettable powder, a granule, a water-dispersible granule, a suspension concentrate, or the like. Preferably, the fungicidal composition comprises a dispersant. The fungicidal composition also preferably comprises an adjuvant. The fungicidal composition can also comprise a diluent. The diluent can be either a solid or a liquid diluent. Solid diluents can include, for example, silica, alumina, cellulose, methylcellulose, clay, or a polymer. Liquid diluents can include, for example, water, an organic solvent, or an inorganic solvent.

Methods of producing matrix particles. The matrix particles of the present invention can be produced by any process that results in a polymer matrix having active ingredients substantially uniformly distributed therein, including but not limited to solvent evaporation, solvent partition, hot melt microencapsulation, coacervation, emulsion polymerization, interfacial polycondensation, and spray drying.

A preferred process for entrapping the agriculturally active ingredient in accordance with the present invention includes the following steps:

(A) Preparation of a hydrophobic solution ("oil phase") including an active ingredient and a polymer in an organic solvent;

(B) Preparation of a hydrophilic solution ("aqueous phase") by dissolving a dispersing agent in water (or an aqueous or alcoholic solution);

(C) Forming an emulsion by combining the hydrophobic solution with the hydrophilic solution with stirring, homogenization, or sonication;

(D) Stirring the emulsion formed in (C) until all of the organic solvent has evaporated. The organic solvent can alternatively or additionally be removed at reduced pressure using a rotary evaporator; and (E) Optionally isolating the matrix particles by allowing the evaporated emulsion formed in (D) to settle, decanting the supernatant liquid from the matrix particles, then washing, filtering, and drying the particles in air.

The particles can be resuspended in an aqueous carrier system comprising water and, for example, a dispersing agent, dye or colorant, or other inert ingredient. The particles can alternatively be used without isolation.

Specifically, the matrix particle preparation process can be carried out by dissolving the agriculturally active ingredient and the polymer in an amount of organic solvent sufficient to form the hydrophobic solution. This dissolution is performed at room temperature or at temperatures not greater than 50° C. with mechanical stirring. For microencapsulating active ingredients according to this general process, it is preferred that the active ingredient be preferentially soluble in the hydrophobic phase rather than in the hydrophilic phase, and preferably substantially insoluble in the aqueous phase (by substantially insoluble is meant a solubility of less than 1% by weight in water at 25° C.). A dispersing agent can then be dissolved in a quantity of deionized water sufficient to form the hydrophilic solution. This dissolution is performed at room temperature with mechanical stirring. The hydrophobic solution is then poured into the hydrophilic solution, while stirring, homogenizing, or sonicating the hydrophilic solution vigorously to form an emulsion, or by any other method conventionally used in the emulsification art. The emulsion comprises microdroplets from the hydrophobic solution that are uniformly dispersed and suspended in the hydrophilic solution. The droplet size and the final size of the matrix particle is controlled by shear rate and degree of agitation, the temperature, the volumetric ratio of the dispersed hydrophobic phase to continuous aqueous phase, and the type of dispersing agent used, if any. Stirring of the emulsion can be continued until all of the organic solvent is evaporated. Once the organic solvent has evaporated, the supernatant liquid can be decanted and the matrix particles can be washed, filtered, and dried or used, preferably as is.

In the process outlined above, the organic solvent used to prepare the hydrophobic solution should be suitable for co-dissolving the required amounts of the active and polymer to form a hydrophobic (water-immiscible) solution. The organic solvent should not otherwise interact with or alter the intended functions of the active or polymer in the prepared matrix particles. The organic solvent should also have adequate volatility at room temperature (sufficiently low boiling point at ambient pressures) in order to evaporate at a reasonable rate from the emulsion. The solvent in the method of the present invention is preferably a substantially hydrophobic solvent. For example, the solvent can comprise a compound selected from the group consisting of halogenated hydrocarbons, aromatic compounds, hydrocarbons, ethers, and esters. Methylene chloride is an example of an organic solvent suitable for the practice of this invention. Other suitable organic solvents include but are not limited to ethyl acetate, chloroform, carbon tetrachloride, acetonitrile, diethyl ether, dimethyl ether, acetone, methylethylketone, pentane, hexane, hexanes, heptane, dioxane, ethanol, methanol, pyridine, propanol, 2-propanol, butanol, 2-butanol, t-butyl alcohol, isobutyl alcohol, perchloroethylene, tetrachloroethane, o-xylene, m-xylene, p-xylene, toluene, benzene, mesitylene, chlorobenzene, o-dichlorobenzene, m-dichlorobenzene, p-dichlorobenzene, or any other organic solvent which is chemically unreactive under the particle-forming conditions and which is capable of being evaporated under temperature or pressure conditions under which the particle of the present invention is stable. Preferably the solvent comprises a compound selected from the group consisting of methylene chloride, o-xylene, m-xylene, p-xylene, toluene, and chlorobenzene. More preferably the solvent comprises methylene chloride. The amount of organic solvent useful in forming the hydrophobic solution ranges from about two to about eight times, and preferably about three times, the weight of the polymer (or of the combined weight of the polymer and the active).

In general, no adjustment of the pH of the system is required during the matrix particle process to achieve satisfactory performance and production of entrapped material.

A preferred process for producing matrix particle of the present invention utilizes solvent evaporation. Briefly, the solvent evaporation technique involves mixing a hydrophobic liquid medium and a hydrophilic liquid medium to produce an emulsion. An emulsion can be made with a hydrophobic phase in a hydrophilic phase (e.g., oil-in-water) or with a hydrophilic phase in a hydrophobic phase (e.g., water-in-oil); the former is currently preferred. Moreover, it is preferred to produce an emulsion in which the volume of the hydrophilic phase is significant excess to the volume of the hydrophobic phase. An active ingredient can be added that preferentially dissolves in the hydrophobic phase, and preferably is substantially insoluble in the hydrophilic phase. The shear rate and time period for mixing the hydrophobic and hydrophilic phases is selected so as to produce uniformly dispersed hydrophobic droplets having average diameters in the range from about 0.2 to 200 microns, preferably from about 1 to about 50 microns. The solvent is then evaporated from the hydrophobic phase, producing matrix particles of the present invention.

In the solvent partition technique, an active ingredient is dissolved or dispersed in a volatile organic solvent. The resulting solution is suspended as a fine dispersion in an organic oil into which the organic solvent is extracted to produce particles. This technique can be carried out at room temperature and does not require water. As one example, a polymer is dissolved in methylene chloride, the required amount of an active ingredient (e.g., a fungicide) is added, and the mixture is suspended in silicone oil containing a nonionic emulsifier such as Span 85 and additional methylene chloride. After adding the polymer solution to the silicone oil, petroleum ether is added and the mixture is stirred until the matrixed particles have hardened. The particles can be removed by filtration or centrifugation, washed with petroleum ether, and dried under vacuum. Examples of the solvent partition technique are provided in R. Langer et al., *Polymer* 31:547-555, 1990. Further examples of the solvent partition technique are provided in *Kirk-Othmer Encyclopedia of Chemical Technology*, fourth edition, vol. 16, Curt Thies.

In hot melt microencapsulation;, a polymer melt is mixed with the active ingredient, which can be suspended or dissolved therein. The resulting mixture is suspended in a non-miscible solvent (for example, silicone oil or olive oil) that is heated about 5° C. above the melting point of the polymer while stirring continuously. After an emulsion is formed and stabilized, it is cooled until the particles are solidified. After cooling, the particles are washed by decantation with petroleum ether to produce a free-flowing powder. In general, the resulting particles are less than about 50 microns in diameter. Examples of the hot melt microencapsulation technique are provided in E. Mathiowitz and R. Langer, *J. Contr. Rel.* 5:13-22, 1987. Further examples of the hot melt microencapsulation technique are provided in *Microcapsules and Nanoparticles in Medicine and Pharmacy*, ed. M. Donbrow, CRC Press, 1992, pp. 105-107.

In one embodiment, the present invention provides a method of producing a particle wherein the particle comprises a triazole fungicide in a polymer matrix comprising providing a hydrophobic solution comprising a triazole fungicide, a polymer, and a solvent; mixing the hydrophobic solution and an aqueous medium to produce a dispersion of droplets of the hydrophobic solution in the aqueous medium; and evaporating the solvent from the dispersion to produce a particle comprising a triazole fungicide in a polymer matrix.

Preferably the fungicide is a triazole fungicide such as bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, or triticonazole. More preferably the fungicide is selected from the group consisting of cyproconazole, epoxiconazole, tebuconazole, triadimefon, and triadimenol.

Preferably the polymer is selected from the group consisting of polystyrene-maleic anhydride copolymer or polymethylmethacrylate. The hydrophobic solution of the present method can comprise a dispersing agent.

The hydrophilic solution in the method of the present invention can also comprise a dispersing agent. Preferably the dispersing agent in the hydrophilic solution is methyl cellulose or polyvinyl alcohol.

The solvent evaporation step of the method of the present invention can comprise applying vacuum, heat, or a combination of vacuum and heat to the dispersion. Alternatively, the solvent evaporation step can comprise lyophilizing the dispersion.

Application of matrix particles to soil, seed, or plant. The particle and formulation composition of the present invention can be applied to the soil, where the active ingredient can be released and eventually affect a target pest either directly or indirectly. For example, the active ingredient can be taken up by a plant, or taken up by or distributed to a part of which is ingested or infested by the pest.

The particle formulation can be applied by any conventional method, including but not limited to: (1) injection of a formulation (e.g., an aqueous suspension of particles) directly into the soil around seeds or in the root zone of developing plants (e.g., injection at a point 2 cm deep and within a 3 cm radius of the plant crown; (2) application as a soil drench to the point at which the soil is at field capacity; (3) application as a foliar spray, preferably in a sufficient volume to thoroughly wet the foliage; and (4) application directly to seeds (i.e., seed treatment). Release of the active ingredient from the particle will provide a desired biological effect in the zone of application or upon uptake of the active ingredient by the plant.

A particle or formulation of the present invention can be applied to seed by any standard seed treatment methodology, for example, by using a Hege 11 Liquid Seed Dresser.

Matrix particles of the present invention can be applied in combination with another active ingredient that is provided as fast- or slow-release formulations. Slow-release matrix particles according to the present invention can also be applied together with a fast-release formulation having the same active ingredient (or with a particle comprising the same active ingredient) in order to achieve, for example, a chemical application regime with an initial high rate of release followed by a slower rate of release over a longer period of time.

The treatment method of the present invention provides, for example a method for the treatment or prophylaxis of a fungal disease in a target plant wherein the method comprises contacting a plant cell, a plant tissue, or a seed with a particle wherein the particle comprises a triazole fungicide in a polymer matrix. Preferably the treatment method comprises contacting a seed with the particle of the present invention. Preferably the contacting is performed before the seed is planted. Preferably the triazole fungicide is selected from the group consisting of bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, and triticonazole. More preferably the fungicidal agent is selected from the group consisting of cyproconazole, epoxiconazole, tebuconazole, triadimefon, and triadimenol.

The polymer matrix useful in the treatment method of the present invention preferably comprises a polymer selected from the group consisting of poly(methylmethacrylate), poly(lactic acid), a poly(lactic acid-glycolic acid) copolymer, cellulose acetate butyrate, a poly(styrene), hydroxybutyric acid-hydroxyvaleric acid copolymer, a styrene maleic anhydride copolymer, poly(methylvinyl ether-maleic acid), poly(caprolactone), poly(n-amylmethacrylate), wood rosin, a polyanhydride, a polyorthoester, a poly(cyanoacrylate), poly(dioxanone), ethyl cellulose, a ethyl vinyl acetate polymer, poly(ethylene glycol), poly(vinylpyrrolidone), an acetylated monogylceride, an acetylated digylceride, an acetylated trigylceride, poly(phosphazene), chlorinated natural rubber, a vinyl polymer, polyvinyl chloride, a hydroxyalkylcellulose, polybutadiene, polyurethane, a vinylidene chloride polymer, a styrene-butadiene copolymer, a styrene-acrylic copolymer, an alkylvinylether polymer, a cellulose acetate phthalate, an ethyl vinyl phthalate, cellulose triacetate, a polyanhydride, a polyglutamate, a polyhydroxy butyrate, polyvinyl acetate, a vinyl acetate-ethylene copolymer, a vinyl acetate-vinylpyrrolidone copolymer, an acrylic polymer, an alkyl acrylate polymer, an aryl acrylate polymer, an aryl methacrylate polymer, a poly(caprolactam), an epoxy resin, a polyamine epoxy resin, a polyamide, a polyvinyl alcohol polymer, a polyalkyd resin, a phenolic resin, an abietic acid resin, a silicone, a polyalkylene oxide, and a polyester.

Preferably after the contacting step, the health of the target plant is substantially similar to the health of a control plant which is substantially free of the fungal disease and which is free of contact with the triazole fungicide. Alternatively, the health of the target plant after the contacting step is intermediate between the health of a first control plant which is substantially free of the fungal disease and which is free of contact with the triazole fungicide, and the health of a second control plant which is substantially free of the fungal disease and which is contacted with the triazole fungicide in the absence of the polymer matrix.

EXAMPLES

Example 1

3.72 g of cyproconazole (96.3% purity; Sandoz Agro, Ltd., Basel, Switzerland) and 14.3 g of polylactic acid (CHRONOPOL™ 95 (poly(lactic acid) formulation); CHRONOPOL™ (poly(lactic acid) formulation), Golden, Colo.) were dissolved in 156 g methylene chloride (Burdick & Jackson, Muskegon, Mich.) in a glass bottle with shaking to produce a hydrophobic solution.

7.5 g of polyvinyl alcohol (ELVANOL® 51-05 (partially hydrolyzed polyvinyl alcohol formulation); DuPont, Wilmington, Del.)) was dissolved with stirring in deionized water to produce 1500 g of hydrophilic solution.

The hydrophobic solution was added to the hydrophilic solution and the mixture was vigorously stirred to produce an emulsion. The stirring continued for one hour. Microscopic examination of the appearance and size of the oil droplets in the emulsion showed that the average size of oil droplets was in the 30-50 micrometer (micron, µ) range.

The emulsion was then transferred to a two liter (L) round bottom flank and attached to a rotary evaporator to remove the methylene chloride at a reduced pressure. The final methylene chloride residue was removed by heating the flask in a hot water bath at 40° C. while on the evaporator.

The resulting particle suspension was filtered on a Buechner funnel to produce a filter cake, which was washed with three portions of deionized water to remove the last traces of aqueous filtrate. The filter cake was then air dried by spreading the product out on a sheet of clean paper.

An aqueous carrier solution was prepared by dissolving urea (Fischer Scientific, Pittsburgh, Pa.) and METHOCEL® A15LV (methylcellulose formulation) (Dow Chemical Co., Midland, Mich.) in water by stirring. Urea was added as an anti-freeze and METHOCEL® A15LV (methylcellulose formulation) as a combined dispersant and non-phytotoxic sticking agent for use in seed treatments. (A clay thickener such as VAN GEL® B (magnesium aluminum silicate formulation) (R.T. Vanderbilt Co., Inc., Norwalk, Conn.) are optionally added to the aqueous carrier solution to improve viscosity and reduce settling.) The dry microcapsules were stirred into the aqueous carrier solution to produce a homogenous suspension.

The composition of the final formulation (Formulation 1) is shown below.

Formulation 1

| Ingredients | % w/w | Weight (g) | Active Ingredient ("a.i.") |
|---|---|---|---|
| Cyproconazole (19.88%) | 17.72 | 37.32 | 7.42 g (% a.i. (w/w) = 3.52) |
| Urea | 4.49 | 9.46 | |
| Methocel ® A15LV (methylcellulose formulation) | 0.05 | 1.05 | |
| Water, deionized | 77.29 | 162.79 | |
| Total | 100.00% | 210.62 | % polymer (w/w) = 14.2 |

Example 2

1.56 g cyproconazole (96.3% purity) and 13.44 g cellulose acetate butyrate polymer (Sigma Chemical Co., St. Louis, Mo.) were dissolved in 82.22 g methylene chloride in a glass bottle with shaking to produce a hydrophobic solution. 1.00 g of METHOCEL® A15LV (methylcellulose formulation) and 20 g of urea were dissolved in 64 g deionized water to prepare 85 g of a hydrophilic solution. The hydrophobic solution was added to the hydrophilic solution with stirring to produce an emulsion. The emulsion was stirred for 5 minutes to equilibrate. To reduce the particle size further, the emulsion was sonicated for 5.5 minutes with a sonic dismembrator (Model 550, Fischer Scientific, Pittsburgh, Pa.) using a variable power range. Cooling was provided by an ice bath to keep the temperature below 30° C. Microscopic examination showed particles mainly in the 4-5 micron range. The emulsion was transferred to a rotary evaporator and methylene chloride stripped off as described in Example 1. The resulting product was passed through a #325 mesh sieve to remove foreign particles and assayed for particle size, density (at room temperature), and % active ingredient.

The following were the properties of the matrix particles (Formulation 2):

| Formulation 2 - Properties | |
|---|---|
| % active ingredient (w/w) | 1.72 |
| Density, g/mL | 1.11 |
| Ave. particle size, μ | 4.4 |

Example 3

Following the general procedure of Example 2, matrix particle suspensions having the compositions given below were produced. For Formulation 3, methylene chloride was evaporated with stirring at atmospheric pressure. For Formulation 4, Formulation 5, Formulation 6, and Formulation 7, methylene chloride was evaporated with a rotary evaporator at reduced pressure. For Formulation 7, VAN GEL® B (magnesium aluminum silicate formulation) was added as part of the aqueous carrier medium. Poly(methylmethacrylate) (PMM) and polystyrene (50,000 MW) were obtained from Polysciences Inc. (Warrington, Pa.)

| | Weight % of Ingredients Formulation Number | | | | |
|---|---|---|---|---|---|
| Ingredients | 3 | 4 | 5 | 6 | 7 |
| Cyproconazole* | 1.50 | 1.50 | 3.00 | 3.00 | 3.00 |
| CHRONOPOL ™ 95 (poly(lactic acid) formulation) | 13.50 | 13.50 | — | — | — |
| PMM | — | — | 6.00 | 12.00 | 6.00 |
| Polystyrene | — | — | 6.00 | — | 6.00 |
| METHOCEL ® A15LV (methylcellulose formulation) | 1.00 | 1.00 | 1.06 | 1.06 | — |
| Urea | 20.00 | 20.00 | — | — | — |
| VAN GEL ® B (magnesium aluminum silcate formulation) | — | — | — | — | 3.40 |
| Water | 64.00 | 64.00 | 83.94 | 83.94 | 81.60 |
| Total | 100.00 | 100.00 | 100.00 | 100.00 | 100.00 |

*100% a.i. basis. Compensate for purity with polymer.

The matrix particle suspensions had the following properties:

| | Formulation | | | | |
|---|---|---|---|---|---|
| Properties | 3 | 4 | 5 | 6 | 7 |
| Density R.T., g/mL | 1.10 | 1.12 | 1.02 | 1.04 | 1.02 |
| Ave. particle size, μm | 1.18 | 2.52 | 1.84 | 1.13 | 138.50 |
| Viscosity* at room temperature, cps | spindle # 18 | spindle # 18 | spindle # 18 | spindle # 18 | spindle # 31 |
| R.P.M. - 60 | 11.30 | 27.90 | 9.52 | 16.70 | 185 |
| R.P.M. - 30 | 12.40 | 28.60 | 9.92 | 17.00 | 329 |

-continued

| | Formulation | | | | |
|---|---|---|---|---|---|
| Properties | 3 | 4 | 5 | 6 | 7 |
| R.P.M. - 12 | 15.50 | 32.60 | 11.00 | 17.00 | 765 |
| R.P.M. - 6 | 22.00 | 36.10 | 13.50 | 21.00 | 1520 |

*Viscosity in centipoise (cps) was determined using a Brookfield viscometer (model LVT, Brookfield Engineering Laboratories, Stoughton, MA) according to manufacturer instructions).

Example 4

Following the general procedure of Example 2, matrix particle suspensions having the compositions given below were produced:

| | Weight % of Ingredients Formulation | | |
|---|---|---|---|
| Ingredients | 5 | 8 | 9 |
| Cyproconazole* | 3.00 | 3.00 | 3.00 |
| CHRONOPOL ® 95 (poly(lactic acid) formulation) | — | — | 6.00 |
| PMM | 6.00 | 6.00 | — |
| Polystyrene | 6.00 | 6.00 | 6.00 |
| METHOCEL ® A15LV (methylcellulose formulation) | 1.06 | 1.00 | 1.00 |
| VAN GEL ® B (magnesium aluminum silicate formulation) | — | 2.06 | 2.06 |
| Water | 83.94 | 81.94 | 83.94 |
| Total | 100.00 | 100.00 | 100.00 |

*100% a.i. basis. Compensate for purity with polymer.

The matrix particle suspensions were analyzed for the following properties:

| | Formulation | | |
|---|---|---|---|
| Properties | 5 | 8 | 9 |
| Density, R.T., g/mL | 1.02 | 1.04 | 1.04 |
| Ave. particle size, µ | 1.84 | 2.06 | 6.15 |
| Viscosity at room temperature, cps | spindle # 18 | spindle # 18 | spindle # 18 |
| R.P.M.* - 60 | 9.52 | 22.70 | 21.70 |
| R.P.M.* - 30 | 9.92 | 26.20 | 22.90 |
| R.P.M.* - 12 | 11.00 | 34.60 | 25.40 |
| R.P.M.* - 6 | 13.50 | 41.60 | 27.00 |

*Revolutions per minute.

Example 5

Following the general procedure of Example 2, matrix particle suspensions having the compositions given below were produced. The hydrophilic and hydrophobic solutions were sonicated to produce an emulsion for preparation of Formulation 8 and homogenized with a Silverson L4R laboratory homogenizer (Silverson Machines, Inc., East Longmeadow, Mass.) to produce and emulsion for preparation of Formulation 10 and Formulation 11.

| | Weight % of Ingredients Formulation | | |
|---|---|---|---|
| Ingredients | 8 | 10 | 11 |
| Cyproconazole* | 3.00 | 3.00 | 3.00 |
| PMM | 6.00 | 6.00 | 6.00 |
| Polystyrene | 6.00 | 6.00 | 6.00 |
| METHOCEL ® A15LV (methylcellulose formulation) | 1.00 | 1.00 | 1.00 |
| Van Gel ® B (magnesium aluminum silicate formulation) | 2.06 | 2.06 | 3.00 |
| Water | 81.94 | 81.94 | 81.00 |
| Total | 100.00 | 100.00 | 100.00 |

*100% a.i. basis. Compensate for purity with polymer.

The matrix particle suspensions had the following properties:

| | Formulation | | |
|---|---|---|---|
| Properties | 8 | 10 | 11 |
| Density, R.T., g/ml | 1.04 | 1.04 | 1.05 |
| Ave. particle size, µm | 2.06 | 3.55 | 3.20 |
| Viscosity at room temperature, cps | spindle # 18 | spindle # 18 | spindle # 31 |
| R.P.M. - 60 | 22.70 | 47.40 | 192 |
| R.P.M. - 30 | 26.20 | 52.40 | 265 |
| R.P.M. - 12 | 34.60 | 61.80 | 446 |
| R.P.M. - 6 | 41.60 | 74.60 | 685 |

ªGel structure.

Example 6

Following the general procedure of Example 2, matrix particle suspensions having the compositions in the table below were produced. The hydrophilic and hydrophobic solutions were homogenized in a cooling bath in preparing Formulation 12 and Formulation 13, but not in preparing Formulation 10 and Formulation 14.

| | Weight % of Ingredients Formulation | | | |
|---|---|---|---|---|
| Ingredients | 10 | 14 | 12 | 13 |
| Cyproconazole* | 3.00 | 3.00 | 3.00 | 3.00 |
| PMM | 6.00 | 6.00 | 6.00 | 6.00 |
| Polystyrene | 6.00 | 6.00 | 6.00 | 6.00 |
| METHOCEL ® A15LV (methylcellulose formulation) | — | 0.75 | 1.75 | 0.75 |

-continued

| | Weight % of Ingredients Formulation | | | |
|---|---|---|---|---|
| Ingredients | 10 | 14 | 12 | 13 |
| METHOCEL ® A15LV (methylcellulose formulation) | 1.00 | — | — | — |
| VAN GEL ® B (magnesium silicate formulation) | 2.06 | — | — | — |
| Water | 81.94 | 84.25 | 83.25 | 84.25 |
| Total | 100.00 | 100.00 | 100.00 | 100.00 |

*100% a.i. basis. Compensate for purity with polymer

The matrix particle suspensions were analyzed for the following properties:

| | Formulation | | | |
|---|---|---|---|---|
| Properties | 10 | 14 | 12 | 13 |
| Density, R.T., g/mL | 1.04 | 1.02 | 1.02 | 1.03 |
| Ave. particle size, μ | 3.55 | 69.51 | 11.00 | 55.56 |
| Viscosity at room temperature, cps | spindle # 18 | spindle # 31 | spindle # 34 | spindle # 31 |
| R.P.M - 60 | 47.40 | 97.70 | 980 | 82.70 |
| R.P.M - 30 | 52.40 | 101.00 | 1020 | 86.80 |
| R.P.M - 12 | 61.80 | 105.00 | 1060 | 87.70 |
| R.P.M - 6 | 74.60 | 125.00 | 1150 | 95.20 |

Example 7

Following the general procedure of Example 1, matrix particle suspensions having the compositions given below were produced. In the table below, runs designated (a) employed particle preparations that were not filtered, washed and dried after solvent evaporation, runs designated (b) employed particles that had been filtered, washed, and air dried as described in Example 1.

| | Weight % of Ingredients | | | | |
|---|---|---|---|---|---|
| | (b) | (a) | (b) | (a) | (b) |
| | Formulation | | | | |
| Ingredients | 15 | 16 | 17 | 18 | 19 |
| Cyproconazole* | 3.52 | 3.52 | 3.52 | 3.52 | 3.52 |
| Polymer** | 14.22(1) | 13.56(2) | 13.62(2) | 13.56(3) | 14.70(3) |
| Urea | 4.49 | 4.50 | 4.46 | 4.50 | 4.46 |
| METHOCEL ® A15LV (methylcellulose formulation) | 0.50 | 0.50 | 0.47 | 0.50 | 0.49 |
| Water | 77.29 | 77.92 | 77.93 | 77.92 | 76.83 |
| Total | 100.00 | 100.00 | 100.00 | 100.00 | 100.00 |

*100% a.i. basis. Compensate for purity with polymer
**(1) Chronopol 95; (2) cellulose acetate butyrate; (3) poly (methylmethacrylate).

The matrix particle suspension were analyzed for the following properties:

| | Formulation | | | | |
|---|---|---|---|---|---|
| Properties | 15 | 16 | 17 | 18 | 19 |
| % a.i. | 3.19 | 3.62 | 3.47 | 4.41 | 3.53 |
| Ave. particle size, μm | 40.00 | 193.00 | 75.00 | 22.80 | 70.00 |

The formulations produced in this Example were applied to wheat as follows. Wheat seed was weighed out into 50 g batches for each treatment. Stock solutions were prepared by weighing out the formulation and adding deionized water to prepare stock solutions of the high rate for each formulation, then, dilutions were prepared from these stocks to provide various rates of application.

A Hege 11 laboratory scale rotostatic seed treater with a 200-gram small capacity seed treatment drum was used for the seed treatments.

For each treatment, a sample batch of seed was treated with the formulation or with the solvent alone to wet up/dirty the drum as recommended by the manufacturer. This seed sample was then discarded. The treatment was then drawn up into a syringe and slowly applied to a new 50 g batch of seed in the seed treater. As soon as the seed appeared dry (usually about 30-45 seconds), it was transferred into a 1 L plastic beaker. The seed was then transferred to a 4 oz. glass jar for storage. The lid of the jar was left off for several hours to ensure that the seed was totally dry. The treatments were applied in order from the lowest rate to the highest rate for each formulation. After the highest rate for each formulation, the seed treater was thoroughly scrubbed out with absolute ethanol on a paper tissue to prevent contamination of the next formulation. The syringe, funnel and beaker were also rinsed with ethanol. This procedure was repeated for each of the formulations that were tested.

At the end of all the treatments and/or when active ingredients were changed in the course of the same study, we also used an additional step of cleaning with a solution of soap in water and an additional ethanol wipe.

In order to assess the safety of the formulations, wheat seed that had been treated previously with test formulations was seeded in standard 4"-square pots containing sterilized Dupo silt loam soil. Seeding was done at a rate of 12-25 seeds per pot, with four replicate pots of each treatment rate. Seeds were covered with approximately 2 cm of the same soil and incubated under a 12-hour photoperiod, 50% relative humidity at 18° C. Eight to twelve days after planting (DAP), each replicate pot of each treatment was rated for the number of seedlings emerged and the average height of emerged seedlings was estimated. The main indicator of formulation performance was the measure of seedling height relative to untreated control plants (untreated=100%).

The table below shows and FIG. 1 illustrates the safety of these treatments, expressed as the height of germinating wheat at 9 days after planting (DAP) as a percent of the height of untreated controls. For comparison, ALTO® 005LS (cyproconazole formulation) (Sandoz Agro, Ltd., Basel, Switzerland) was included as a standard, fast-release non-matrix formulation liquid seed treatment of cyproconazole.

| Rep. No. | Formulation | Intended Rate (g/100 kg Seed) | Analytical Percent Recovery of Applied | Predicted Rate (g a.i./100 kg seed) | Height of Treated Plant in cm (9 DAP) | Percent of Control Height (9 DAP) |
|---|---|---|---|---|---|---|
| 1-1 | ALTO ® 005LS (cyproconazole formulation) | 1.1 | | | 9.6 | 82 |
| 1-2 | ALTO ® 005LS (cyproconazole formulation) | 4.4 | 98.4 | 4.3296 | 7.5 | 64 |
| 1-3 | ALTO ® 005LS (cyproconazole formulation) | 8.8 | 93.1 | 8.1928 | 6.5 | 55 |
| 1-4 | ALTO ® 005LS (cyproconazole formulation) | 17.6 | 90.5 | 15.928 | 4.0 | 33.5 |
| 1-5 | 15 | 1.1 | | | 10.4 | 88.6 |
| 1-6 | 15 | 4.4 | 75.7 | 3.3308 | 9.0 | 76.5 |
| 1-7 | 15 | 8.8 | 75.6 | 6.6528 | 8.5 | 72.5 |
| 1-8 | 15 | 17.6 | 70.5 | 12.408 | 8.4 | 71.5 |
| 1-9 | 15 | 35.2 | 261 | 91.872 | 3.7 | 31.6 |
| 1-10 | 18 | 1.1 | | | 10.8 | 92 |
| 1-11 | 18 | 4.4 | 79.8 | 3.5112 | 9.4 | 79.8 |
| 1-12 | 18 | 8.8 | 83.6 | 7.3568 | 9.4 | 80.3 |
| 1-13 | 18 | 17.6 | 97 | 17.072 | 8.1 | 68.5 |
| 1-14 | 19 | 1.1 | | | 11.5 | 98 |
| 1-15 | 19 | 4.4 | 66.6 | 2.9304 | 10.2 | 86.9 |
| 1-16 | 19 | 8.8 | 63.2 | 5.5616 | 9.7 | 82.6 |
| 1-17 | 19 | 17.6 | 67 | 11.792 | 8.6 | 73.4 |
| 1-18 | 16 | 1.1 | | | 10.1 | 86.3 |
| 1-19 | 16 | 4.4 | 76.6 | 3.3704 | 10.1 | 85.6 |
| 1-20 | 16 | 8.8 | 67.7 | 5.9576 | 9.3 | 79.2 |
| 1-21 | 16 | 17.6 | 65.1 | 11.4576 | 9.0 | 76.1 |
| 1-22 | 17 | 1.1 | | | 10.5 | 89.2 |
| 1-23 | 17 | 4.4 | 89.8 | 3.9512 | 9.6 | 81.3 |
| 1-24 | 17 | 8.8 | 101 | 8.888 | 8.9 | 75.3 |
| 1-25 | 17 | 17.6 | 90.5 | 15.928 | 8.7 | 73.6 |
| 1-26 | 82 | 1.1 | | | 9.2 | 78.6 |
| 1-27 | 82 | 4.4 | 106.1 | 4.6684 | 8.2 | 69.4 |
| 1-28 | 82 | 8.8 | 101.1 | 8.8968 | 7.0 | 59.4 |
| 1-29 | 82 | 17.6 | 98.4 | 17.3184 | 5.7 | 48 |
| 1-30 | Untreated Check | 0 | | | 9.2 | 100 |

Example 8

Following the general procedure of Example 2, matrix particle suspensions having the following compositions were produced. Cellulose acetate butyrate was obtained from Sigma Chemical Co. (St. Louis, Mo.). SMA® 1440 A Resin (ester/styrene maleic anhydride copolymer solution), an ester/styrene maleic anhydride copolymer, was obtained from Sartomer Co. (West Chester, Pa.). Poly(methyl vinyl ether/maleic acid) was obtained from Sigma Chemical Co. (St. Louis, Mo.).

| Ingredients | Weight % of Ingredients Formulation | | | | |
|---|---|---|---|---|---|
| | 20 | 21 | 22 | 23 | 24 |
| Cyproconazole* | 1.50 | 1.50 | 1.50 | 1.50 | 1.50 |
| Cellulose acetate butyrate | 6.75 | — | — | 6.75 | — |
| SMA ® 1440A | 6.75 | 13.50 | — | — | — |
| Resin (ester/stryene maleic anhydride copolymer solution) | | | | | |
| Wood rosin | — | — | 13.50 | — | — |
| Poly (methyl vinyl ether/maleic acid) | — | — | — | 6.75 | — |
| PMM | — | — | — | — | 13.50 |
| METHOCEL ® A15C (methylcellulose formulation | 1.00 | 1.00 | 1.00 | 1.00 | 1.00 |
| Water | 84.00 | 84.00 | 84.00 | 84.00 | 84.00 |
| Total | 100.00 | 100.00 | 100.00 | 100.00 | 100.00 |

*100% a.i. basis. Compensate for purity with polymer

Figure 2:
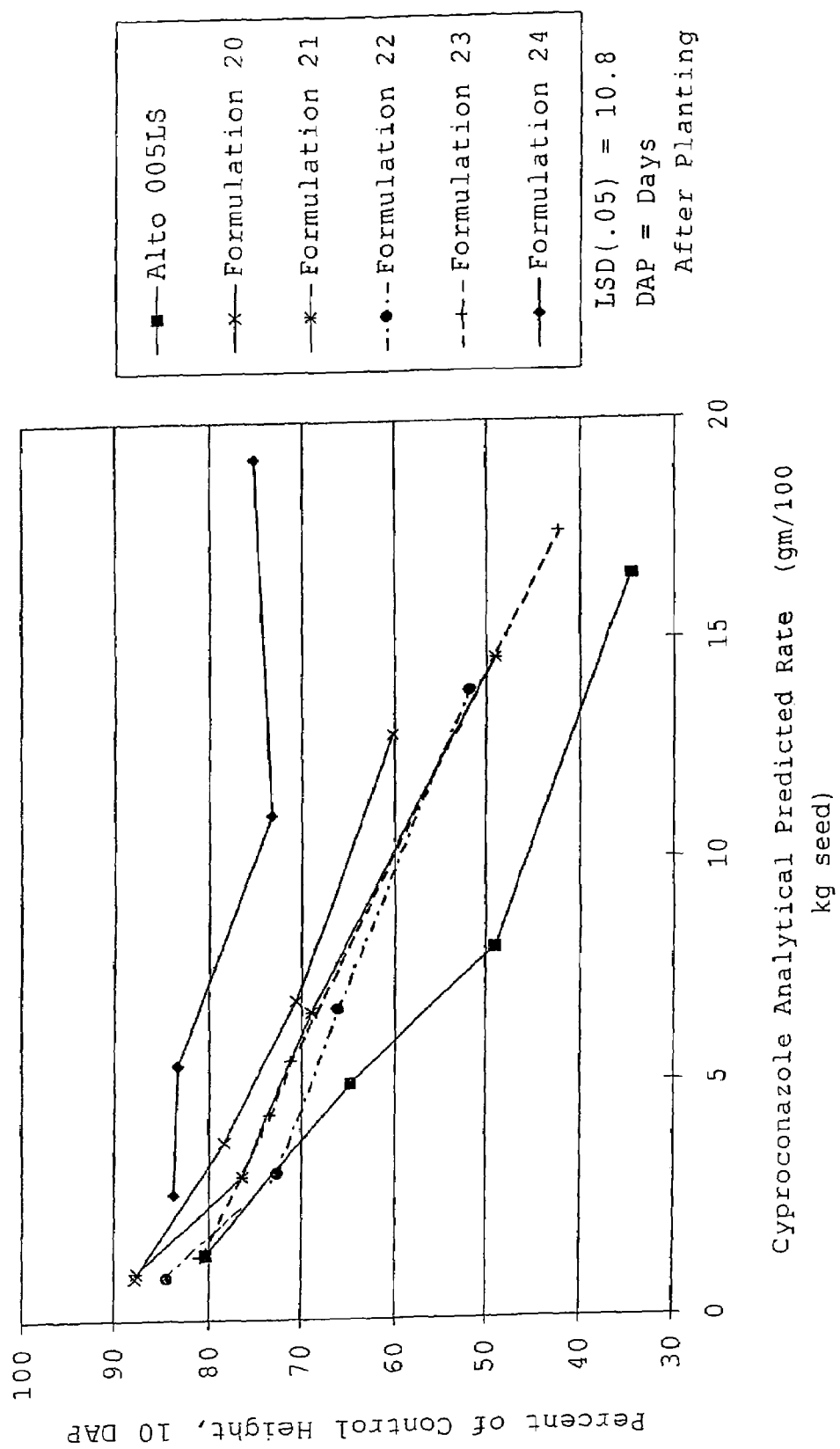
FIG. 2 shows the effect of matrix particle formulations of Example 8 and ALTO® 005LS (cyproconazole formulation) when used as seed treatments on wheat at various rates (g cyproconazole per 100 kg seed), expressed as the height of germinating wheat at 10 DAP as a percent of the height of untreated controls.

The suspensions produced in this Example were applied to wheat using the procedure set forth in Example 7. The table below shows and FIG. 2 illustrates the safety of these treatments at 10 days after planting as compared to ALTO® 005LS (cyproconazole formulation).

| Rep. No. | Formulation | Intended Rate (g/100 kg Seed) | Analytical Percent Recovery of Applied | Predicted Rate (g a.i./100 kg seed) | Height of Treated Plant in cm (9 DAP) | Percent of Control Height (9 DAP) |
|---|---|---|---|---|---|---|
| 2-1 | ALTO ® 005LS (cyproconazole formulation) | 1.1 | 122.7 | 1.35 | 8.2 | 80.4 |
| 2-2 | ALTO ® 005LS (cyproconazole formulation) | 4.4 | 114.1 | 5.02 | 6.6 | 64.9 |
| 2-3 | ALTO ® 005LS (cyproconazole formulation) | 8.8 | 91 | 8.01 | 5.0 | 49.0 |
| 2-4 | ALTO ® 005LS (cyproconazole formulation) | 17.6 | 93.7 | 16.49 | 3.5 | 34.5 |
| 2-5 | 20 | 1.1 | 81.3 | 0.89 | 9.0 | 87.9 |
| 2-6 | 20 | 4.4 | 85.2 | 3.75 | 8.0 | 78.4 |
| 2-7 | 20 | 8.8 | 78.2 | 6.88 | 7.3 | 70.7 |
| 2-8 | 20 | 17.6 | 73.2 | 12.88 | 6.2 | 60.2 |
| 2-9 | 21 | 1.1 | 91.8 | 1.01 | 9.0 | 87.8 |
| 2-10 | 21 | 4.4 | 68.4 | 3.01 | 7.8 | 76.4 |
| 2-11 | 21 | 8.8 | 75.2 | 6.62 | 7.1 | 69.1 |
| 2-12 | 21 | 17.6 | 83 | 14.61 | 5.0 | 49.1 |
| 2-13 | 22 | 1.1 | 80.9 | 0.89 | 8.7 | 84.6 |
| 2-14 | 22 | 4.4 | 70.2 | 3.09 | 7.5 | 72.7 |
| 2-15 | 22 | 8.8 | 76 | 6.69 | 6.8 | 66.2 |
| 2-16 | 22 | 17.6 | 78.9 | 13.89 | 5.3 | 51.9 |
| 2-17 | 23 | 1.1 | 120 | 1.32 | 8.3 | 80.9 |
| 2-18 | 23 | 4.4 | 98.9 | 4.35 | 7.5 | 73.4 |
| 2-19 | 23 | 8.8 | 62.7 | 5.52 | 7.3 | 71.3 |
| 2-20 | 23 | 17.6 | 99.3 | 17.48 | 4.4 | 42.3 |
| 2-21 | 24 | 1.1 | 240 | 2.64 | 8.6 | 83.7 |
| 2-22 | 24 | 4.4 | 124.5 | 5.48 | 8.5 | 83.3 |
| 2-23 | 24 | 8.8 | 126 | 11.09 | 7.5 | 73.3 |
| 2-24 | 24 | 17.6 | 109 | 19.18 | 7.7 | 75.3 |
| 2-25 | Untreated Check | 0 | 0 | | 10.3 | 100.0 |

Example 9

Following the general procedure of Example 1, matrix particle suspensions having the following compositions were produced. LACTEL® BP 400 (poly(DL-lactide-co-glycolide) formulation) was obtained from Sigmal Chemical Co. (St. Louis, Mo.).

| Ingredients | Weight % of Ingredients Formulations | |
|---|---|---|
| | 25 | 26 |
| Cyproconazole* | 3.0 | 3.0 |
| LACTEL ® BP-400 (poly(DL-lactide-co-glycolide) formulation | — | 12.0 |
| Cellulose acetate butyrate | 12.0 | — |
| METHOCEL ® A15LV (methylcellulose formulation | 1.0 | 1.0 |
| Water | 84.0 | 84.0 |
| Total | 100.0 | 100.0 |

*100% a.i. basis. Compensate for purity with polymer.

Figure 3:
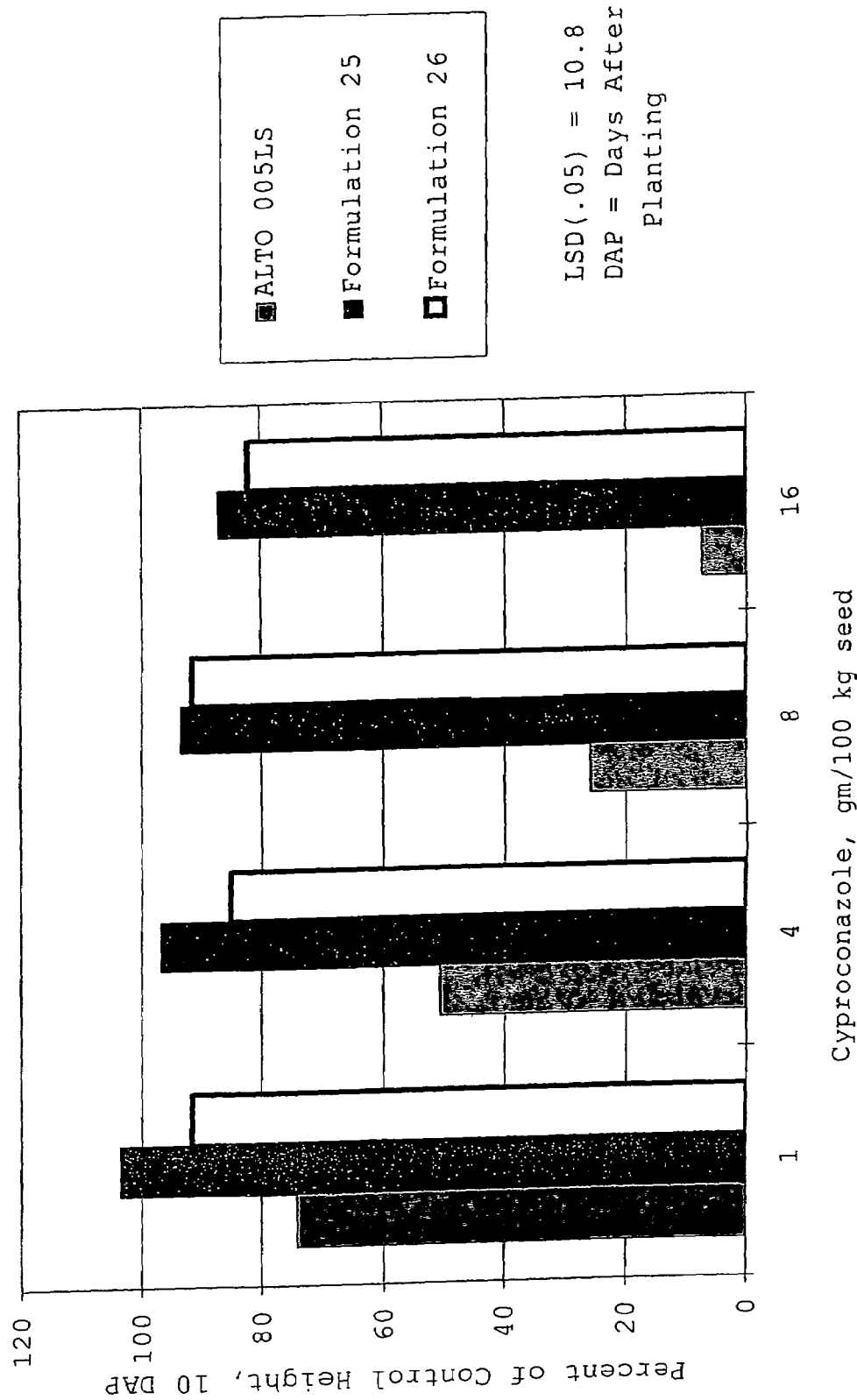
FIG. 3 shows the effect of matrix particle formulations of Example 9 and ALTO® 005LS (cyproconazole formulation) when used as seed treatments on wheat at various rates (g cyproconazole per 100 kg seed), expressed as the height of germinating wheat at 10 DAP as a percent of the height of untreated controls.

The suspensions produced in this Example were applied to wheat using the procedure set forth in Example 7. The table below shows and FIG. 3 illustrates the safety of these treatments at 10 days after planting as compared to ALTO® 005LS (cyproconazole formulation).

| Rep. No. | Rate (g a.i./100 kg seed) | Formulation | Height of Treated Plant in cm (10 DAP) | Percent of Control Height (10 DAP) |
|---|---|---|---|---|
| 3-1 | 1 | ALTO 005LS | 7.88 | 74.4 |
| 3-2 | 4 | ALTO ® 005LS (cyproconazole formulation) | 5.33 | 50.4 |
| 3-3 | 8 | ALTO ® 005LS (cyproconazole formulation) | 2.75 | 26.0 |
| 3-4 | 16 | ALTO ® 005LS (cyproconazole formulation) | 0.83 | 7.8 |
| 3-5 | 1 | 25 | 10.95 | 103.7 |
| 3-6 | 4 | 25 | 10.25 | 97.0 |
| 3-7 | 8 | 25 | 9.88 | 93.5 |
| 3-8 | 16 | 25 | 9.20 | 87.1 |
| 3-9 | 1 | 26 | 9.67 | 91.7 |
| 3-10 | 4 | 26 | 9.00 | 85.2 |
| 3-11 | 8 | 26 | 9.68 | 91.5 |
| 3-12 | 16 | 26 | 8.70 | 82.3 |
| 3-13 | 1 | 88 | 8.25 | 78.1 |
| 3-14 | 4 | 88 | 6.75 | 63.9 |
| 3-15 | 8 | 88 | 5.55 | 52.7 |
| 3-16 | 16 | 88 | 4.3 | 40.8 |
| 3-17 | 1 | 89 | 7.85 | 74.3 |
| 3-18 | 4 | 89 | 6.25 | 59.2 |
| 3-19 | 8 | 89 | 4.93 | 46.6 |
| 3-20 | 16 | 89 | 3.68 | 34.8 |
| 3-21 | 1 | 90 | 8.43 | 79.6 |
| 3-22 | 4 | 90 | 6.53 | 61.8 |
| 3-23 | 8 | 90 | 5.00 | 47.3 |
| 3-24 | 16 | 90 | 3.68 | 34.8 |
| 3-25 | 1 | 91 | 7.85 | 74.3 |
| 3-26 | 4 | 91 | 6.60 | 62.4 |
| 3-27 | 8 | 91 | 5.15 | 48.7 |
| 3-28 | 16 | 91 | 3.40 | 32.2 |
| 3-29 | 0 | Control (Caldwell 96(B-H52)) | 10.58 | 100.0 |

Example 10

Following the general procedure of Example 1, matrix particle suspensions having the following compositions were produced.

| Ingredients | Weight % of Ingredients Formulation | |
|---|---|---|
| | 27 | 28 |
| Cyproconazole* | 3.00 | 3.00 |
| CHRONOPOL ™ 95 (poly(lactic acid) formulation | 10.92 | 6.12 |
| Polystyrene | 1.20 | 6.00 |
| METHOCEL ® A15LV (methylcellulose formulation) | 1.56 | 1.61 |
| Water | 83.32 | 83.27 |
| Total | 100.00 | 100.00 |

*100% a.i. basis. Compensate for purity with polymer.

Figure 4:
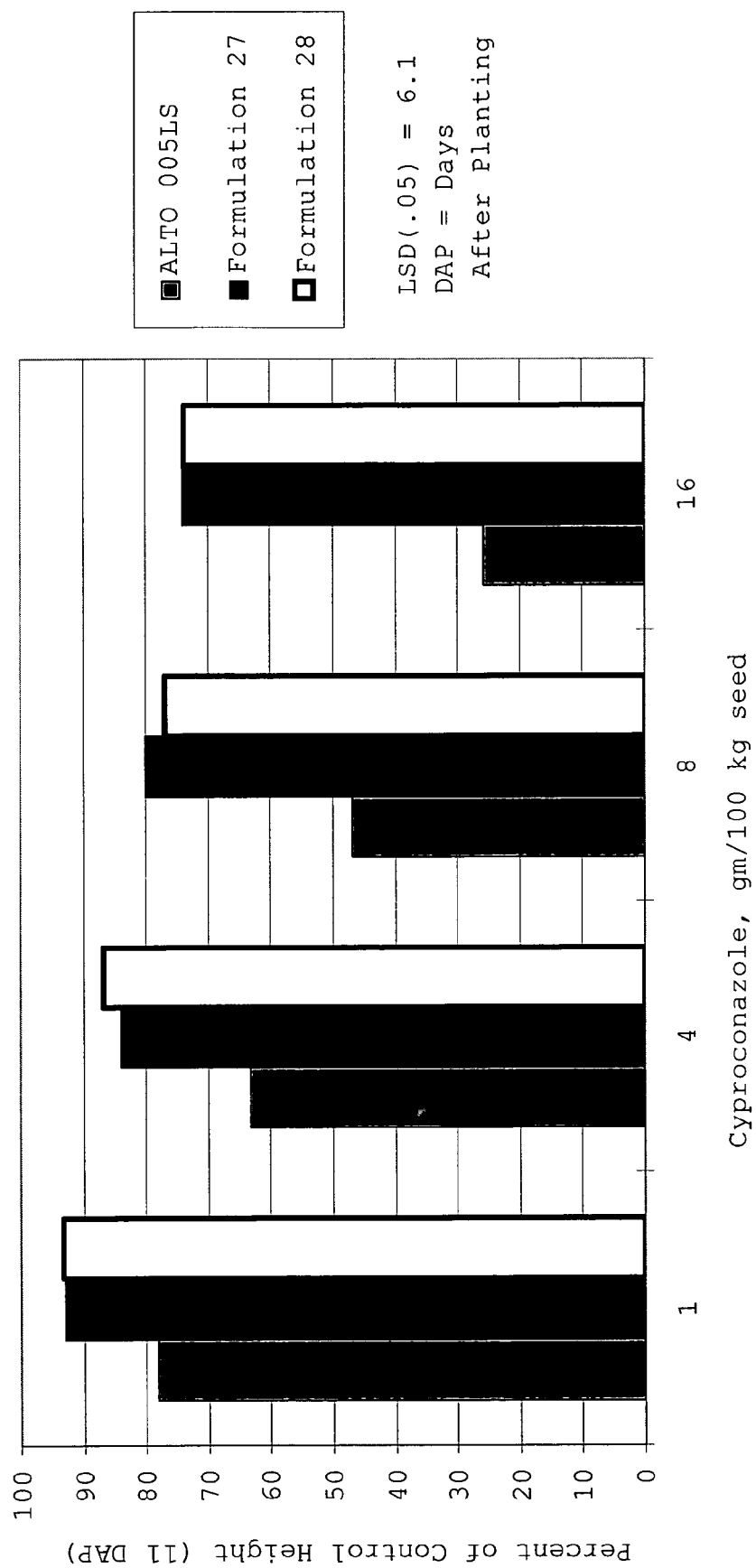
FIG. 4 shows the effect of matrix particle formulations of Example 10 and ALTO® 005LS (cyproconazole formulation) when used as seed treatments on wheat at various rates (g cyproconazole per 100 kg seed), expressed as the height of germinating wheat at 11 DAP as a percent of the height of untreated controls.

The suspensions produced in this Example were applied to wheat using the procedure set forth in Example 7. The table below shows and FIG. 4 illustrates the safety of these treatments at 11 days after planting as compared to ALTO® 005LS (cyproconazole formulation).

| Rep. No. | Rate (g a.i./100 kg seed) | Formulation | Height of Treated Plant in cm (11 DAP) | Percent of Control Height (11 DAP) |
|---|---|---|---|---|
| 4-1 | 1 | 51 | 8.4 | 72.6 |
| 4-2 | 4 | 51 | 7.0 | 60.6 |
| 4-3 | 8 | 51 | 6.7 | 57.4 |
| 4-4 | 16 | 51 | 4.8 | 41.6 |
| 4-5 | 1 | 47 | 9.5 | 82.1 |
| 4-6 | 4 | 47 | 7.7 | 66.4 |
| 4-7 | 8 | 47 | 6.1 | 52.2 |
| 4-8 | 16 | 47 | 3.8 | 32.8 |
| 4-9 | 1 | 48 | 9.7 | 83.2 |
| 4-10 | 4 | 48 | 8.5 | 73.1 |
| 4-11 | 8 | 48 | 6.8 | 58.9 |
| 4-12 | 16 | 48 | 5.5 | 47.4 |
| 4-13 | 1 | ALTO ® 005LS (cyproconazole formulation) | 9.1 | 78.2 |
| 4-14 | 4 | ALTO ® 005LS (cyproconazole formulation) | 7.3 | 63.1 |
| 4-15 | 8 | ALTO ® 005LS (cyproconazole formulation) | 5.5 | 47.0 |
| 4-16 | 16 | ALTO ® 005LS (cyproconazole formulation) | 3.0 | 25.9 |

-continued

| Rep. No. | Rate (g a.i./100 kg seed) | Formulation | Height of Treated Plant in cm (11 DAP) | Percent of Control Height (11 DAP) |
|---|---|---|---|---|
| 4-17 | 1 | 5932801A2 | 10.8 | 92.9 |
| 4-18 | 4 | 5932801A2 | 9.7 | 83.9 |
| 4-19 | 8 | 5932801A2 | 9.3 | 80.0 |
| 4-20 | 16 | 5932801A2 | 8.6 | 74.1 |
| 4-21 | 1 | 5932801B2 | 10.8 | 93.1 |
| 4-22 | 4 | 5932801B2 | 10.1 | 86.9 |
| 4-23 | 8 | 5932801B2 | 8.9 | 77.0 |
| 4-24 | 16 | 5932801B2 | 8.6 | 73.9 |
| 4-25 | 0 | Control (96 Caldwell (B-H52)) | 11.6 | 100.0 |

Example 11

Following the general procedure of Example 1, matrix particle suspensions having the following compositions were produced.

| | Weight % of Ingredients Formulation | | |
|---|---|---|---|
| Ingredients | 29 | 30 | 93 |
| Cyproconazole* | 20.1 | 3.04 | 3.71 |
| CHRONOPOL ™ 95 (poly(lactic acid) formulation) | 79.9 | 10.41 | 8.67 |
| MEHTOCEL ® A15LV (methylcellulose formulation) | — | 1.27 | 1.09 |
| Water | — | 85.28 | 86.53 |
| Total | 100.0 | 100.0 | 100.0 |

*100% a.i. basis. Compensate for purity with polymer.

The following procedure was used to prepare a matrix particle suspension having the composition in the table below. A 38.5% by weight a.i. suspension of cyproconazole was prepared using a laboratory mill. The particles were milled to an average size of less than 10 microns in diameter. Separately, a solution was prepared containing 3.82% by weight of alginic acid and 0.15% by weight of calcium acetate in water. The cyproconazole solution was warmed to 50 C with stirring. The alginic acid/calcium acetate was warmed to 60 C with stirring. The cyproconazole suspension was poured rapidly into the stirring alginic acid solution. The resultant mixture was stirred until it equilibrated to room temperature (about 2 hours). The mixture was poured through a #50 mesh sieve and bottled.

| | Weight % of Ingredients Formulation |
|---|---|
| Ingredients | 82 |
| Cyproconazole* | 14.05 |
| MORWET ® D-425 (naphthalene sulfonate condensate) | 1.83 |
| Calcium Acetate | 0.10 |
| Alginic Acid | 2.42 |
| Water | 81.60 |
| Total | 100.0 |

*100% a.i. basis. Compensate for purity with polymer.

The suspensions produced in this Example were applied to wheat using the procedure set forth in Example 7. The table below shows and FIG. 5 illustrates the safety of Formulation 29 at 10 days after planting (DAP) as compared to ALTO® 005LS (cyproconazole formulation).

Figure 5:
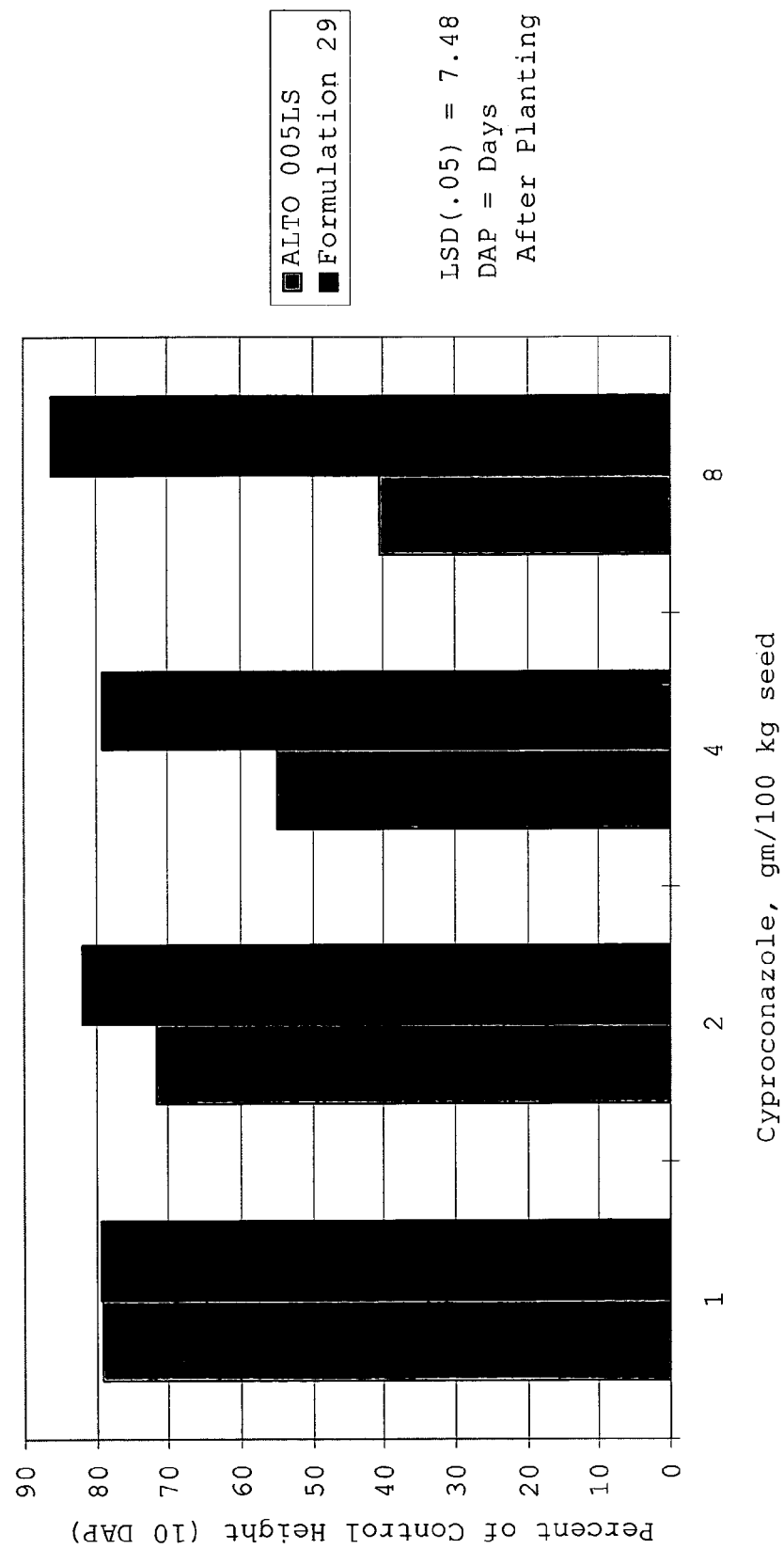
FIGS. 5 and 6 show the effect of a matrix particle formulation of Example 11, Formulation 29, and ALTO® 005LS (cyproconazole formulation) when used as a seed treatment on wheat at various rates (g cyproconazole per 100 kg seed), expressed as the height of germinating wheat at 10 DAP (FIG. 5) or 9 DAP (FIG. 6) as a percent of the height of untreated controls.

| | Data Corresponding to FIG. 5 | | | |
|---|---|---|---|---|
| Rep. No. | Formulation | Rate (g a.i./100 kg seed) | Height of Treated Plant in cm (10 DAP) | Percent of Control Height (10 DAP) |
| 5-1 | ALTO® 005LS (cyproconazole formulation) | 1 | 8.08 | 79.1 |
| 5-2 | ALTO ® 005LS (cyproconazole formulation) | 2 | 7.33 | 71.6 |
| 5-3 | ALTO ® 005LS (cyproconazole formulation) | 4 | 5.63 | 55.0 |
| 5-4 | ALTO ® 005LS (cyproconazole formulation) | 8 | 4.15 | 40.5 |
| 5-5 | 29 | 1 | 8.13 | 79.5 |
| 5-6 | 29 | 2 | 8.38 | 81.9 |
| 5-7 | 29 | 4 | 8.10 | 79.3 |
| 5-8 | 29 | 8 | 8.80 | 86.1 |
| 5-9 | 35 | 1 | 10.50 | 102.7 |
| 5-10 | 35 | 2 | 9.43 | 92.2 |
| 5-11 | 35 | 4 | 8.95 | 87.6 |
| 5-12 | 35 | 8 | 8.08 | 79.0 |
| 5-13 | Untreated Check | 0 | 10.23 | 100.0 |

Figure 6:
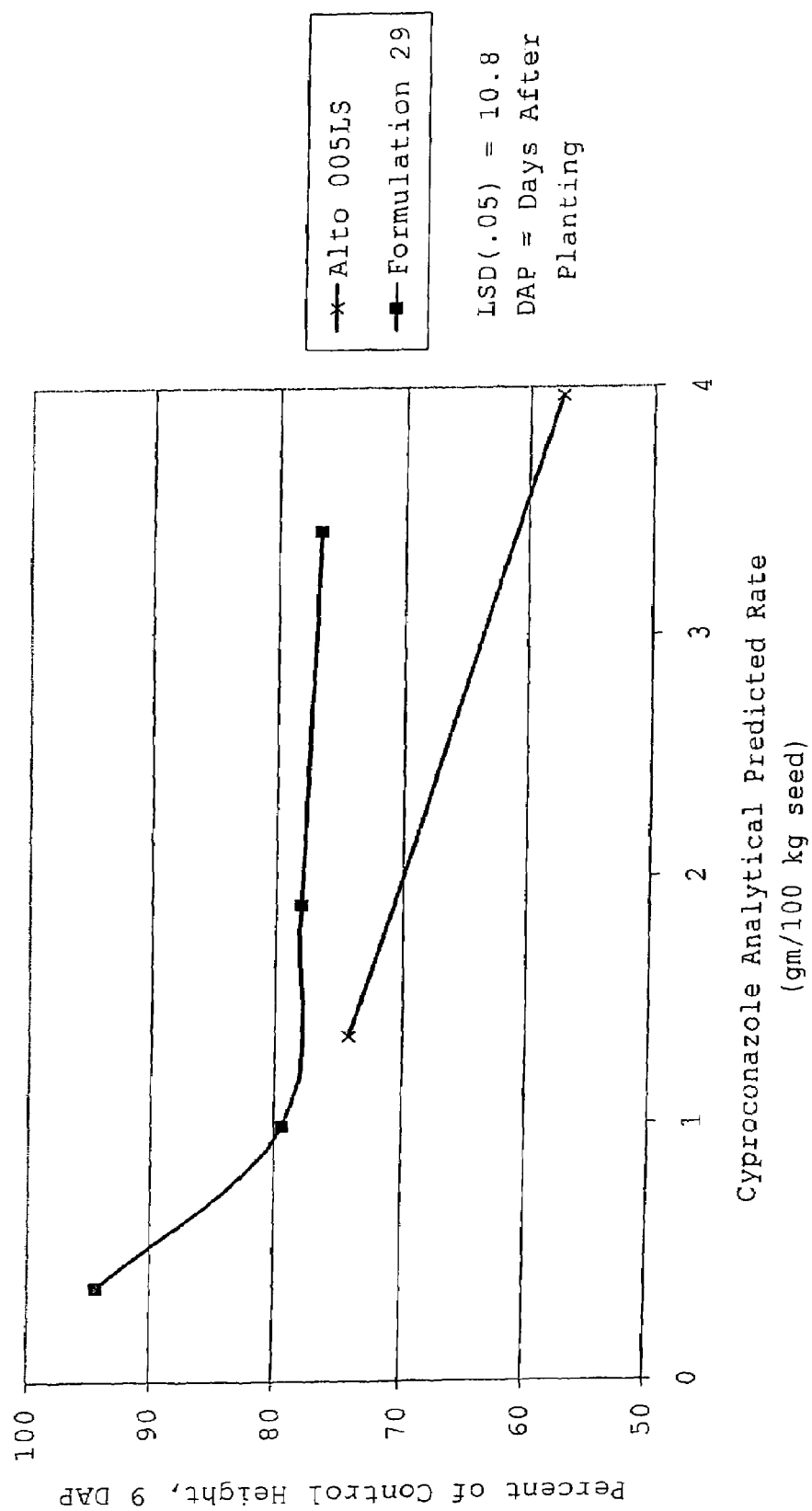
Figure 7:
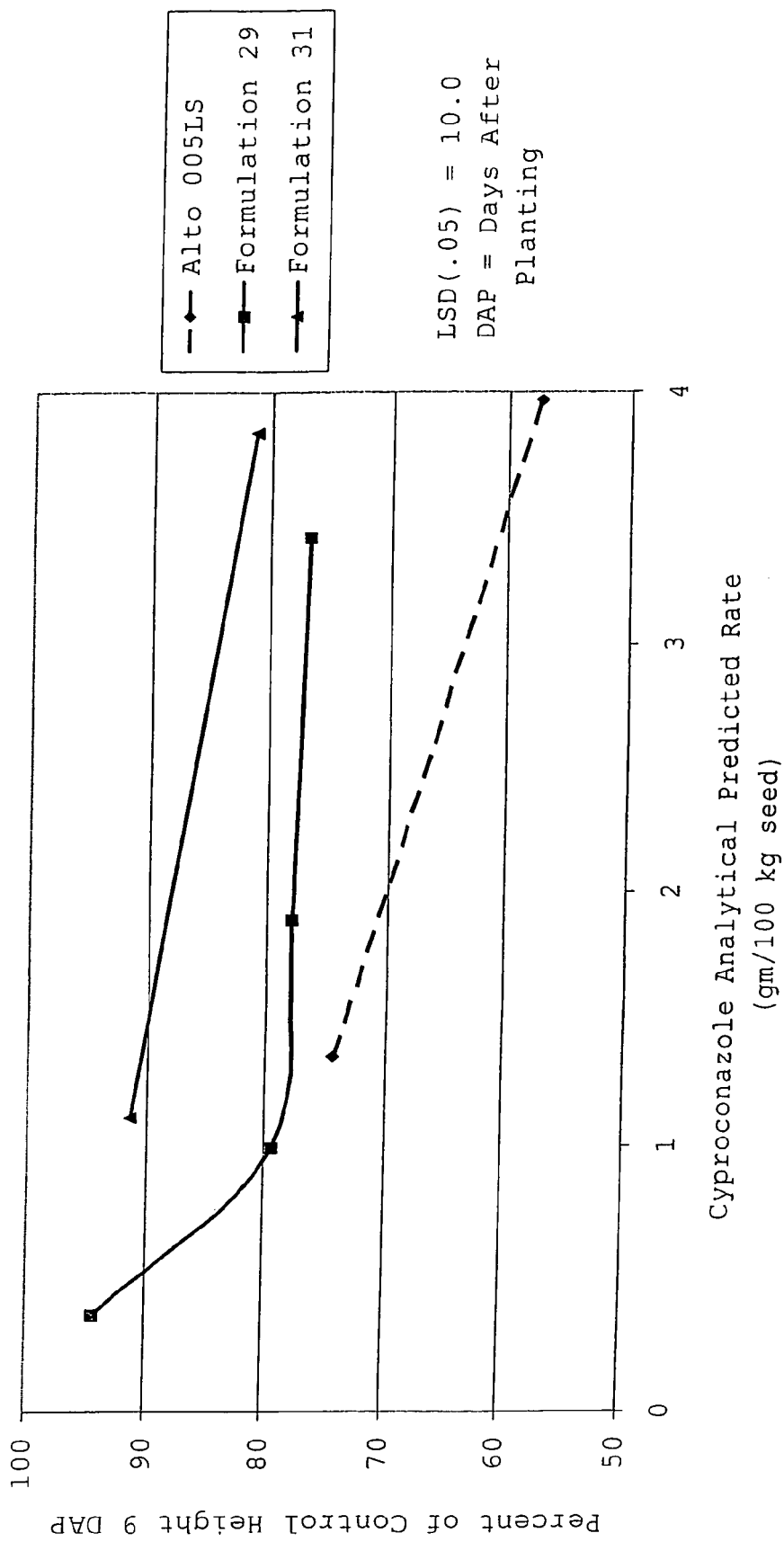
FIG. 7 shows the effect of matrix particle formulations of Example 12, Formulation 29, Formulation 31, and ALTO® 005LS (cyproconazole formulation), when used as seed treatments on wheat at various rates (g cyproconazole per 100 kg seed), expressed as the height of germinating wheat as a percent of the height of untreated controls at 9 DAP.

The table below shows and FIG. 6 illustrates the safety of Formulation 30 at 10 days after planting (DAP) as compared to ALTO® 005LS (cyproconazole formulation).

| | | Data Corresponding to FIG. 6 | | | |
|---|---|---|---|---|---|
| Rep. No. | Formulation | Intended Application Rate (g a.i./100 kg seed) | Analytical Percent Recovery of Applied | Predicted Rate (g a.i./100 kg seed) | Height of Treated Plant in cm (10 DAP) | Percent of Control Height (10 DAP) |
| 6-1 | 97 | 1.1 | 69 | 0.76 | 8.63 | 79.63 |
| 6-2 | 97 | 4.4 | 81.4 | 3.58 | 7.05 | 65.02 |
| 6-3 | 97 | 8.8 | 83 | 7.30 | 5.68 | 52.33 |

-continued

| Data Corresponding to FIG. 6 | | | | | | |
|---|---|---|---|---|---|---|
| Rep. No. | Formulation | Intended Application Rate (g a.i./ 100 kg seed) | Analytical Percent Recovery of Applied | Predicted Rate (g a.i./100 kg seed) | Height of Treated Plant in cm (10 DAP) | Percent of Control Height (10 DAP) |
| 6-4 | 97 | 17.6 | 79.7 | 14.03 | 3.98 | 36.85 |
| 6-5 | 49 | 1.1 | 19.1 | 0.21 | 10.73 | 98.80 |
| 6-6 | 49 | 4.4 | 13.1 | 0.58 | 10.03 | 92.48 |
| 6-7 | 49 | 8.8 | 11.6 | 1.02 | 9.80 | 90.33 |
| 6-8 | 49 | 17.6 | 19 | 3.34 | 9.08 | 83.70 |
| 6-9 | 30 | 1.1 | 32.7 | 0.36 | 10.25 | 94.40 |
| 6-10 | 30 | 4.4 | 22.6 | 0.99 | 8.60 | 79.40 |
| 6-11 | 30 | 8.8 | 21.5 | 1.89 | 8.45 | 78.03 |
| 6-12 | 30 | 17.6 | 19.5 | 3.43 | 8.33 | 76.70 |
| 6-13 | 31 | 1.1 | 100.9 | 1.11 | 9.93 | 91.35 |
| 6-14 | 31 | 4.4 | 87.3 | 3.84 | 8.80 | 81.30 |
| 6-15 | 31 | 8.8 | 134.9 | 11.87 | 8.53 | 78.63 |
| 6-16 | 31 | 17.6 | 116.9 | 20.57 | 7.23 | 66.53 |
| 6-17 | 93 | 1.1 | 79.1 | 0.87 | 8.55 | 78.65 |
| 6-18 | 93 | 4.4 | 73.2 | 3.22 | 7.25 | 67.18 |
| 6-19 | 93 | 8.8 | 56.9 | 5.01 | 6.40 | 59.08 |
| 6-20 | 93 | 17.6 | 46.6 | 8.20 | 6.60 | 61.03 |
| 6-25 | 1 | 1.1 | 47.3 | 0.52 | 9.80 | 90.40 |
| 6-26 | 1 | 4.4 | 42.5 | 1.87 | 8.70 | 80.23 |
| 6-27 | 1 | 8.8 | 54.4 | 4.79 | 7.95 | 73.38 |
| 6-28 | 1 | 17.6 | 48.8 | 8.59 | 7.38 | 67.70 |
| 6-29 | 82 | 1.1 | 86.4 | 0.95 | 7.90 | 73.05 |
| 6-30 | 82 | 4.4 | 80.7 | 3.55 | 6.95 | 64.18 |
| 6-31 | 82 | 8.8 | 78.4 | 6.90 | 5.15 | 47.08 |
| 6-32 | 82 | 17.6 | 54 | 9.50 | 5.08 | 46.40 |
| 6-33 | ALTO ® 005LS (cyproconazole formulation) | 1.1 | 122.7 | 1.35 | 8.05 | 74.30 |
| 6-34 | ALTO ® 005LS (cyproconazole formulation) | 4.4 | 90.2 | 3.97 | 6.23 | 57.45 |
| 6-35 | ALTO ® 005LS (cyproconazole formulation) | 8.8 | 95.6 | 8.41 | 3.83 | 35.50 |
| 6-36 | ALTO ® 005LS (cyproconazole formulation) | 17.6 | 89.2 | 15.70 | 2.18 | 20.10 |
| 6-37 | Untreated Check | 0 | | 0.00 | 10.88 | 100.00 |

Example 12

Following the general procedure of Example 1, matrix particle suspensions having the following compositions were produced.

| Ingredients | Weight % of Ingredients Formulation 30 | 31 | 32 |
|---|---|---|---|
| Cyproconazole* | 3.04 | 22.3 | 30 |
| CHRONOPOL ™ 95 (poly(lactic acid) formulation) | 10.41 | 77.7 | 70 |
| METHOCEL ®A15LV (methylcellulose formulation) | 1.27 | | |
| Water | 85.28 | | |
| Total | 100 | 100.0 | 100 |

*100% a.i. basis. Compensate for purity with polymer.

The suspensions produced in this Example were applied to wheat using the procedure set forth in Example 7. The data in the table below show and FIG. 7 illustrates the safety of Formulation 30 and Formulation 31 at 10 days after planting as compared to ALTO® 005LS (cyproconazole formulation).

| Rep. No. | Formulation | Intended Application Rate (g a.i./100 kg seed) | Analytical Percent Recovery of Applied | Predicted Rate (g a.i./100 kg seed) | Height of Treated Plant in cm (10 DAP) | Percent of Control Height (10 DAP) |
|---|---|---|---|---|---|---|
| 6-1 | 97 | 1.1 | 69 | 0.76 | 8.63 | 79.63 |
| 6-2 | 97 | 4.4 | 81.4 | 3.58 | 7.05 | 65.02 |
| 6-3 | 97 | 8.8 | 83 | 7.30 | 5.68 | 52.33 |
| 6-4 | 97 | 17.6 | 79.7 | 14.03 | 3.98 | 36.85 |
| 6-5 | 49 | 1.1 | 19.1 | 0.21 | 10.73 | 98.80 |
| 6-6 | 49 | 4.4 | 13.1 | 0.58 | 10.03 | 92.48 |
| 6-7 | 49 | 8.8 | 11.6 | 1.02 | 9.80 | 90.33 |
| 6-8 | 49 | 17.6 | 19 | 3.34 | 9.08 | 83.70 |
| 6-9 | 30 | 1.1 | 32.7 | 0.36 | 10.25 | 94.40 |
| 6-10 | 30 | 4.4 | 22.6 | 0.99 | 8.60 | 79.40 |
| 6-11 | 30 | 8.8 | 21.5 | 1.89 | 8.45 | 78.03 |
| 6-12 | 30 | 17.6 | 19.5 | 3.43 | 8.33 | 76.70 |
| 6-13 | 31 | 1.1 | 100.9 | 1.11 | 9.93 | 91.35 |
| 6-14 | 31 | 4.4 | 87.3 | 3.84 | 8.80 | 81.30 |
| 6-15 | 31 | 8.8 | 134.9 | 11.87 | 8.53 | 78.63 |
| 6-16 | 31 | 17.6 | 116.9 | 20.57 | 7.23 | 66.53 |
| 6-17 | 93 | 1.1 | 79.1 | 0.87 | 8.55 | 78.65 |
| 6-18 | 93 | 4.4 | 73.2 | 3.22 | 7.25 | 67.18 |
| 6-19 | 93 | 8.8 | 56.9 | 5.01 | 6.40 | 59.08 |
| 6-20 | 93 | 17.6 | 46.6 | 8.20 | 6.60 | 61.03 |
| 6-25 | 1 | 1.1 | 47.3 | 0.52 | 9.80 | 90.40 |
| 6-26 | 1 | 4.4 | 42.5 | 1.87 | 8.70 | 80.23 |
| 6-27 | 1 | 8.8 | 54.4 | 4.79 | 7.95 | 73.38 |
| 6-28 | 1 | 17.6 | 48.8 | 8.59 | 7.38 | 67.70 |
| 6-29 | 82 | 1.1 | 86.4 | 0.95 | 7.90 | 73.05 |
| 6-30 | 82 | 4.4 | 80.7 | 3.55 | 6.95 | 64.18 |
| 6-31 | 82 | 8.8 | 78.4 | 6.90 | 5.15 | 47.08 |
| 6-32 | 82 | 17.6 | 54 | 9.50 | 5.08 | 46.40 |
| 6-33 | ALTO ® 005LS (cyproconazole formulation) | 1.1 | 122.7 | 1.35 | 8.05 | 74.30 |
| 6-34 | ALTO ® 005LS (cyproconazole formulation) | 4.4 | 90.2 | 3.97 | 6.23 | 57.45 |
| 6-35 | ALTO ® 005LS (cyproconazole formulation) | 8.8 | 95.6 | 8.41 | 3.83 | 35.50 |
| 6-36 | ALTO ® 005LS (cyproconazole formulation) | 17.6 | 89.2 | 15.70 | 2.18 | 20.10 |
| 6-37 | Untreated Check | 0 | | 0.00 | 10.88 | 100.00 |

Figure 8:
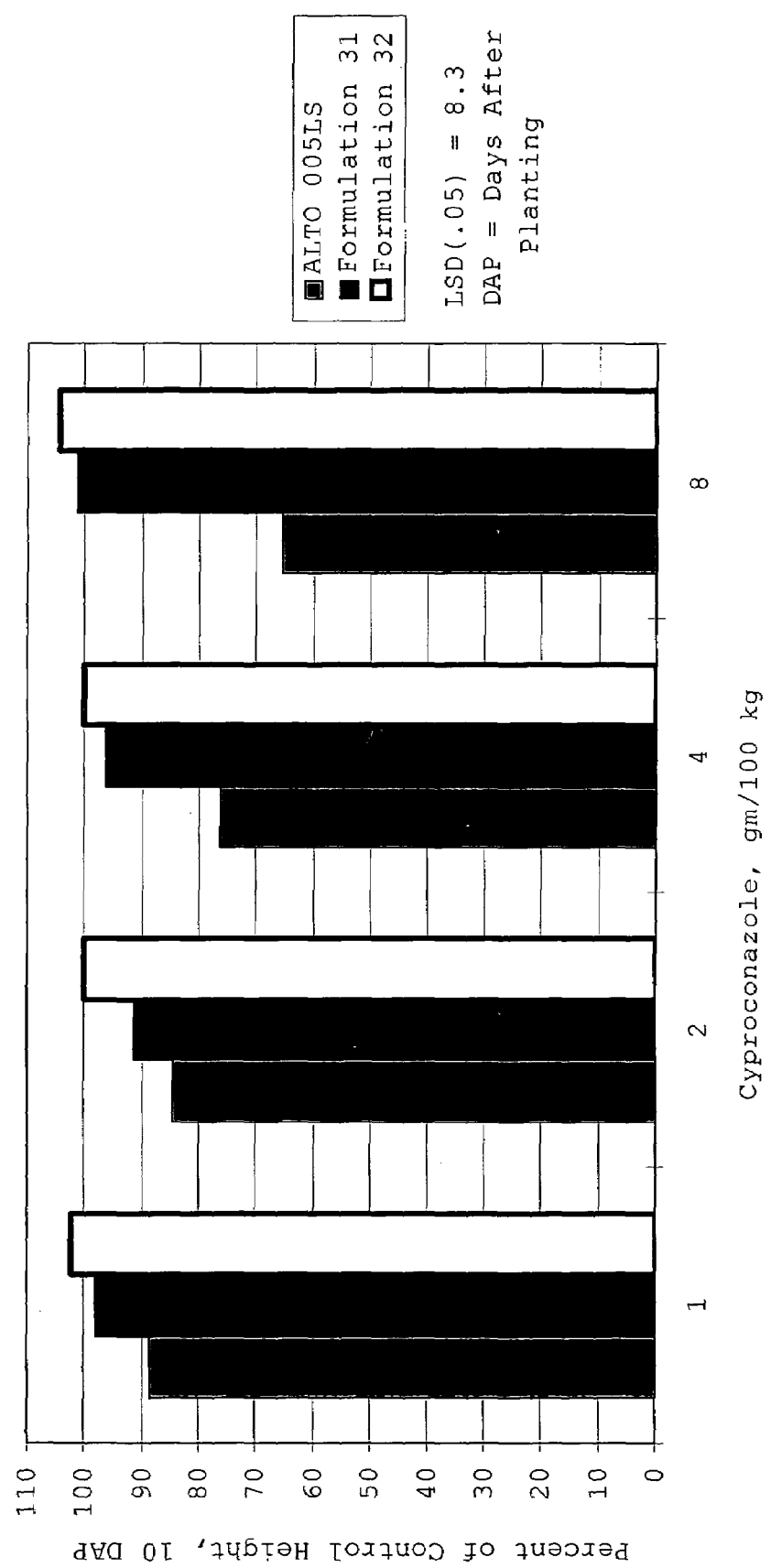
FIG. 8 shows the effect of matrix particle formulations of Example 12, Formulation 31, Formulation 32, and ALTO® 005LS (cyproconazole formulation), when used as seed treatments on wheat at various rates (g cyproconazole per 100 kg seed), expressed as the height of germinating wheat as a percent of the height of untreated controls at 10 DAP.

The table below show and FIG. 8 illustrates the safety of Formulation 31 and Formulation 32 at 10 days after planting as compared to ALTO® 005LS (cyproconazole formulation).

| Rep. No. | Formulation | Rate (g a.i./100 kg seed) | Height of Treated Plant in cm (10 DAP) | Percent of Control Height (10 DAP) |
|---|---|---|---|---|
| 8-1 | ALTO ® 005LS (cyproconazole formulation) | 1 | 8.63 | 88.6 |
| 8-2 | ALTO ® 005LS (cyproconazole formulation) | 2 | 8.25 | 84.7 |
| 8-3 | ALTO ® 005LS (cyproconazole formulation) | 4 | 7.43 | 76.3 |
| 8-4 | ALTO ® 005LS (cyproconazole formulation) | 8 | 6.38 | 65.6 |
| 8-5 | 31 | 1 | 9.50 | 97.8 |
| 8-6 | 31 | 2 | 8.90 | 91.4 |
| 8-7 | 31 | 4 | 9.38 | 96.3 |
| 8-8 | 31 | 8 | 9.88 | 101.4 |
| 8-9 | 32 | 1 | 9.95 | 102.2 |
| 8-10 | 32 | 2 | 9.75 | 100.2 |
| 8-11 | 32 | 4 | 9.75 | 100.2 |
| 8-12 | 32 | 8 | 10.15 | 104.3 |
| 8-13 | Untreated Check | 0 | 9.75 | 100 |

Example 13

Following the general procedure of Example 1 and using the ingredients which are listed below matrix particle suspensions having the following compositions were produced. BIOPOL® D400G (poly(3-hydroxybutyrate-co-hydroxyvalerate) formulation) was obtained from Monsanto Company (St. Louis, Mo.). Polyvinylpyrrolidone/vinyl acetate copolymer (PVP/VA S-630), which was used as a dispersant, was obtained from GAF Chemicals Corp. (Wayne, N.J.).

| Ingredients | Weight % of Ingredients Formulation | | |
|---|---|---|---|
| | 33 | 34 | 35 |
| Cyproconazole* | 10 | 22.3 | 22.3 |
| BIOPOL ® D400G (poly(3-hydroxybutyrate-co-hydroxyvalerate) formulation) | — | 77.7 | — |
| CHRONOPOL ™ 95 (poly(lactic acid) formulation) + inerts | 90 | — | 77.7** |
| Total | 100 | 100.0 | 100.0 |

*100% a.i. basis. Compensate for purity with polymer and inerts.

Figure 9:
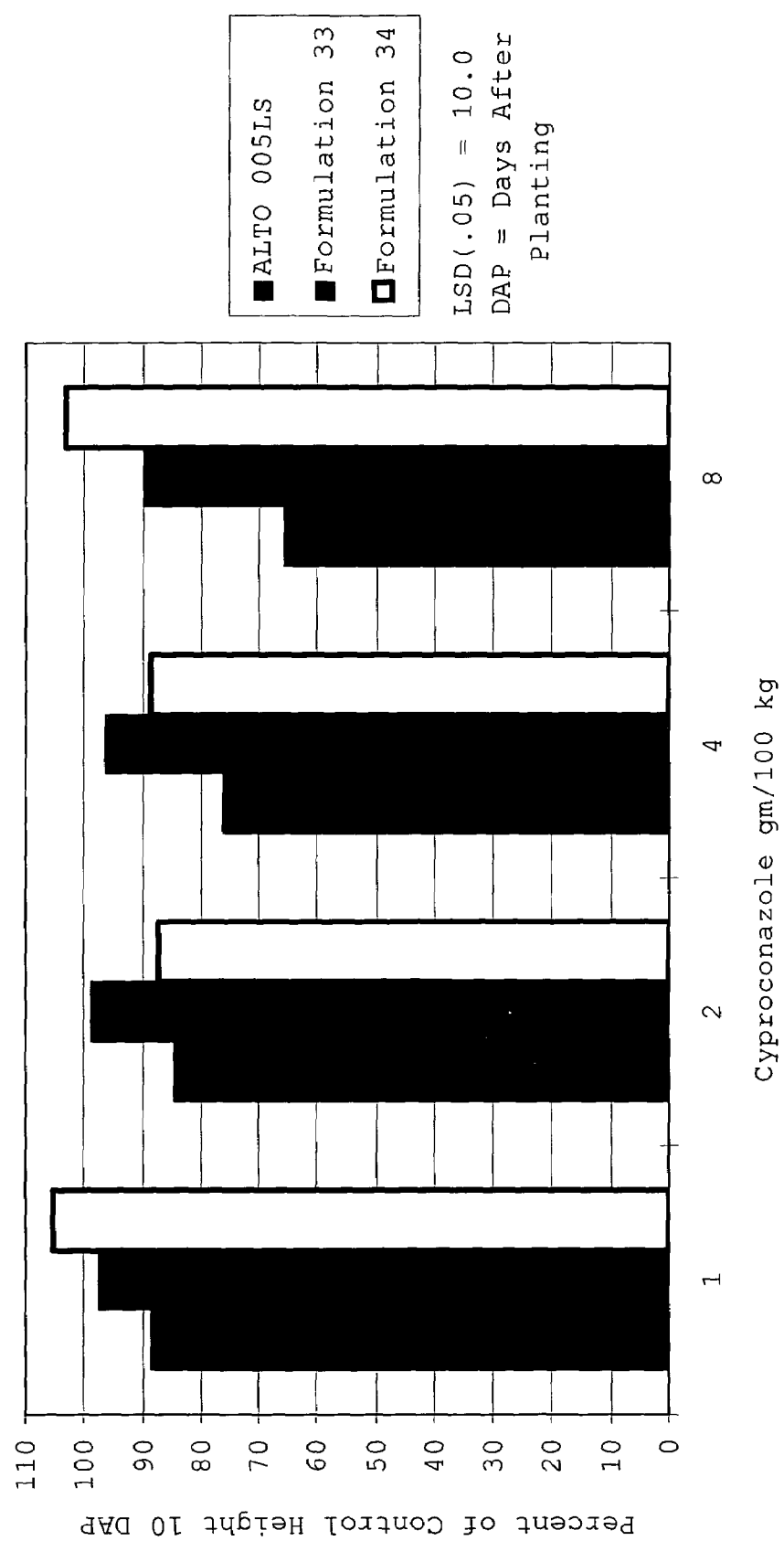
FIG. 9 shows the effect of matrix particle formulations of Example 13, Formulation 33 and Formulation 34, and ALTO® 005LS (cyproconazole formulation), when used as seed treatments on wheat at various rates (g cyproconazole per 100 kg seed), expressed as the height of germinating wheat as a percent of the height of untreated controls at 10 DAP.

The suspensions produced in this Example were applied to wheat using the procedure set forth in Example 7. The data in the table below show and FIG. 9 illustrates the safety of Formulation 33 and Formulation 34 at 10 days after planting as compared to ALTO® 005LS (cyproconazole formulation).

| Rep. No. | Formulation | Rate (g a.i./ 100 kg seed) | Height of Treated Plant in cm (10 DAP) | Percent of Control Height (10 DAP) |
|---|---|---|---|---|
| 9-1 | ALTO ® 005LS (cyporconazole formulation) | 1 | 8.63 | 88.6 |
| 9-2 | ALTO ® 005LS (cyproconazole formulation) | 2 | 8.25 | 84.7 |
| 9-3 | ALTO ® 005LS | 4 | 7.43 | 76.3 |
| 9-4 | ALTO ® 005LS (cyproconazole formulation) | 8 | 6.38 | 65.6 |
| 9-5 | 33 | 1 | 9.50 | 97.5 |
| 9-6 | 33 | 2 | 9.63 | 98.9 |
| 9-7 | 33 | 4 | 9.38 | 96.3 |
| 9-8 | 33 | 8 | 8.75 | 90 |
| 9-9 | 34 | 1 | 10.25 | 105.4 |
| 9-10 | 34 | 2 | 8.50 | 87.3 |
| 9-11 | 34 | 4 | 8.63 | 88.6 |
| 9-12 | 34 | 8 | 10.05 | 103.1 |
| 9-13 | Untreated Check | 0 | 9.75 | 100 |

Figure 10:
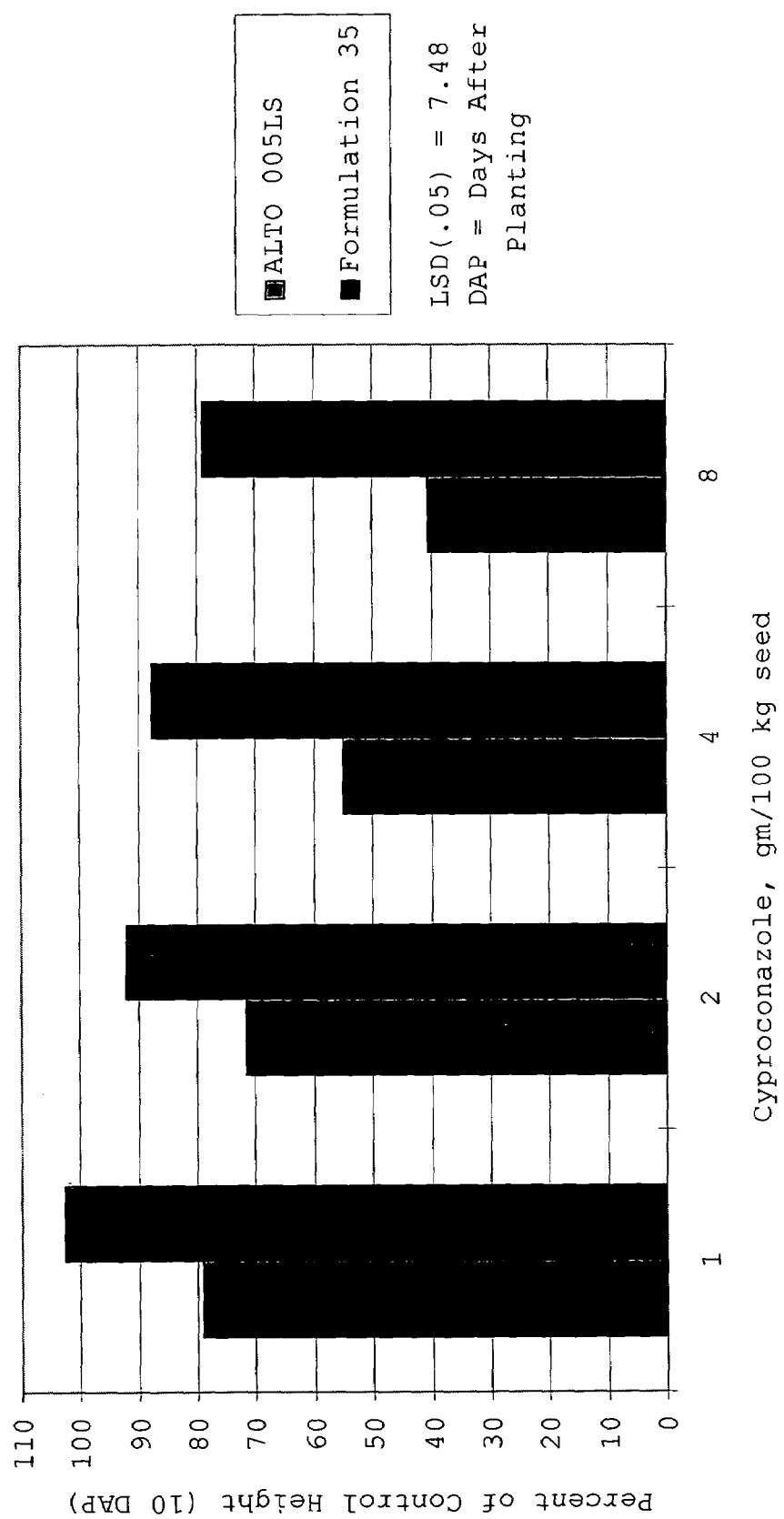
FIG. 10 shows the effect of a matrix particle formulation of Example 13, Formulation 35, and ALTO® 005LS (cyproconazole formulation), when used as seed treatments on wheat at various rates (g cyproconazole per 100 kg seed), expressed as the height of germinating wheat as a percent of the height of untreated controls at 10 DAP.

The data in the table below show and FIG. 10 illustrates the safety of Formulation 35 at 10 days after planting as compared to ALTO® 005LS (cyproconazole formulation).

| Rep. No. | Formulation | Rate (g a.i./ 100 kg seed) | Height of Treated Plant in cm (10 DAP) | Percent of Control Height (10 DAP) |
|---|---|---|---|---|
| 5-1 | ALTO ® 005LS (cyproconazole formulation) | 1 | 8.08 | 79.1 |
| 5-2 | ALTO ® (cyproconazole formulation) | 2 | 7.33 | 71.6 |
| 5-3 | ALTO ® 005LS (cyproconazole formulation) | 4 | 5.63 | 55.0 |
| 5-4 | ALTO ® 005LS (cyproconazole formulation) | 8 | 4.15 | 40.5 |
| 5-5 | 29 | 1 | 8.13 | 79.5 |
| 5-6 | 29 | 2 | 8.38 | 81.9 |
| 5-7 | 29 | 4 | 8.10 | 79.3 |
| 5-8 | 29 | 8 | 8.80 | 86.1 |
| 5-9 | 35 | 1 | 10.50 | 102.7 |
| 5-10 | 35 | 2 | 9.43 | 92.2 |
| 5-11 | 35 | 4 | 8.95 | 87.6 |
| 5-12 | 35 | 8 | 8.08 | 79.0 |
| 5-13 | Untreated Check | 0 | 10.23 | 100.0 |

Example 14

Following the general procedure of Example 1 matrix particle suspensions having the following compositions were produced.

| Ingredients | Weight % of Ingredients Formulation | | |
|---|---|---|---|
| | 36 | 37 | 38 |
| Cyproconazole | *3.17 | *3.01 | *3.01 |
| ELVANOL ® 51-05 (partially hydrolyzed polyvinyl alcohol formulation | 1.64 | 1.26 | 1.26 |
| METHOCEL ® A15LV (methylcellulose formulation | — | — | — |
| CHRONOPOL ™ 50 (poly(lactic acid) formulation) | 11.06 | — | — |
| CHRONOPOL ™ 95 (poly(lactic acid) formulation) | — | 10.43 | — |
| CHORNOPOL ™ 100 (poly(lactic acid) formulation) | — | — | 10.43 |
| Water | 84.13 | 85.30 | 85.30 |
| Total | 100.00 | 100.00 | 100.00 |

Figure 11:
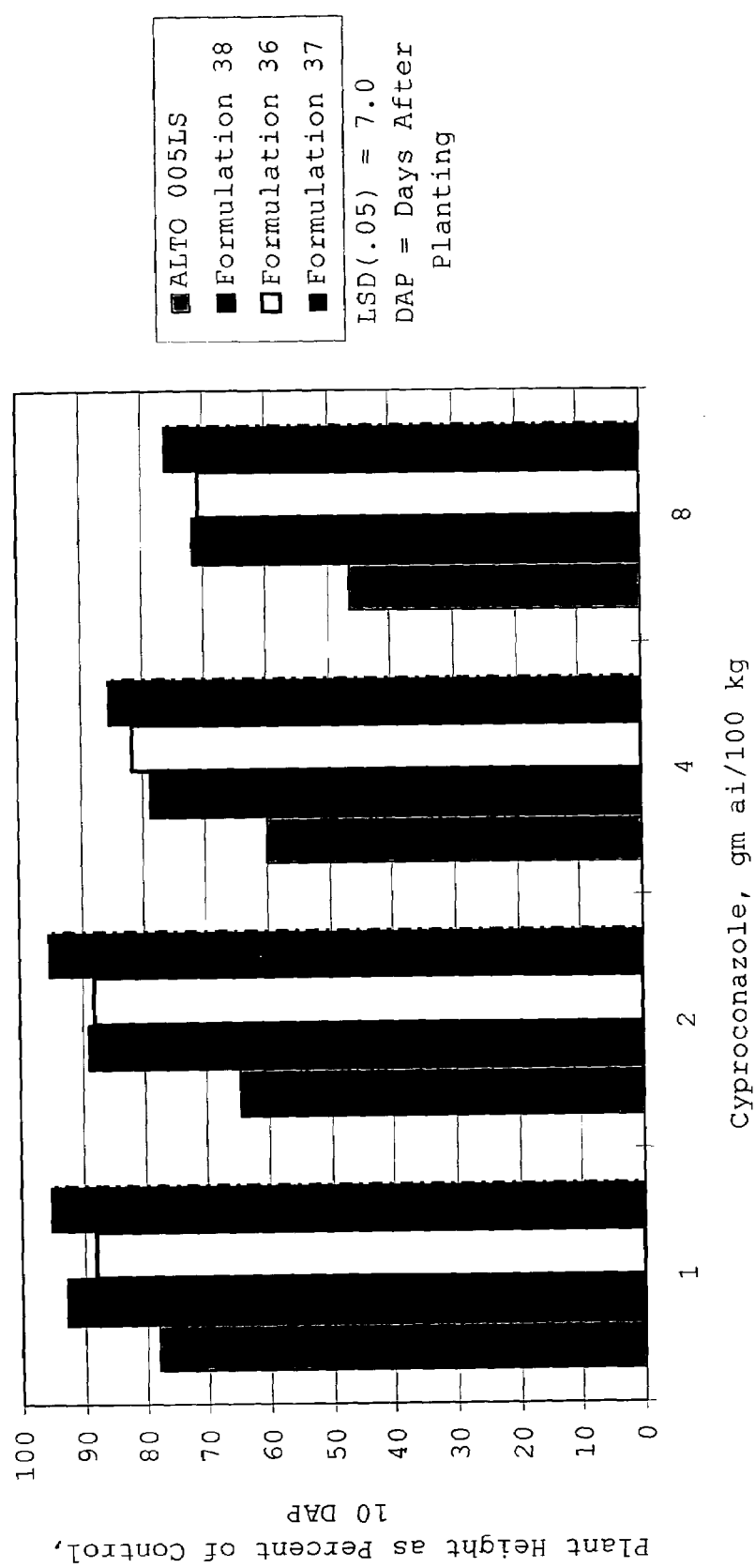
FIG. 11 shows the effect of matrix particle formulations of Example 14 and ALTO® 005LS (cyproconazole formulation) when used as seed treatments on wheat at various rates (g cyproconazole per 100 kg seed), expressed as the height of germinating wheat as a percent of the height of untreated controls at 10 DAP.

The suspensions produced in this Example were applied to wheat using the procedure set forth in Example 7. The data in the table below show and FIG. 11 illustrates the safety of these suspensions at 10 days after planting as compared to ALTO® 005LS (cyproconazole formulation).

| Rep. No. | Formulation | Rate (g a.i./100 kg seed) | Height of Treated Plant in cm (10 DAP) | Percent of Control Height (10 DAP) |
|---|---|---|---|---|
| 11-1 | ALTO ® 005LS (cyproconazole formulation) | 1 | 10.75 | 78.2 |
| 11-2 | ALTO ® 005LS (cyproconazole formulation) | 2 | 8.88 | 64.5 |
| 11-3 | ALTO® 005LS (cyproconazole formulation) | 4 | 8.25 | 60.0 |
| 11-4 | ALTO ® 005LS (cyproconazole formulation) | 8 | 6.38 | 46.4 |
| 11-5 | 38 | 1 | 12.75 | 92.7 |
| 11-6 | 38 | 2 | 12.25 | 89.1 |
| 11-7 | 38 | 4 | 10.88 | 79.1 |
| 11-8 | 38 | 8 | 9.88 | 71.8 |
| 11-9 | 36 | 1 | 12.13 | 88.2 |
| 11-10 | 36 | 2 | 12.13 | 88.2 |
| 11-11 | 36 | 4 | 11.25 | 81.8 |
| 11-12 | 36 | 8 | 9.75 | 70.9 |
| 11-13 | 40 | 1 | 12.25 | 89.1 |
| 11-14 | 40 | 2 | 11.00 | 80.0 |
| 11-15 | 40 | 4 | 9.88 | 71.8 |
| 11-16 | 40 | 8 | 9.00 | 65.5 |
| 11-17 | 39 | 1 | 11.63 | 84.5 |
| 11-18 | 39 | 2 | 11.88 | 86.4 |
| 11-19 | 39 | 4 | 11.00 | 80.0 |
| 11-20 | 39 | 8 | 10.00 | 72.7 |
| 11-21 | 30 | 1 | 13.50 | 98.2 |
| 11-22 | 30 | 2 | 12.88 | 93.6 |
| 11-23 | 30 | 4 | 12.38 | 90.0 |
| 11-24 | 30 | 8 | 10.50 | 76.4 |
| 11-25 | 37 | 1 | 13.13 | 95.5 |
| 11-26 | 37 | 2 | 13.13 | 95.5 |
| 11-27 | 37 | 4 | 11.75 | 85.5 |
| 11-28 | 37 | 8 | 10.50 | 76.4 |
| 11-29 | Untreated Check | 0 | 13.75 | 100.0 |

Example 15

Following the general procedure of Example 1 and using the ingredients which are listed below matrix particle suspensions having the following compositions were produced.

| Ingredients | Weight % of Ingredients Formulation | | |
|---|---|---|---|
| | 39 | 30 | 40 |
| Cyproconazole* | 3.05 | 3.04 | 3.04 |
| ELVANOL ® 51-05 (partially hydrolyzed polyvinyl alcohol formulation) | — | — | — |
| METHOCEL ® AI5LV (methylcellulose formulation) | 1.25 | 1.27 | 1.27 |
| CHRONOPOL ™ 50 (poly(lactic acid) formulation) | 10.40 | — | — |
| CHRONOPOL ™ 95 (poly(lactic acid) formulation) | — | 10.41 | — |
| CHRONOPOL ™ 100 (poly(lactic acid) formulation) | — | — | 10.41 |
| Water | 85.30 | 85.28 | 85.28 |
| Total | 100.00 | 100.00 | 100.00 |

*100% a.i. basis. Compensate for purity with polymer and inerts.

Figure 12:
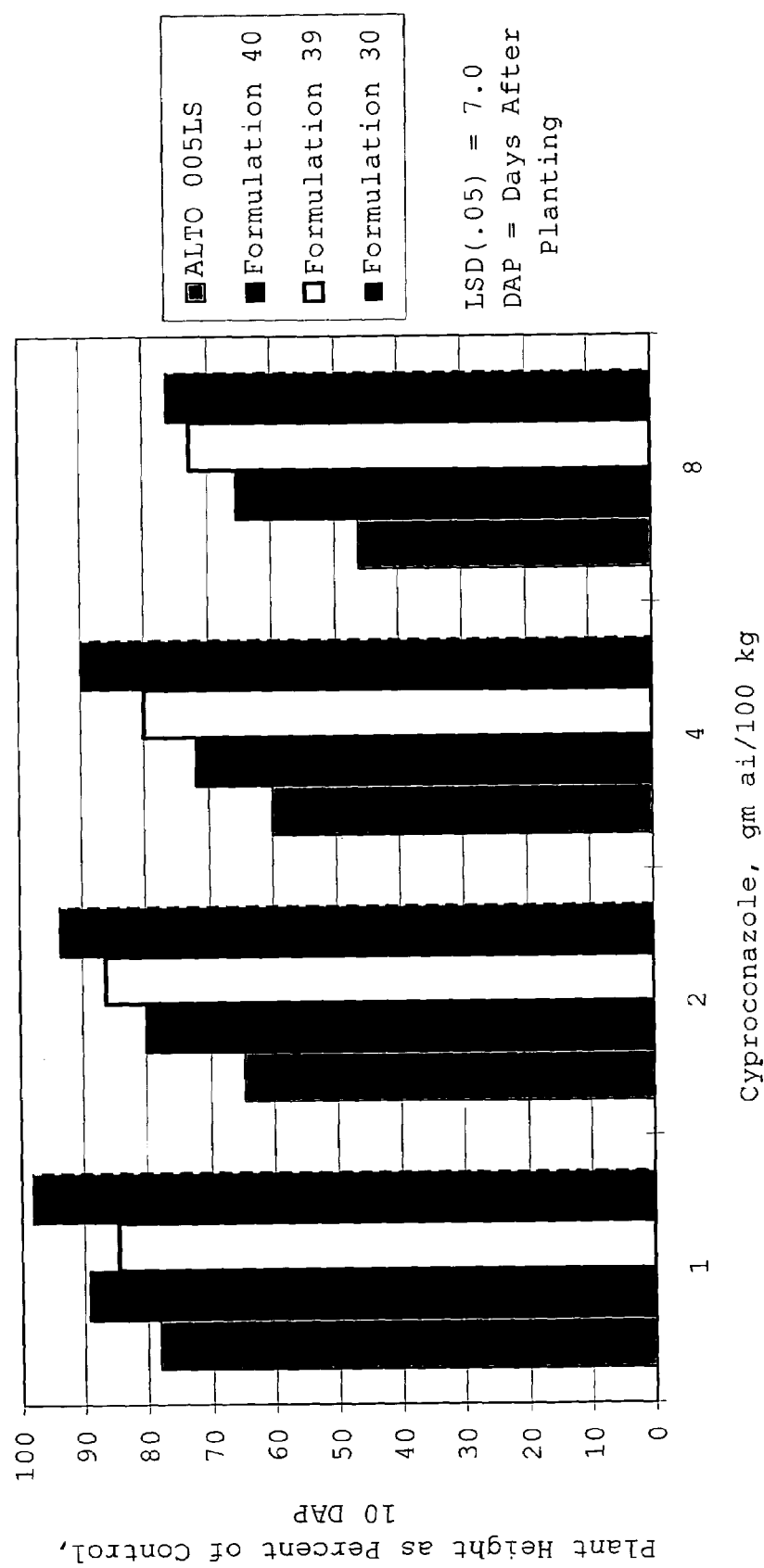
FIG. 12 shows the effect of matrix particle formulations of Example 15 and ALTO® 005LS (cyproconazole formulation) when used as seed treatments on wheat at various rates (g cyproconazole per 100 kg seed), expressed as the height of germinating wheat as a percent of the height of untreated controls at 10 DAP.

The suspensions produced in this Example were applied to wheat using the procedure set forth in Example 7. The data in the table below show and FIG. 12 illustrates the safety of these compounds at 10 days after planting as compared to ALTO® 005LS (cyproconazole formulation).

| Rep. No. | Formulation | Rate (g a.i./100 kg seed) | Height of Treated Plant in cm (10 DAP) | Percent of Control Height (10 DAP) |
|---|---|---|---|---|
| 11-1 | ALTO ® 005LS (cyproconazole formulation) | 1 | 10.75 | 78.2 |
| 11-2 | ALTO ® 005LS (cyproconazole formulation) | 2 | 8.88 | 64.5 |
| 11-3 | ALTO ® 005LS (cyproconazole formulation) | 4 | 8.25 | 60.0 |
| 11-4 | ALTO ® 005LS (cyproconazole formulation) | 8 | 6.38 | 46.4 |
| 11-5 | 38 | 1 | 12.75 | 92.7 |
| 11-6 | 38 | 2 | 12.25 | 89.1 |
| 11-7 | 38 | 4 | 10.88 | 79.1 |
| 11-8 | 38 | 8 | 9.88 | 71.8 |
| 11-9 | 36 | 1 | 12.13 | 88.2 |
| 11-10 | 36 | 2 | 12.13 | 88.2 |
| 11-11 | 36 | 4 | 11.25 | 81.8 |
| 11-12 | 36 | 8 | 9.75 | 70.9 |
| 11-13 | 40 | 1 | 12.25 | 89.1 |
| 11-14 | 40 | 2 | 11.00 | 80.0 |
| 11-15 | 40 | 4 | 9.88 | 71.8 |
| 11-16 | 40 | 8 | 9.00 | 65.5 |
| 11-17 | 39 | 1 | 11.63 | 84.5 |
| 11-18 | 39 | 2 | 11.88 | 86.4 |
| 11-19 | 39 | 4 | 11.00 | 80.0 |
| 11-20 | 39 | 8 | 10.00 | 72.7 |
| 11-21 | 30 | 1 | 13.50 | 98.2 |
| 11-22 | 30 | 2 | 12.88 | 93.6 |
| 11-23 | 30 | 4 | 12.38 | 90.0 |
| 11-24 | 30 | 8 | 10.50 | 76.4 |
| 11-25 | 37 | 1 | 13.13 | 95.5 |
| 11-26 | 37 | 2 | 13.13 | 95.5 |
| 11-27 | 37 | 4 | 11.75 | 85.5 |
| 11-28 | 37 | 8 | 10.50 | 76.4 |
| 11-29 | Untreated Check | 0 | 13.75 | 100.0 |

Example 16

Following the general procedure of Example 2 matrix particle suspensions having the following compositions were produced. LUCITE® #29 (polymethylmethacrylate formulation) was obtained from Polysciences Inc. (Warrington, Pa.).

| Ingredients | Weight % of Ingredients Formulation | |
|---|---|---|
| | 41 | 42 |
| Cyproconazole* | 2.95 | 1.48 |
| LUCITE ® #29 (polymethylmethacrylate formulation) | 11.80 | — |
| Cellulose acetate butyrate | — | 13.27 |
| Methocel ® A15LV (methylcellulose formulation) | 1.00 | 1.00 |
| Water | 84.25 | 84.25 |
| Total | 100.00 | 100.00 |

*100% a.i. basis. Compensate for purity with polymer.

Figure 13:
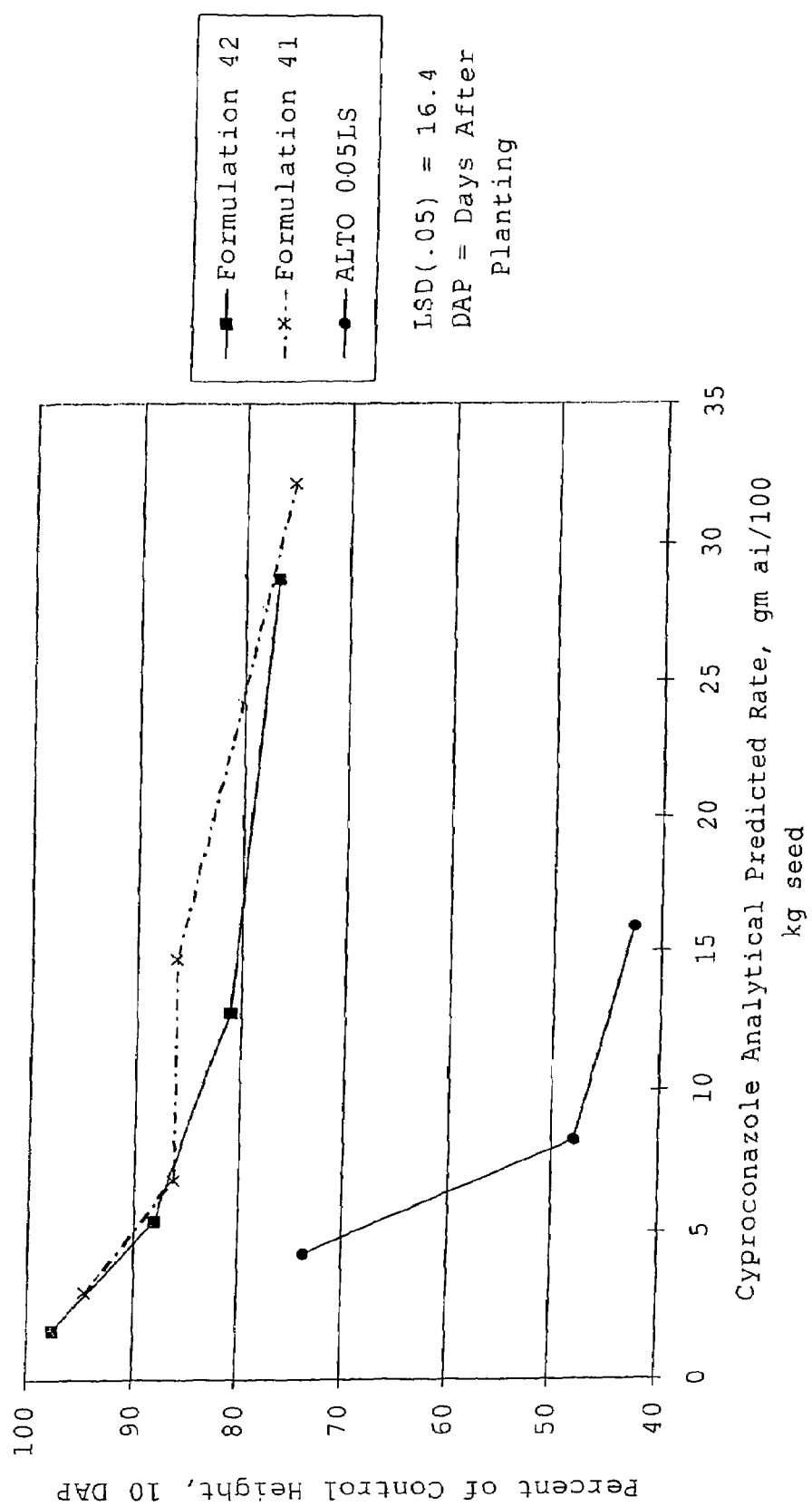
FIG. 13 shows the effect of matrix particle formulations of Example 16 and ALTO® 005LS (cyproconazole formulation) when used as seed treatments on wheat at various rates (g cyproconazole per 100 kg seed), expressed as the height of germinating wheat as a percent of the height of untreated controls at 10 DAP.

The suspensions produced in this Example were applied to wheat using the procedure set forth in Example 7. The data in the table below show and FIG. 13 illustrates the safety of these compounds at 10 days after planting as compared to ALTO® 005LS (cyproconazole formulation).

| Rep. No. | Formulation | Rate (g a.i./100 kg seed) | Analytical Percent Recovery of Applied | Predicted Rate (g a.i./100 kg seed) | Avg. No. of Plants Germinating (out of 12) | Height of Treated Plant in cm (9 DAP) | % of Control Height (9 DAP) |
|---|---|---|---|---|---|---|---|
| 13-1 | ALTO ® 005LS (cyproconazole formulation) | 4.4 | 98.4 | 4.3 | 11.25 | 8.5 | 73.7 |
| 13-2 | ALTO ® 005LS (cyproconazole formulation) | 8.8 | 93.1 | 8.2 | 7.5 | 5.6 | 48 |
| 13-3 | ALTO ® 005LS (cyproconazole formulation) | 17.6 | 90.5 | 15.9 | 3.25 | 5. | 42.6 |
| 13-8 | 42 | 4.4 | 38.2 | 1.85 | 10.25 | 11.3 | 97.6 |
| 13-9 | 42 | 8.8 | 61.9 | 5.99 | 11.25 | 10.2 | 88 |
| 13-10 | 42 | 17.6 | 72.8 | 14.09 | 11.25 | 9.4 | 81.2 |
| 13-11 | 42 | 35.2 | 81.6 | 31.6 | 11.75 | 8.9 | 76.9 |
| 13-16 | 41 | 4.4 | 68.4 | 3.31 | 10.25 | 11. | 94.6 |
| 13-17 | 41 | 8.8 | 77.7 | 7.52 | 11.5 | 10. | 86.2 |
| 13-18 | 41 | 17.6 | 83.9 | 16.24 | 11 | 10. | 86.3 |
| 13-19 | 41 | 35.2 | 91.4 | 35.39 | 11.75 | 8.8 | 75.4 |
| 13-20 | 24 | 4.4 | 123.2 | 5.96 | 11.5 | 10.1 | 86.6 |
| 13-21 | 24 | 8.8 | 120.9 | 11.7 | 8.25 | 8.4 | 72.1 |
| 13-22 | 24 | 17.6 | 111.9 | 21.66 | 9.75 | 9.5 | 82.1 |
| 13-23 | 24 | 35.2 | 138.6 | 53.67 | 11.25 | 8.7 | 74.6 |
| 13-24 | UNTREATED CHECK | 0 | | | 12 | 11.6 | 100 |

Example 17

Following the general procedure of Example 2, a matrix particle suspension having the following composition and properties was produced. Tebuconazole was obtained from Bayer (Leverkusen, Germany).

Formulation 43

| Ingredients | % w/w |
|---|---|
| Tebuconazole* | 3.52 |
| CHRONOPOL ™ 95 (poly(lactic acid) formulation) | 14.35 |
| Urea | 4.49 |
| METHOCEL ® A15LV (methylcellulose formulation) | 0.50 |
| Water | 77.14 |
| Total | 100.0 |
| Property | |
| Tebuconazole* (Wt %) | 3.37 |
| Density, g/mL, 24° C. | 1.05 |
| Mean particle size, μm | 41 |

*100% a.i. basis. Compensate for purity with polymer.

Example 18

Following the general procedure of Example 1 a matrix particle suspension having the following composition and properties was produced.

Formulation 44

| Ingredients | % w/w |
|---|---|
| Tebuconazole* | 2.95 |
| LUCITE ® # 29 (polymethyl-methacrylate formulation) | 11.80 |
| METHOCEL ® A15LV (methylcellulose formulation) | 1.00 |
| Water | 84.25 |
| Total | 100.0 |
| Property | |
| % Tebuconazole | 3.34 |
| Density, g/cc, 24° C. | 1.03 |
| Particle Size, microns, mean | 1.9 |

*100% a.i. basis. Compensate for purity with polymer.

Figure 14:
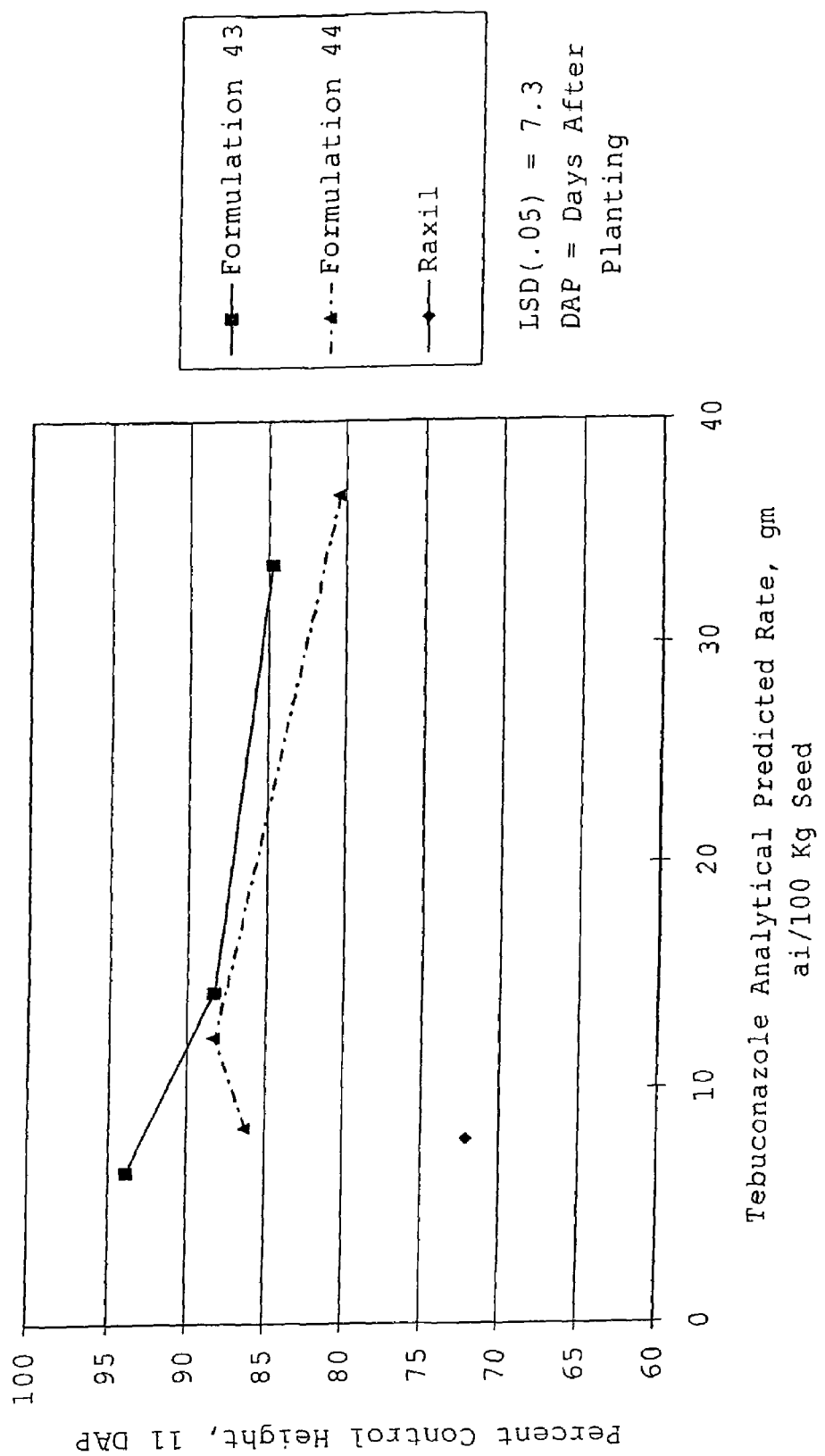
FIG. 14 shows the effect of matrix particle formulations of Examples 17 and 18, Formulation 43 and Formulation 44, respectively, and RAXIL® (thiram formulation) when used as seed treatments on wheat at various rates (g tebuconazole per 100 kg seed), expressed as the height of germinating wheat as a percent of the height of untreated controls at 11 DAP.

Formulation 43 and Formulation 44 were applied to wheat using the procedure set forth in Example 7. The data in the table below show and FIG. 14 illustrates the safety of these compounds at 10 days after planting as compared to RAXIL® (thiram formulation) (Bayer, Leverkusen, Germany), a commercial fast-release formulation of tebuconazole.

| Rep. No. | Formulation | Rate (g a.i./100 kg seed) | Analytical Percent Recovery of Applied | Predicted Rate (g a.i./100 kg seed) | Avg. No. of Plants Germinating (out of 12) | Height of Treated Plant in cm (11 DAP) | % of Control Height (11 DAP) |
|---|---|---|---|---|---|---|---|
| 14-1 | ALTO ® 005LS (cyproconazole formulation) | 8.8 | 85.2 | 7.5 | 11.8 | 6.3 | 56.4 |
| 14-2 | RAXIL ® (thiram formulation) 0.26 FS | 8.8 | 88.3 | 7.8 | 12.0 | 8.1 | 72.1 |
| 14-3 | OPUS ® (expoxiconazole formulation) 125 SC | 8.8 | 62.4 | 5.5 | 12.0 | 2.9 | 25.5 |
| 14-4 | 41 | 8.8 | 66.3 | 5.8 | 12.0 | 10.2 | 91.4 |
| 14-5 | 41 | 17.6 | 86.4 | 15.2 | 12.0 | 9.6 | 85.9 |
| 14-6 | 41 | 35.2 | 96.8 | 34.1 | 12.0 | 8.7 | 77.5 |
| 14-7 | 15 | 8.8 | 75.3 | 6.6 | 11.8 | 9.6 | 86.0 |

-continued

| Rep. No. | Formulation | Rate (g a.i./100 kg seed) | Analytical Percent Recovery of Applied | Predicted Rate (g a.i./100 kg seed) | Avg. No. of Plants Germinating (out of 12) | Height of Treated Plant in cm (11 DAP) | % of Control Height (11 DAP) |
|---|---|---|---|---|---|---|---|
| 14-8 | 15 | 17.6 | 82 | 14.4 | 12.0 | 9.3 | 83.1 |
| 14-9 | 15 | 35.2 | 94.4 | 33.2 | 12.0 | 9.1 | 81.3 |
| 14-10 | 77 | 8.8 | 88.8 | 7.8 | 12.0 | 9.4 | 84.1 |
| 14-11 | 77 | 17.6 | 78.4 | 13.8 | 12.0 | 8.3 | 73.9 |
| 14-12 | 77 | 35.2 | 100.3 | 35.3 | 11.8 | 7.9 | 70.2 |
| 14-13 | 43 | 8.8 | 73.1 | 6.4 | 12.0 | 10.5 | 93.9 |
| 14-14 | 43 | 17.6 | 80.8 | 14.2 | 12.0 | 9.9 | 88.3 |
| 14-15 | 43 | 35.2 | 95.5 | 33.6 | 12.0 | 9.5 | 84.8 |
| 14-16 | 44 | 8.8 | 94.7 | 8.3 | 12.0 | 9.7 | 86.4 |
| 14-17 | 44 | 17.6 | 69.6 | 12.2 | 11.5 | 9.9 | 88.3 |
| 14-18 | 44 | 35.2 | 104.3 | 36.7 | 12.0 | 9.0 | 80.5 |
| 14-19 | 45 | 8.8 | 64 | 5.6 | 12.0 | 6.3 | 56.3 |
| 14-20 | 45 | 17.6 | 63.9 | 11.2 | 12.0 | 4.2 | 37.5 |
| 14-21 | 45 | 35.2 | 84.5 | 29.7 | 12.0 | 2.5 | 21.9 |
| 14-22 | 46 | 8.8 | 78.9 | 6.9 | 11.5 | 7.8 | 69.5 |
| 14-23 | 46 | 17.6 | 77.7 | 13.7 | 12.0 | 6.7 | 59.5 |
| 14-24 | 46 | 35.2 | 93.2 | 32.8 | 12.0 | 3.7 | 33.1 |
| 14-25 | UNTREATED CHECK | 0 | 0 | 0.0 | 12.0 | 11.2 | 100.0 |

Example 19

Following the general procedure of Example 2 a matrix particle suspension having the following composition and properties was produced.

| Formulation 45 | |
|---|---|
| | % w/w |
| Ingredients | |
| Epoxiconazole* | 2.95 |
| CHRONOPOL ® 95 (poly(lactic acid) formulation) | 11.80 |
| METHOCEL ® A15LV (methylcellulose formulation) | 1.00 |
| Water | 84.25 |
| Total | 100.00 |
| Property | |
| Epoxiconazole* (Wt %) | 3.01 |
| Density, g/mL, 24° C. | 1.04 |
| Ave. particle size, μm | 2.80 |

*100% a.i. basis. Compensate for purity with polymer.

Example 20

Following the general procedure of Example 2 a matrix particle suspension having the following composition and properties was produced.

| Formulation 46 | |
|---|---|
| | % w/w |
| Ingredients | |
| Epoxiconazole* | 2.95 |
| LUCITE ® #29 (polymethylmethacrylate formulation) | 11.80 |
| METHOCEL ® Al5LV (methylcellulose formulation) | 1.00 |
| Water | 84.25 |
| Total | 100.00 |
| Property | |
| Epoxiconazole* (Wt %) | 3.18 |
| Density, g/cc, 24° C. | — |
| Particle Size, microns, mean | — |

*100% a.i. basis. Compensate for purity with polymer.

Figure 15:
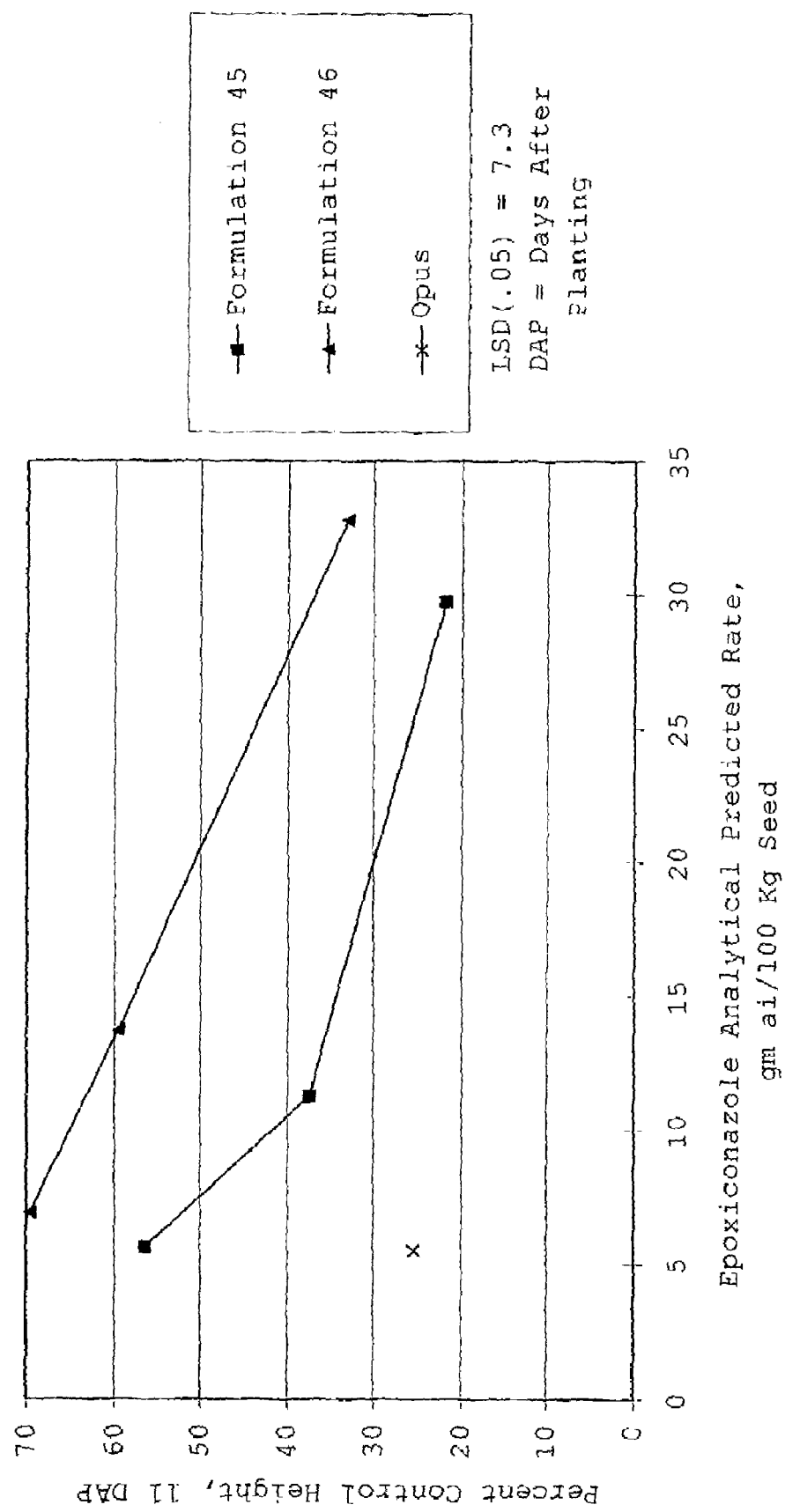
FIG. 15 shows the effect of matrix particle formulations of Examples 19 and 20, Formulation 45 and Formulation 46, respectively, and OPUS® (epoxiconazole formulation) when used as seed treatments on wheat at various rates (g epoxiconazole per 100 kg seed), expressed as the height of germinating wheat as a percent of the height of untreated controls at 11 DAP.

The Formulation 43 and Formulation 44 suspensions were applied to wheat using the procedure set forth in Example 7. The data in the table below show and FIG. 15 illustrates the effects of these suspensions were compared with the effect of OPUS® (epoxiconazole formulation) (BASF AG, Limburgerhof, Germany), a commercial fast-release formulation of epoxiconazole. The maximum safe rate of application of OPUS® (epoxiconazole formulation) as a seed treatment is approximately 1 g/100 kg seed.

| Rep. No. | Formulation | Rate (g a.i./100 kg seed) | Analytical Percent Recovery of Applied | Predicted Rate (g a.i./100 kg seed) | Avg. No. of Plants Germinating (out of 12) | Height of Treated Plant in cm (11 DAP) | % of Control Height (11 DAP) |
|---|---|---|---|---|---|---|---|
| 14-1 | ALTO ® 005LS (cypronoazole formulation) | 8.8 | 85.2 | 7.5 | 11.8 | 6.3 | 56.4 |
| 14-2 | RAXIL ® (thiram formulation) 0.26 FS | 8.8 | 88.3 | 7.8 | 12.0 | 8.1 | 72.1 |
| 14-3 | OPUS ® (epoxiconazole formulation) 125 SC | 8.8 | 62.4 | 5.5 | 12.0 | 2.9 | 25.5 |
| 14-4 | 41 | 8.8 | 66.3 | 5.8 | 12.0 | 10.2 | 91.4 |
| 14-5 | 41 | 17.6 | 86.4 | 15.2 | 12.0 | 9.6 | 85.9 |
| 14-6 | 41 | 35.2 | 96.8 | 34.1 | 12.0 | 8.7 | 77.5 |
| 14-7 | 15 | 8.8 | 75.3 | 6.6 | 11.8 | 9.6 | 86.0 |
| 14-8 | 15 | 17.6 | 82 | 14.4 | 12.0 | 9.3 | 83.1 |
| 14-9 | 15 | 35.2 | 94.4 | 33.2 | 12.0 | 9.1 | 81.3 |
| 14-10 | 77 | 8.8 | 88.8 | 7.8 | 12.0 | 9.4 | 84.1 |
| 14-11 | 77 | 17.6 | 78.4 | 13.8 | 12.0 | 8.3 | 73.9 |
| 14-12 | 77 | 35.2 | 100.3 | 35.3 | 11.8 | 7.9 | 70.2 |
| 14-13 | 43 | 8.8 | 73.1 | 6.4 | 12.0 | 10.5 | 93.9 |
| 14-14 | 43 | 17.6 | 80.8 | 14.2 | 12.0 | 9.9 | 88.3 |
| 14-15 | 43 | 35.2 | 95.5 | 33.6 | 12.0 | 9.5 | 84.8 |
| 14-16 | 44 | 8.8 | 94.7 | 8.3 | 12.0 | 9.7 | 86.4 |
| 14-17 | 44 | 17.6 | 69.6 | 12.2 | 11.5 | 9.9 | 88.3 |
| 14-18 | 44 | 35.2 | 104.3 | 36.7 | 12.0 | 9.0 | 80.5 |
| 14-19 | 45 | 8.8 | 64 | 5.6 | 12.0 | 6.3 | 56.3 |
| 14-20 | 45 | 17.6 | 63.9 | 11.2 | 12.0 | 4.2 | 37.5 |
| 14-21 | 45 | 35.2 | 84.5 | 29.7 | 12.0 | 2.5 | 21.9 |
| 14-22 | 46 | 8.8 | 78.9 | 6.9 | 11.5 | 7.8 | 69.5 |
| 14-23 | 46 | 17.6 | 77.7 | 13.7 | 12.0 | 6.7 | 59.5 |
| 14-24 | 46 | 35.2 | 93.2 | 32.8 | 12.0 | 3.7 | 33.1 |
| 14-25 | UNTREATED CHECK | 0 | 0 | 0.0 | 12.0 | 11.2 | 100.0 |

Example 21

Wheat seeds were coated with an aqueous suspension of the matrix particles of the present invention using the following procedure.

The following water-based film coating concentrates were used for the film coating of seeds: Blue OPACOAT® AG (color coating composition) (Colorcon, West Point, Pa.), SEPIRET® 8127 Rouge (cellulose binder formulation) (Seppic, Paris, France), and SEPIRET® 2020 A Rouge (cellulose binder formulation) (Seppie, Paris, France). SEPIRET® (cellulose binder formulation) and OPACOAT® (color coating composition) formulas are ready-to-use colored film-forming compositions designed for the application of thin films of biodegradable polymers, usually cellulose derivatives of natural origin.

A batch film coating system (Coating Machinery Systems (CMS) PSC-5, Ames, Iowa) was used to apply a precision coating to specific amounts of seed. The water-based film coating concentrates were usually diluted to a 15% w/w solids concentration with water before application. Particle formulations were usually diluted to an active ingredient concentration of 0.12% w/w and coated on seed as a separate coating (using the procedure of Example 7) or in combination with the water-based film coatings. Drying temperatures were usually inlet/outlet at 100° F./90° F. with air flows at 300 cubic feet per minute (CFM). Added coating weights were usually calculated at about 2% w/w, which provides for uniform coverage. After coating, the individual coated batches of seed were analyzed for cyproconazole content ("found a.i.").

| | Formulation: | | | |
|---|---|---|---|---|
| | 47 | 48 | 49 | 50 |
| Treatment: | T1 | T2 | T3 | T4 |
| Wheat seed | Q.S. | Q.S. | Q.S. | Q.S. |
| Cyproconazole @ 100% (ppm) | 176, 88, 44, 11 | 176, 88, 44, 11 | 176, 88, 44, 11 | 176, 88, 44, 11 |
| Found a.i. (ppm) | 139, 63, 29, — | 120, 50, 18, — | | |

| | Formulation: | | |
|---|---|---|---|
| | 51 | ALTO ® 005LS (cyproconazole formulation) | |
| Treatment: | T5 | | |
| Wheat seed | Q.S. | Q.S. | Q.S. |
| Cyproconazole @100% (ppm) | 176, 88, 44, 11 | 176, 88, 44, 22, 11 | 176, 88, 44, 22, 11 |
| Found a.i., ppm (2) | 156, 77, 36, — | 127, 71, 32, 16, 8 | 129, 52, 27, 14, — |

Q.S. = Quantity Sufficient to dilute to the required concentration.

|  | Formulation: | | | |
|---|---|---|---|---|
|  | 29 | 29 | 29 | 61 |
| Treatment: | T6 | T7 | T8 | T9 |
| Wheat seed | Q.S. | Q.S. | Q.S. | Q.S. |
| METHOCEL ® A15LV (methylcellulose formulation) | 110 ppm | — | — | 100 ppm |
| Urea | — | 890 ppm | — | — |
| Ammonium Sulfate | — | — | 890 ppm | — |
| Cyproconazole @100% (ppm) | 88, 44, 22, 11 | 88, 44, 22, 11 | 88, 44, 22, 11 | 88, 44, 22, 11 |
| Found a.i., ppm (1) | 43, 25, 15, — | | | 51, 17, 10, — |

|  | Formulation: 30 |
|---|---|
| Treatment: | T10 |
| Wheat seed | Q.S. |
| METHOCEL ® A15LV (methylcellulose formulation) | — |
| Cyproconazole @100% (ppm) | 88, 44, 22, 11 |
| Found a.i., ppm (1) | 33, 25, 9, — |

Q.S. = Quantity Sufficient to dilute to the required concentration.

Figure 16:
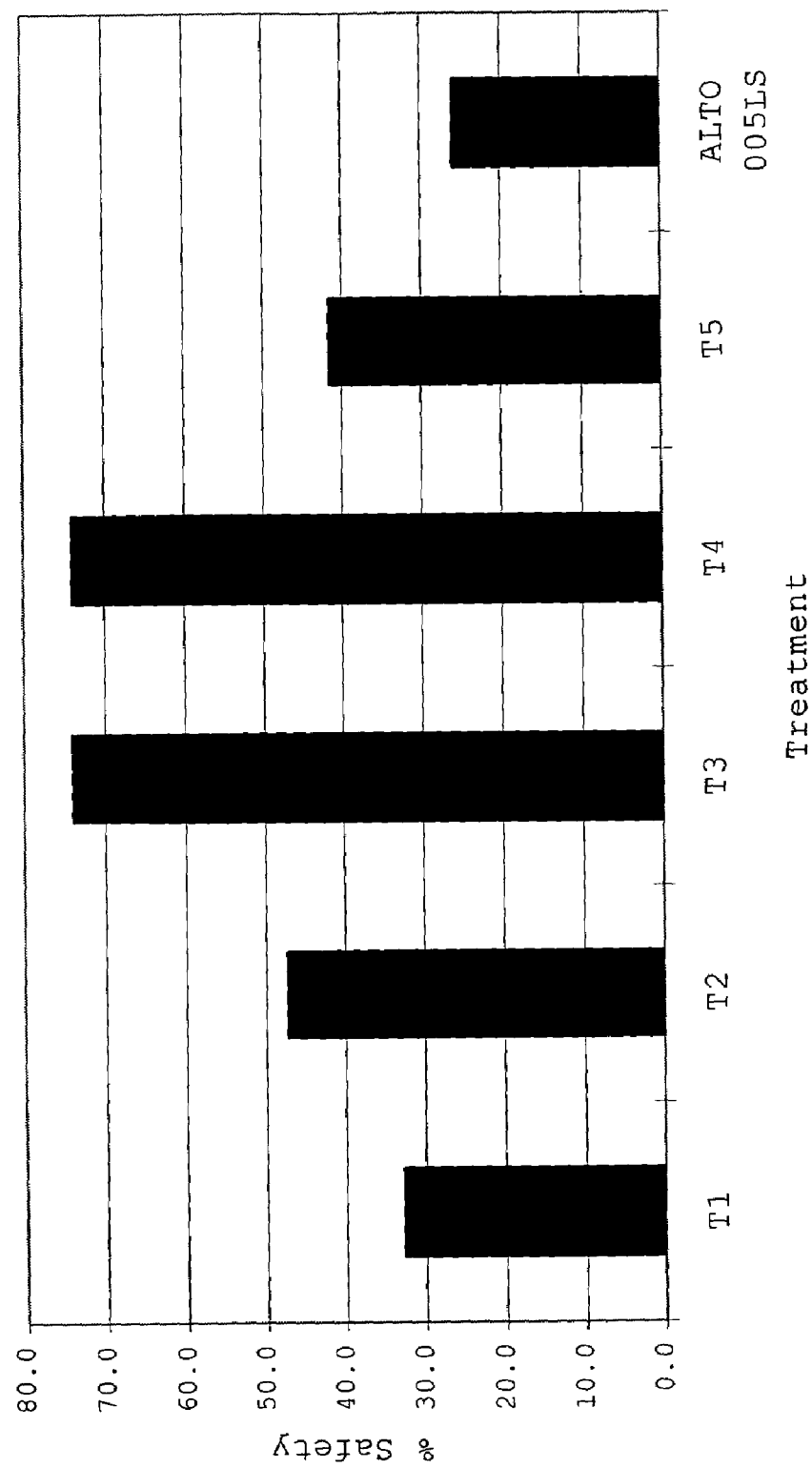
FIG. 16 shows the effect of matrix particle formulations of Example 21 at an application rate of 16 g cyproconazole per 100 kg seed and ALTO® 005LS (cyproconazole formulation) when used as seed treatments on wheat, expressed as the height of germinating wheat as a percent of the height of untreated controls at 8 DAP.

The data in the table below show and FIG. 16 illustrates the safety of the suspensions at an application rate of 16 g active ingredient per 100 kg seed, as compared with ALTO® 005LS (cyproconazole formulation).

| Rep. No. | Treatment | Rate (g a.i./ 100 kg seed) | Avg. No. of Plants Germinating (out of 12) | Height of Treated Plant in cm (8 DAP) | % of Control Height (8 DAP) |
|---|---|---|---|---|---|
| 16-1 | Untreated Check | 0 | 12.0 | 11.6 | 100.0 |
| 16-2 | T1 | 1 | 11.8 | 9.5 | 82.1 |
| 16-3 | T2 | 1 | 12.0 | 9.7 | 83.2 |
| 16-4 | T3 | 1 | 11.5 | 10.8 | 92.9 |
| 16-5 | T4 | 1 | 12.0 | 10.8 | 93.1 |
| 16-6 | T5 | 1 | 12.0 | 8.4 | 72.6 |
| 16-7 | ALTO ® 005LS (cyproconazole formulation) | 1 | 12.0 | 9.1 | 78.2 |
| 16-9 | T1 | 4 | 11.8 | 7.7 | 66.4 |
| 16-10 | T2 | 4 | 11.8 | 8.5 | 73.1 |
| 16-11 | T3 | 4 | 11.5 | 9.7 | 83.9 |
| 16-12 | T4 | 4 | 12.0 | 10.1 | 86.9 |
| 16-13 | T5 | 4 | 12.0 | 7.0 | 60.6 |
| 16-14 | ALTO 005LS (cyproconazole formulation) | 4 | 12.0 | 7.3 | 63.1 |
| 16-16 | T1 | 8 | 11.5 | 6.1 | 52.2 |
| 16-17 | T2 | 8 | 12.0 | 6.8 | 58.9 |
| 16-18 | T3 | 8 | 12.0 | 9.3 | 80.0 |
| 16-19 | T4 | 8 | 12.0 | 8.9 | 77.0 |
| 16-20 | T5 | 8 | 12.0 | 6.7 | 57.4 |
| 16-21 | ALTO ® 005LS (cyproconazole formulation) | 8 | 11.8 | 5.5 | 47.0 |
| 16-23 | T1 | 16 | 12.0 | 3.8 | 32.8 |
| 16-24 | T2 | 16 | 12.0 | 5.5 | 47.4 |
| 16-25 | T3 | 16 | 11.8 | 8.6 | 74.1 |
| 16-26 | T4 | 16 | 12.0 | 8.6 | 73.9 |
| 16-27 | T5 | 16 | 12.0 | 4.8 | 41.6 |
| 16-28 | ALTO ® (cyproconazole formulation) 005LS | 16 | 11.8 | 3.0 | 25.9 |

Example 22

In this example, the polymers used were poly(methyl methacrylate) (350,000 MW, Polysciences, Inc., Warrington, Pa.) or poly(styrene/maleic anhydride) (75% styrene, Sigma Chemical Co., St. Louis, Mo.). The organic solvent was methylene chloride (American Chemical Society analytical reagent grade). Dispersing agents used were METHOCEL® A15LV (methylcellulose formulation) (methyl cellulose Dow Chemical, Midland, Mich.); ELVANOL® 51-05 (partially hydrolyzed polyvinyl alcohol formulation) (polyvinyl alcohol, DuPont, Wilmington, Del.); or YELKINOL™ P (lecithin formulation) (lecithin, Archer Daniels Midland Company, Decatur Ill.). Active ingredients used were epoxiconazole (technical grade @ 96.2%, BASF) or tebuconazole (technical grade @ 98.6%, Bayer).

All formulations were prepared by an oil-in-water (O/W) emulsion/solvent evaporation procedure. Briefly, the polymer and active ingredient were dissolved in methylene chloride at room temperature to form a hydrophobic solution (15% solids). The hydrophobic (oil, O) phase was added to a cooled (<5° C.) 0.5-3.0% aqueous dispersant solution (water, W) and sheared with a Silverson Model L4R homogenizer (large hole screen, 1.5 cm.) for 5 minutes at setting #5 to form an emulsion. The organic solvent was then evaporated with stirring at ambient temperatures in a fume hood. The resulting particle preparations were normally passed through a # 60 mesh sieve to remove large particles. These particles were examined microscopically with a Leitz Dialux 20EB microscope to check for crystals and particle morphology, and evaluated using a Coulter LS-130 particle size analyzer to determine average particle size and the number of modes in the distribution.

To assay the rate of release of active ingredient from particle formulations, an aliquot of a formulation was placed in a glass bottle at a concentration at which a released active ingredient was expected to be <½ the water solubility level. A solvent was then added (water or 10% acetone). At various intervals, the bottle was shaken (200 times at time 0, 20 times for other intervals). An aliquot was removed, centrifuged 15 minutes at 2700 rpm, and filtered through a 0.45 micron PTFE filter (after discarding the first 2 mL). Assays for epoxiconazole and tebuconazole were then carried out by HPLC.

Particle suspensions having the following compositions were produced.

Epoxiconazole-Containing Matrix Particle Formulations-Compositon (%, w/w)

| Ingredients | Weight % of Ingredients Formulation | | |
|---|---|---|---|
| | 52 | 53 | 54 |
| Epoxiconazole (100% a.i. basis) | 3.00 | 3.00 | 3.00 |
| Polymer | 27.00 (a) | 12.00 (b) | 12.00 (b) |
| METHOCEL ® A15LV (methycellulose formulation) | — | — | 2.00 |
| ELVANOL ® 51-05 (partially hydolyzed polyvinyl alcohol formulation) | 4.00 | — | — |
| YELKINOL ® P (lecithin formulation) | — | 1.50 | — |
| Water | 83.50 | 83.50 | 83.00 |
| Total | 100.00 | 100.00 | 100.00 |

Evaluation Data

| | Formulation | | |
|---|---|---|---|
| | 52 | 53 | 54 |
| Loading of a.i. (% w/w) | 10% | 20% | 20% |
| O/W ratio in emulsion | 1/5 | 3/2 | 3/2 |
| Ave. particle size, mode: | 11.35 µm, trimodal | 1.37 µm, bimodal | 3.04 µm, bimodal |
| Init. % a.i./% REA* | 3.57/0.18 | 3.44/1.00 | 3.94/0.2 |

Polymers: (a) Poly(methylmethacrylate), (b) Poly(styrene/maleic anhydride)
*REA = Readily Extractable Active.

Tebuconazole-Containing Matrix Particle Formulations-Composition (%, w/w)

| Ingredients | Weight % of Ingredients Formulation | | |
|---|---|---|---|
| | 55 | 56 | 57 |
| Tebuconazole (100% a.i. basis) | 3.00 | 4.50 | 6.00 |
| Polymer* | 12.00 (a) | 10.50 (a) | 9.00 (a) |
| METHOCEL ® A15LV (methylcellulose formulation) | 1.00 | 1.00 | 1.00 |
| Water | 84.00 | 84.00 | 84.00 |
| Total | 100.00 | 100.00 | 100.00 |

Evaluation Data

| | Formulation | | |
|---|---|---|---|
| | 52 | 53 | 54 |
| Loading of a.i., % | 20 | 30 | 40 |
| O/W Ratio in emulsion | 3/2 | 3/2 | 3/2 |
| Ave. particle size, mode: | 9.14 µm, bimodal | 7.36 µm, bimodal | 13.48 µm, trimodal |
| Init. % a.i./% REA: | 3.25/0.68 | 4.92/2.01 | 5.75/2.21 |

*(a) Poly(methylmethacrylate), (b) Poly(styrene/maleic anhydride)

In addition, phytotoxicity of the formulations on wheat and their release rates into water and into 10% acetone solutions were determined. This information is summarized below.

Epoxiconazole-Containing Matrix Particle Formulations-Phytotoxicity and Release Rates

| | Formulation | | |
|---|---|---|---|
| | 58 | 53 | 54 |
| | % Release of epoxiconazole, after 269 hrs | | |
| into water | 0.9 | 6.56 | 1.63 |
| into 10% Acetone | 9.71 | 46.7 | 26.6 |
| | Safety on Wheat* | | |
| 25 g a.i./100 kg seed | 96.9% (25.4 g) | 66.4% (12.4 g) | 92.2% (28.6 g) |
| 50 g a.i./100 kg seed | 91.8% (46.4 g) | 20.0% (42.2 g) | 75.4% (53.3 g) |
| OPUS ® (epoxiconazole formulation), 8 g/100 kg | 22.5% (6.4 g) | | |
| Control (0 g a.i./100 kg) | 100% (0 g) | | |

*Plant height as a % of the height of untreated control plants. Numbers in parenthesis are the grams of active ingredient found by assay to be on 100 kg of treated seed.

Tebuconazole-Containing Matrix Particle Formulations-Phytotoxicity and Release Rates

| | Formulation | | |
|---|---|---|---|
| | 55 | 56 | 57 |
| | % Release, 269 hrs | | |
| into water | 2.53 | 3.79 | 14.5 |
| into 10% acetone | 24.9 | 46.2 | 60.0 |
| | Safety on Wheat* | | |
| 50 g/100 kg seed | 89.7% (47 g) | 78.4% (45 g) | 70.3% (49 g) |
| 75 g/100 kg seed | 83.8% (70 g) | 77.3% (72 g) | 68.7% (78 g) |
| 100 g/100 kg seed | 78.4% (95 g) | 74.1% (92 g) | 60.8% (99 g) |
| Raxil, 25 g/100 kg | 40.3% (26 g) | | |
| Control (0 g/100 kg) | 100% (0 g) | | |

*% of height of untreated control.
Numbers in parenthesis are the grams of active ingredient found by assay to be on 100 kg of treated seed.

Particles having the same polymer and active ingredient loading (Formulation 53 versus Formulation 54) but using a different dispersant have much different release rates and corresponding differences in safety on wheat. The high release rate and higher initial % REA of Formulation 53 gives a product having poor safety on wheat. However the same loading in the same polymer processed with a different dispersant gives a recipe with a lower release rate and readily extractable active (REA) and higher safety on wheat. In addition, the rates of release of active ingredients are higher (and safety on wheat decreases correspondingly) as the loading in the particle is increased.

This study indicates that release rates can be changed by processing and active ingredient loading (concentration) in the matrixed particle. As active ingredient concentration increases, release rates increase likewise. Lower release rates tend to result in higher safety on wheat. When different dispersing agents are used for the preparation of emulsions, the emulsion quality and the release rate of the resulting particles are affected.

Poly(methylmethacrylate) and poly(styrene-maleic anhydride) are useful polymers for producing particles that increase the safety of epoxiconazole and tebuconazole on wheat.

Example 23

For this Example, the polymer used was poly(styrene/maleic anhydride) (75% styrene, Sigma Chemical Co., St. Louis, Mo.). All organic solvents were of American Chemical Society (A.C.S.) analytical reagent grade. The dispersing agent used was METHOCEL® A15LV (methylcellulose formulation) (methyl cellulose Dow Chemical, Midland, Mich.). The active ingredients used were as follows: the fungicide triticonazole (technical grade @ 91.8%, Rhône-Poulenc Ag Co., Research Triangle Park, N.C.), the herbicide triallate (technical grade @ 94%; Monsanto Company, St. Louis, Mo.), the Strobilurin fungicide MON 46100 (technical grade @ 95%; Monsanto Company, St. Louis, Mo.), the herbicide safener furilazole (MON 13900, technical grade @ 95%; Monsanto Company, St. Louis, Mo.); the insecticide chlorpyrifos (high purity grade @ 99%; Dow Chemical Co., Midland, Mich.); a morpholine-type fungicide, fenpropimorph (used "as is" in the form of the 750 g/L Corbel formulation, BASF AG, Limburgerhof, Germany); a carbamoyl imidazole-type fungicide, prochloraz (high purity grade @ 99%; Monsanto Company, St. Louis, Mo.).

Matrixed particle formulations were prepared by an oil-in-water (O/W) emulsion/solvent evaporation procedure. Briefly, the polymer and active ingredient used were dissolved in methylene chloride at room temperature to form a 15% solids hydrophobic (oil, O) solution. This oil phase was added to a cooled (<5° C.) 0.5-3.0% aqueous dispersant solution (water, W) and sheared with a Silverson Model L4R homogenizer (large hole screen, 1.5 cm.) for 5 minutes at setting #5 to form an emulsion. The organic solvent was then evaporated with stirring at ambient temperatures in a fume hood. The resulting formulations were normally passed through a # 60 mesh sieve to remove large particles and then evaluated. The particles were subjected to microscopic examination with a Leitz Dialux 20EB microscope to check for crystals and particle morphology and a particle-size evaluation using a Coulter LS-130 particle size analyzer to determine the average particle size and number of modes in the distribution.

Test compositions were prepared and their physical properties evaluated. The two recipes used are described below. Recipe B was necessary for triticonazole because much crystal growth occurs when recipe A is used. Recipe A produces a 20% active ingredient loading for the particles and Recipe B produces a 5% loading.

| | Recipes (%, w/w) | |
|---|---|---|
| Ingredients | Recipe A | Recipe B |
| Active Ingredient | 3.00 | 0.75 |
| Poly(styrene/maleic anhydride) 75:25 | 12.00 | 14.25 |
| METHOCEL ® A15LV (methylcellulose formulation) | 2.00 | 2.00 |

-continued

| | Recipes (%, w/w) | |
|---|---|---|
| Ingredients | Recipe A | Recipe B |
| Water | 83.00 | 83.00 |
| Total | 100.00 | 100.00 |

Particle size analyses were carried out on the Formulation 59 and fenpropimorph recipes and estimates from photographs were used for the other recipes.

TABLE 6

| | Recipe References | | |
|---|---|---|---|
| Active Ingredient | Formulation | Recipe | Ave. size (μm) |
| Triticonazole | 60 | B | ~5 |
| MON 46100 | 61 | A | 5.4 |
| Fenpropimorph | 62 | A | 2.7 |
| Furilazole | 63 | A | ~5 |
| Triallate | 64 | A | ~5 |
| Chlorpyrifos | 65 | A | ~5 |
| Prochloraz | 66 | A | 4.8 |

Formulation 62 showed increased safety compared to Corbel, a commercial fast-release formulation of fenpropimorph, when applied as a seed treatment to wheat at rates of 50-200 gm a.i./100 kg seed.

Example 24

Polymers used were poly(methyl methacrylate) (350,000 MW, Polysciences, Inc., Warrington, Pa.) and poly(styrene/maleic anhydride) (75% styrene, Sigma Chemical Co., St. Louis, Mo.) were used. All organic solvents were of American Chemical Society (A.C.S.) analytical reagent grade. Dispersing agents used were METHOCEL® A15LV (methylcellulose formulation) (Dow Chemical, Midland, Mich.) and ELVANOL® 51-05 (partially hydrolyzed polyvinyl alcohol formulation) (polyvinyl alcohol, DuPont, Wilmington, Del.).

Particles were prepared by an oil-in-water (O/W) emulsion/solvent evaporation procedure. Briefly, the polymer and active ingredient used were dissolved in methylene chloride at room temperature to form a 15% solids hydrophobic solution (oil phase, O). This oil phase was added to a cooled (<5° C.) 0.5-3.0% aqueous dispersant solution (aqueous solution, W) and sheared with a Silverson Model L4R homogenizer (large hole screen, 1.5 cm.) for 5 minutes at setting #3 to form an emulsion. The solvent was then evaporated with stirring at ambient temperatures in a fume hood. Assays for active ingredient concentration were made and further evaporation of water was carried out to give the calculated final concentration. The resulting particles were passed through a # 60 mesh sieve to remove large particles and then evaluated. Several evaluations were made, including microscopic examination with a Leitz Dialux 20EB microscope, pH, density, viscosity, and particle size distribution by Coulter LS-130 particle size analyzer.

Seed treatment formulations, their physical properties, and phytotoxicity data from greenhouse trials are described below.

Seed Treatment Formulations

| Ingredients | 67 | 68 | 69 | 70 | 71 | 72 | 73 | 74 |
|---|---|---|---|---|---|---|---|---|
| Epoxiconazole* | 3.00 | 3.00 | 3.00 | 3.00 | — | — | — | — |
| Tebuconazole* | — | — | — | — | 10.00 | 10.00 | 10.00 | 10.00 |
| Polymer | 27.00 (1) | 12.00 (2) | 27.00 (2) | 12.00 (1) | 40.00 (2) | 15.00 (2) | 40.00 (1) | 15.00 (1) |
| Methyl Cellulose | — | 1.86 | 1.00 | 1.50 | 1.40 | 1.70 | 1.40 | 1.58 |
| Polyvinyl Alcohol | 3.85 | — | — | — | — | — | — | — |
| Water | 66.15 | 83.14 | 69.00 | 83.50 | 48.60 | 73.30 | 48.60 | 73.42 |
| Total | 100.00 | 100.00 | 100.00 | 100.00 | 100.00 | 100.00 | 100.00 | 100.00 |

*100% a.i. basis.
Polymers: (1) poly(methylmethacrylate); (2), poly(styrene-maleic anhydride) copolymer 75:25 ratio.

The table below provides information regarding physical properties of the particle preparations.

Physical Properties

| Property | 67 | 68 | 69 | 70 | 71 | 72 | 73 | 74 |
|---|---|---|---|---|---|---|---|---|
| % a.i. | 2.94 | 3.01 | 2.96 | 2.93 | 9.39 | 10.13 | 9.89 | 9.98 |
| % REA | 0.27 | 0.19 | 0.03 | 0.55 | 0.08 | 1.19 | 0.24 | 1.50 |
| t° (C.) when measured | 23.7 | 23.7 | 24.2 | 23.0 | 23.3 | 23.2 | 22.9 | 23.2 |
| Density, g/mL | 1.07 | 1.03 | 1.05 | 1.03 | 1.08 | 1.05 | 1.10 | 1.05 |
| Viscosity, 60 rpm, cps | 3.61 | 2.04 | 3.34 | 1.97 | 19.0 | 4.46 | 25.9 | 4.21 |
| pH | 7.07 | 4.02 | 3.36 | 6.82 | 3.31 | 3.77 | 6.25 | 5.96 |

Phytotoxicity of Tebuconazole-Containing Formulation (% of Contol Height)

| g a.i./ 100 kg seed | 71 | 72 | 73 | 74 | 75 | RAXIL® (thiram formulation) |
|---|---|---|---|---|---|---|
| 16 | — | — | — | — | — | 76.3 |
| 25 | — | — | — | — | 95.5 | — |
| 50 | 82.1 | 69.8 | 89.7 | 70.3 | 89.6 | — |
| 75 | 84.5 | 64.4 | 83.8 | 68.7 | — | — |
| 100 | — | — | 78.4 | 60.8 | — | — |

LSD(.05) = 19.14

Phytotoxicity of Epoxiconazole-Containing Formulation (% of Contol Height)

| g a.i./ 100 kg seed | MON 24531 | MON 24532 | MON 24533 | MON 24534 | MON 24555 | OPUS® (epoxiconazole formulation) |
|---|---|---|---|---|---|---|
| 5 | — | — | — | — | — | 32.5 |
| 25 | 93.8 | 91.2 | 93.8 | 83.0 | 96.2 | 8.6 |
| 50 | 83.4 | 73.3 | 98.0 | 43.3 | 90.5 | — |
| 75 | 77.9 | 61.4 | 86.8 | 24.3 | 87.9 | — |

Epoxiconazole-containing formulations showed much less phytotoxicity than the commercial reference, OPUS® (epoxiconazole formulation). Likewise, tebuconazole-containing formulations showed less phytotoxicity than the commercial reference, RAXIL® (thiram formulation).

Formulation 75 and Formulation 76 were also tested as foliar treatments of soybean. At rates of 50 and 250 ppm active ingredient, soybean plants treated with Formulation 75 and Formulation 76 as foliar treatments displayed substantially greater vigor than plants treated with FOLICUR® (tebuconazole formulation, Bayer) and OPUS® (epoxiconazole formulation), particularly at the higher application rate.

The dispersant used for all of the formulations was METHOCEL® A15LV (methylcellulose formulation), with the exception of Formulation 67. This formulation showed better processing with ELVANOL® 51-05 (partially hydrolyzed polyvinyl alcohol formulation) as a dispersant.

Example 25

Figure 17:
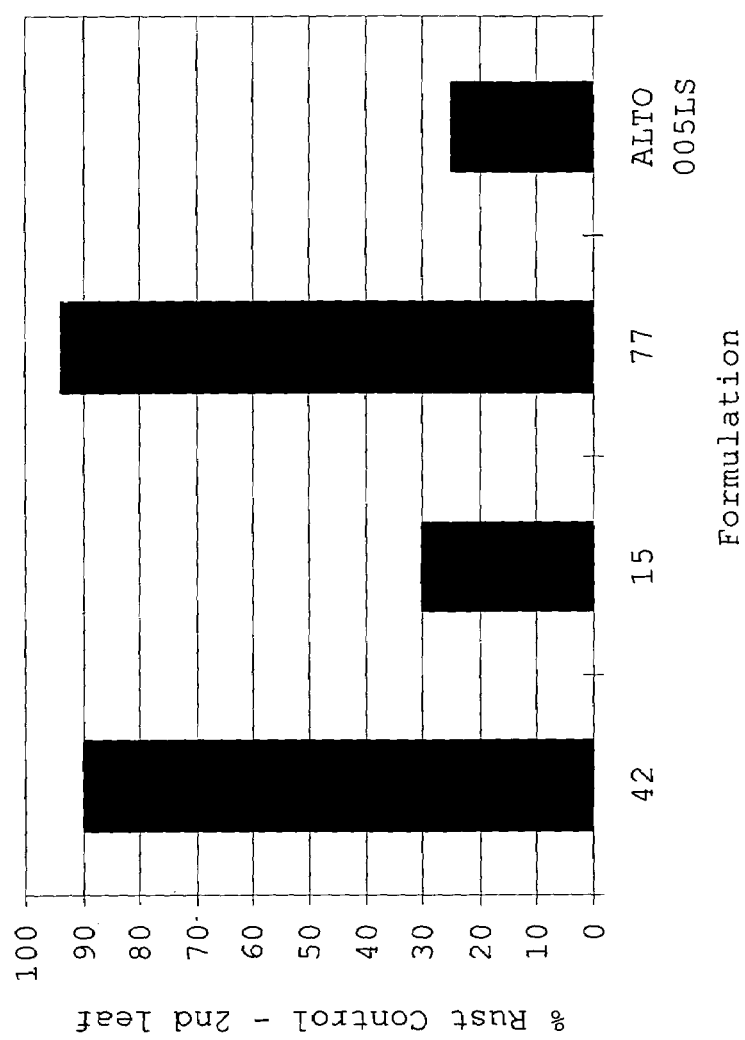
FIG. 17 shows control of brown rust of wheat (second leaf) by seed coatings comprising matrix particle Formulation 47, Formulation 15, Formulation 77 (each at 32 g cyproconazole per 100 kg seed), and ALTO® 005LS (cyproconazole formulation) (1 g cyproconazole per 100 kg seed). Plants were inoculated 20 DAP. Disease severity in untreated controls was 61.3%.

We evaluated particle formulations containing cyproconazole for efficacy and duration in controlling brown leaf rust of wheat (caused by *Puccinia recondita*) in greenhouse experiments. Wheat seed (cv. FORTUNA™ (wheat variety)) were treated with test treatments (Formulation 42, Formulation 15, or Formulation 77, all at 32 g cyproconazole per 100 kg seed) and ALTO® 005LS (cyproconazole formulation) (at 1 g cyproconazole per 100 kg seed) and seeded in standard 4" square pots containing sterilized Dupo silt loam soil. Seeding was done at a rate of 1 seed per pot, with four replicate pots of each treatment rate. Seeds were covered with approximately 2 cm of the same soil and incubated under a 12 hour photoperiod, at 50% relative humidity. Growth room temperatures were maintained at 16° C. during the 12 hour light period and at 12° C. during the 12 hour dark period. Twenty days after planting, plants grown from treated seed were inoculated with urediospores of *P. recondita*. The inoculated plants were incubated for 24 hours in a mist tent at 20° C. to allow for disease infection. Disease severity was evaluated 8-10 days after inoculation. The table below and FIG. 17 show the percent of rust control in this experiment in plants inoculated 20 days after planting (second leaf stage). Disease severity in untreated control plants was about 61.3%. We observed an increase in the efficacy and duration of disease control by matrix particle formulations, which permitted treatment of plants with a higher rate of the active ingredient than would be tolerated if the plants were treated with a standard formulation such as ALTO® 005LS (cyproconazole formulation).

| Formulation | % Rust Control (2nd Leaf) |
|---|---|
| 42 | 90 |
| 15 | 30 |
| 77 | 94 |
| ALTO ® 005LS (cyproconazole formulation) | 25 |

Example 26

Readily Extractable Active Ingredient (REA)

The following method can be used to estimate the amount of free active outside the particle of the present invention active plus the active ingredient immediately extractable with water from the particle of the present invention.

Transfer an aliquot of the formulation to glass bottle. Add water shake 200 times. Immediately withdraw an aliquot of the shaken solution and filter it through a 0.45 micron PTFE filter (discarding the first 3 mL). Assay by HPLC. The resulting raw ppm value in the tested aliquot must be less than half of the saturation concentration of the active ingredient assayed. If the raw ppm value is higher than half the saturation concentration of the active ingredient, the procedure must be rerun with less formulation. For example, the water saturation concentration of epoxiconazole is 7 ppm at room temperature. Therefore, the maximum resulting raw ppm value in a tested aliquot of an epoxiconazole shaken solution must be less than 3.5 ppm. The water saturation concentration of tebuconazole is 32 ppm. Therefore, the maximum resulting raw ppm value in a tested aliquot of a tebuconazole shaken solution must be less than 16 ppm.

Example 27

Release Rate Assay—General Method

An aliquot of formulation is placed in a glass bottle at a concentration where released triazole is expected to be <½ the water solubility level. Water is added so that the total volume is about 450 mL. The pH of the medium is maintained or adjusted using a phosphate buffer. At various intervals the bottle is shaken (200 times at time 0, 20 times for other intervals). An aliquot is removed, centrifuged 15 minutes at 2700 rpm, and filtered through a 0.45 micron PTFE filter (after discarding the first 2 mL). Assays for epoxiconazole and tebuconazole are then carried out by HPLC. If the experiment calls for an adjustment of pH during the course of the experiment, the pH is adjusted using a phosphate buffer and an aliquot is immediately removed for assay.

Many changes and modifications of the invention described in this specification will occur to those skilled in the art upon studying the teachings of this specification. All such changes and modifications which are within the spirit of the present invention are intended to be included in the claims.

What is claimed is:

1. A method of producing a solid particle wherein the particle is free of a plasticizer and comprises a triazole fungicide dispersed throughout a solid polymer matrix, the method comprising:
    (a) providing a hydrophobic solution comprising the triazole fungicide, a polymer, and a solvent;
    (b) mixing the hydrophobic solution and an aqueous medium to produce a dispersion of droplets of the hydrophobic solution in the aqueous medium; and
    (c) evaporating the solvent from the dispersion to produce the solid particle which is free of a plasticizer and which comprises the triazole fungicide dispersed throughout the solid polymer matrix.

2. The method of claim 1 wherein the triazole fungicide is selected from the group consisting of bitertanol, bromuconazole, cyproconazole, difenoconazole, epoxiconazole, fenbuconazole, fluquinconazole, flusilazole, flutriafol, hexaconazole, imibenconazole, metconazole, myclobutanil, penconazole, propiconazole, tebuconazole, tetraconazole, triadimefon, triadimenol, and triticonazole.

3. The method of claim 2 wherein the triazole fungicide is selected from the group consisting of cyproconazole, epoxiconazole, tebuconazole, triadimefon, and triadimenol.

4. The method of claim 2 wherein the triazole fungicide is cyproconazole.

5. The method of claim 2 wherein the triazole fungicide is tebuconazole.

6. The method of claim 2 wherein the triazole fungicide is epoxiconazole.

7. The method of claim 2 wherein the triazole fungicide is triadimenol.

8. The method of claim 2 wherein the triazole fungicide is triadimefon.

9. The method of claim 1 wherein the hydrophobic solution further comprises a dispersing agent.

10. The method of claim 1 wherein the aqueous medium comprises a dispersing agent.

11. The method of claim 1 wherein the solvent is a hydrophobic solvent.

12. The method of claim 1 wherein the solvent comprises a compound selected from the group consisting of halogenated hydrocarbons, aromatic compounds, hydrocarbons, ethers, and esters.

13. The method of claim 1 wherein the solvent comprises a compound selected from the group consisting of methylene chloride, ethyl acetate, chloroform, carbon tetrachloride, acetonitrile, diethyl ether, dimethyl ether, acetone, methylethylketone, pentane, hexane, hexanes, heptane, dioxane, ethanol, methanol, pyridine, propanol, 2-propanol, butanol, 2-butanol, t-butyl alcohol, isobutyl alcohol, perchloroethylene, tetrachloroethane, o-xylene, m-xylene, p-xylene, toluene, benzene, mesitylene, chlorobenzene, o-dichlorobenzene, m-dichlorobenzene, and p-dichlorobenzene.

14. The method of claim 13 wherein the solvent comprises methylene chloride.

15. The method of claim 1 wherein step (c) comprises applying a source of vacuum to the dispersion.

16. The method of claim 1 wherein step (c) comprises applying heat to the dispersion.

17. The method of claim 1 wherein step (c) comprises lyophilizing the dispersion.

18. The method of claim 1, wherein the polymer matrix comprises a polymer selected from the group consisting of poly(methylmethacrylate), poly(lactic acid), a poly(lactic acid-glycolic acid) copolymer, cellulose acetate butyrate, a poly(styrene), hydroxybutyric acid-hydroxyvaleric acid copolymer, a styrene maleic anhydride copolymer, poly(methylvinyl ether-maleic acid), poly(caprolactone), poly(n-amylmethacrylate), wood rosin, a polyanhydride, a polyorthoester, a poly(cyanoacrylate), poly(dioxanone), ethyl cellulose, a ethyl vinyl acetate polymer, poly(ethylene glycol), poly(vinylpyrrolidone), an acetylated monogylceride, an acetylated digylceride, an acetylated trigylceride, poly(phosphazene), chlorinated natural rubber, a vinyl polymer, polyvinyl chloride, a hydroxyalkylcellulose, polybutadiene, polyurethane, a vinylidene chloride polymer, a styrene-butadiene copolymer, a styrene-acrylic copolymer, an alkylvinylether polymer, a cellulose acetate phthalate, an ethyl vinyl phthalate, cellulose triacetate, a polyanhydride, a polyglutamate, a polyhydroxy butyrate, polyvinyl acetate, a vinyl acetate-ethylene copolymer, a vinyl acetate-vinylpyrrolidone copolymer, an acrylic polymer, an alkyl acrylate polymer, an aryl acrylate polymer, an aryl methacrylate polymer, a poly(caprolactam), an epoxy resin, a polyamine epoxy resin, a polyamide, a polyvinyl alcohol polymer, a polyalkyd resin, a phenolic resin, an abietic acid resin, a silicone, a polyalkylene oxide, and a polyester.

19. The method of claim 1, wherein the mean diameter of said particle is in the range of from about 0.1 microns to about 200 microns.

20. The method of claim 1, wherein the mean diameter of said particle is in the range of from about 0.2 microns to about 100 microns.

21. The method of claim 1, wherein the mean diameter of said particle is in the range of from about 0.5 microns to about 50 microns.

22. The method of claim 1, further comprising producing a fungicidal composition by intermixing said particles with an agricultural adjuvant.

23. The method of claim 22, wherein the fungicidal composition is in the form of a liquid suspension.

24. The method of claim 22, wherein the fungicidal composition is in the form of a wettable powder.

25. The method of claim 22, wherein the fungicidal composition is in the form of a granule.

26. The method of claim 25, wherein the granule is a water-dispersible granule.

27. The method of claim 22, wherein the agricultural adjuvant comprises a dispersant.

28. The method of claim 22, wherein the agricultural adjuvant comprises a diluent.

* * * * *

UNITED STATES PATENT AND TRADEMARK OFFICE
CERTIFICATE OF CORRECTION

| | |
|---|---|
| PATENT NO. | : 7,452,546 B2 |
| APPLICATION NO. | : 11/396019 |
| DATED | : November 18, 2008 |
| INVENTOR(S) | : M. Francis Botts, Frank C. Kohn and Maria L. Miller |

It is certified that error appears in the above-identified patent and that said Letters Patent is hereby corrected as shown below:

Col. 42, line 11, replace the terms "ALTO®" with the term -- ALTO® 005LS --.

Signed and Sealed this

Thirty-first Day of March, 2009

JOHN DOLL
*Acting Director of the United States Patent and Trademark Office*